(12) United States Patent
Oh et al.

(10) Patent No.: US 9,770,461 B2
(45) Date of Patent: *Sep. 26, 2017

(54) TAILORED GLYCOPOLYMERS AS ANTICOAGULANT HEPARIN MIMETICS

(71) Applicant: California Institute of Technology, Pasadena, CA (US)

(72) Inventors: Young In Oh, Berkeley, CA (US); Linda C. Hsieh-Wilson, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 14/450,196

(22) Filed: Aug. 1, 2014

(65) Prior Publication Data

US 2015/0038436 A1    Feb. 5, 2015

Related U.S. Application Data

(60) Provisional application No. 61/861,567, filed on Aug. 2, 2013.

(51) Int. Cl.
| | | |
|---|---|---|
| *C07H 15/18* | (2006.01) | |
| *A61K 31/7028* | (2006.01) | |
| *C08G 61/08* | (2006.01) | |

(52) U.S. Cl.
CPC .......... *A61K 31/7028* (2013.01); *C08G 61/08* (2013.01); *C08G 2261/1424* (2013.01); *C08G 2261/3324* (2013.01); *C08G 2261/418* (2013.01); *C08G 2261/90* (2013.01)

(58) Field of Classification Search
None
See application file for complete search history.

(56) References Cited

U.S. PATENT DOCUMENTS

| | | |
|---|---|---|
| 3,657,744 A | 4/1972 | Ersek |
| 4,376,110 A | 3/1983 | David et al. |
| 4,399,216 A | 8/1983 | Axel et al. |
| 4,739,762 A | 4/1988 | Palmaz |
| 4,740,461 A | 4/1988 | Kaufman |
| 4,816,567 A | 3/1989 | Cabilly et al. |
| 4,818,816 A | 4/1989 | Petitou et al. |
| 4,883,751 A | 11/1989 | Gitel et al. |
| 4,912,040 A | 3/1990 | Kaufman et al. |
| 4,946,778 A | 8/1990 | Ladner et al. |
| 4,959,455 A | 9/1990 | Clark et al. |
| 5,040,548 A | 8/1991 | Yock |
| 5,061,273 A | 10/1991 | Yock |
| 5,185,245 A | 2/1993 | Heimer |
| 5,195,984 A | 3/1993 | Schatz |
| 5,225,539 A | 7/1993 | Winter |
| 5,292,331 A | 3/1994 | Boneau |
| 5,292,658 A | 3/1994 | Cormier et al. |
| 5,418,155 A | 5/1995 | Cormier et al. |
| 5,451,233 A | 9/1995 | Yock |
| 5,464,758 A | 11/1995 | Gossen et al. |
| 5,484,892 A | 1/1996 | Tedder et al. |
| 5,496,346 A | 3/1996 | Horzewski et al. |
| 5,530,101 A | 6/1996 | Queen et al. |
| 5,585,089 A | 12/1996 | Queen et al. |
| 5,585,097 A | 12/1996 | Bolt et al. |
| 5,587,442 A | 12/1996 | Kiessling et al. |
| 5,589,362 A | 12/1996 | Bujard et al. |
| 5,631,146 A | 5/1997 | Szostak et al. |
| 5,650,298 A | 7/1997 | Bujard et al. |
| 5,674,278 A | 10/1997 | Boneau |
| 5,683,888 A | 11/1997 | Campbell |
| 5,691,145 A | 11/1997 | Pitner et al. |
| 5,693,761 A | 12/1997 | Queen et al. |
| 5,693,762 A | 12/1997 | Queen et al. |
| 5,728,851 A | 3/1998 | Franke |
| 5,741,668 A | 4/1998 | Ward et al. |
| 5,777,079 A | 7/1998 | Tsien et al. |
| 5,804,387 A | 9/1998 | Cormack et al. |
| 5,821,337 A | 10/1998 | Carter et al. |
| 5,846,534 A | 12/1998 | Waldmann et al. |
| 5,859,205 A | 1/1999 | Adair et al. |
| 5,874,304 A | 2/1999 | Zolotukhin et al. |
| 5,876,995 A | 3/1999 | Bryan |
| 5,879,382 A | 3/1999 | Boneau |
| 5,925,558 A | 7/1999 | Tsien et al. |
| 5,959,094 A | 9/1999 | Wallach et al. |
| 6,054,297 A | 4/2000 | Carter et al. |

(Continued)

FOREIGN PATENT DOCUMENTS

| | | |
|---|---|---|
| WO | WO-9201047 A1 | 1/1992 |
| WO | WO-9215673 A1 | 9/1992 |

(Continued)

OTHER PUBLICATIONS

De Paz, Jose et al., JACS, "Microarrays of Synthetic Heparin Oligosaccharides", 2006, vol. 128, pp. 2766-2767.*
Liu, Jian et al., Appl. Microbiol. Biotechnol., "Anticoagulant heparan sulfate: structural specificity and biosynthesis", 2007, vol. 74, pp. 263-272.*
U.S. Appl. No. 14/450,192, filed Aug. 1, 2014, Sheng et al.
Alban, et al. PS3, a semisynthetic beta-1,3-glucan sulfate, diminishes contact hypersensitivity responses through inhibition of L- and P-selectin functions. J Invest Dermatol. May 2009;129(5):1192-202. doi: 10.1038/jid.2008.358. Epub Dec. 4, 2008.
Alberts, et al. 1994. Molecular Biology of the Cell, Third Edition, Garland Publishing, Inc. New York & London, pp. 129-130.
Anderson, et al. Handbook of Clinical Drug Data. Tenth edition, McGraw-Hill, 2002.

(Continued)

*Primary Examiner* — Shaojia Anna Jiang
*Assistant Examiner* — Bahar Craigo
(74) *Attorney, Agent, or Firm* — Wilson Sonsini Goodrich & Rosati

(57) ABSTRACT

The present disclosure provides for methods and compositions comprising a series of synthetic glycopolymers. The disclosure also relates to a kit which is suitable for carrying out the inventive methods.

15 Claims, 14 Drawing Sheets

(56) References Cited

U.S. PATENT DOCUMENTS

| | | | |
|---|---|---|---|
| 6,057,153 A | 5/2000 | George et al. |
| 6,180,370 B1 | 1/2001 | Queen et al. |
| 6,200,564 B1 | 3/2001 | Lamont et al. |
| 6,291,616 B1 | 9/2001 | Kiessling et al. |
| 6,313,373 B1 | 11/2001 | Eckert et al. |
| 6,344,053 B1 | 2/2002 | Boneau |
| 6,407,213 B1 | 6/2002 | Carter et al. |
| 6,491,916 B1 | 12/2002 | Bluestone et al. |
| 6,680,304 B2 | 1/2004 | Vila Pahi et al. |
| 6,966,424 B2 | 11/2005 | Cram |
| 6,982,321 B2 | 1/2006 | Winter |
| 7,405,227 B2 | 7/2008 | Kun et al. |
| 7,638,503 B2 | 12/2009 | Hsieh-Wilson et al. |
| 7,745,584 B2 | 6/2010 | Tully et al. |
| 8,338,387 B2 | 12/2012 | Hsieh-Wilson et al. |
| 8,623,610 B2 | 1/2014 | Gama et al. |
| 8,912,011 B2 | 12/2014 | Tully et al. |
| 8,912,149 B1 | 12/2014 | Rawat et al. |
| 2003/0073147 A1 | 4/2003 | Alderete et al. |
| 2003/0108548 A1 | 6/2003 | Bluestone et al. |
| 2004/0006216 A1 | 1/2004 | Waldmann et al. |
| 2004/0166099 A1 | 8/2004 | Rao |
| 2004/0186142 A1 | 9/2004 | Taveras et al. |
| 2005/0130235 A1 | 6/2005 | Hsieh-Wilson |
| 2005/0180945 A1 | 8/2005 | Chaikof et al. |
| 2006/0002921 A1 | 1/2006 | Winsor-Hines et al. |
| 2006/0025379 A1 | 2/2006 | Hsieh-wilson et al. |
| 2006/0211651 A1 | 9/2006 | Miyasaka et al. |
| 2007/0044161 A1 | 2/2007 | Soutschek et al. |
| 2007/0275412 A1 | 11/2007 | Gama et al. |
| 2008/0009607 A1 | 1/2008 | Tully et al. |
| 2008/0124339 A1 | 5/2008 | Pullen et al. |
| 2010/0071080 A1 | 3/2010 | Tully et al. |
| 2010/0075920 A1 | 3/2010 | Hsieh-wilson et al. |
| 2011/0020359 A1 | 1/2011 | Hsieh-Wilson et al. |
| 2011/0136201 A1 | 6/2011 | Mao et al. |
| 2014/0323699 A1 | 10/2014 | Hsieh-Wilson et al. |
| 2015/0038455 A1 | 2/2015 | Sheng et al. |
| 2015/0369809 A1 | 12/2015 | Hsieh-Wilson et al. |

FOREIGN PATENT DOCUMENTS

| | | |
|---|---|---|
| WO | WO 92/22653 A1 | 12/1992 |
| WO | WO 93/21319 A1 | 10/1993 |
| WO | WO-9507463 A1 | 3/1995 |
| WO | WO-9814605 A1 | 4/1998 |
| WO | WO-9826277 A2 | 6/1998 |
| WO | WO-9949019 A2 | 9/1999 |
| WO | WO 01/23426 A2 | 4/2001 |
| WO | WO 03/002125 A2 | 9/2003 |
| WO | WO 03/002125 A3 | 11/2003 |
| WO | WO 2004/011662 A1 | 2/2004 |
| WO | WO 2004/017910 A2 | 3/2004 |
| WO | WO 2004/017910 A3 | 9/2004 |
| WO | WO 2012/065139 A2 | 5/2012 |

OTHER PUBLICATIONS

Arungundram, et al. Modular synthesis of heparan sulfate oligosaccharides for structure-activity relationship studies. J Am Chem Soc. Dec. 2, 2009;131(47):17394-405. doi: 10.1021/ja907358k.

Becker, et al. "Fucose: biosynthesis and biological function in mammals." Glycobiology (2003) 13 (7): 41R-53R. doi: 10.1093/glycob/cwg054.

Belot, et al. Unexpected stereochemical outcome of activated 4,6-O-benzylidene derivatives of the 2-deoxy-2-trichloroacetamido-D-galacto series in glycosylation reactions during the synthesis of a chondroitin 6-sulfate trisaccharide methyl glycoside. Carb. Res. (2000) 325:93-106.

Berge, et al. Pharmaceutical salts. J Pharm Sci. Jan. 1977;66(1):1-19.

Bergefell, et al. Chondroitin sulfate characterized by the E-disaccharide unit is a potent inhibitor of herpes simplex virus infectivity and provides the virus binding sites on gro2C cells. J Biol Chem. Sep. 16, 2005; 280(37):32193-9.

Bielawski, et al. Living Ring-Opening Metathesis Polymerization. Prog. Polym. Sci. 2007, 32, 1-29.

Bishop, et al. Heparan sulphate proteoglycans fine-tune mammalian physiology. Nature. Apr. 26, 2007;446(7139):1030-7.

Blatter, et al. The use of 2-deoxy-2-trichloroacetamido-D-glucopyranose derivatives in synthesis of oligosaccharides. Carb. Res. (1994) 260:189-202.

Blixt, et al. Glycan microarrays for screening sialyltransferase specificities. Glycoconj J. Jan. 2008;25(1):59-68. Epub Oct. 4, 2007.

Blixt, et al. Printed covalent glycan array for ligand profiling of diverse glycan binding proteins. Proc Natl Acad Sci U S A. Dec. 7, 2004;101(49):17033-17038. Epub Nov. 24, 2004.

Borish, et al. 2. Cytokines and chemokines. J Allergy Clin Immunol. Feb. 2003;111(2 Suppl):S460-75.

Bradbury, et al. Chondroitinase ABC promotes function recovery after spinal cord injury. Nature. 2002; 416:636-640.

Brittis, et al. Chondroitin sulfate as a regulator of neuronal patterning in the retina. Science. 1992; 255:733-736.

Caldas, et al. Humanization of the anti-CD18 antibody 6.7: an unexpected effect of a framework residue in binding to antigen. Mol Immunol. May 2003; 39(15):941-52.

Campbell (Monoclonal Antibody Technology, Laboratory Techniques in Biochemistry and Molecular Biology, Elsevier Science Publishers B.V.: Amsterdam, The Netherlands, vol. 13, pp. 1-32, 1984).

Canales, et al. Conformational flexibility of a synthetic glycosylaminoglycan bound to a fibroblast growth factor. FGF-1 recognizes both the (1)C(4) and (2)S(O) conformations of a bioactive heparin-like hexasaccharide. J Am Chem Soc. Apr. 27, 2005;127(16):5778-9.

Chang, et al. Expression of Globo H and SSEA3 in breast cancer stem cells and the involvement of fucosyl transferases 1 and 2 in Globo H synthesis. Proc Natl Acad Sci U S A. Aug. 19, 2008;105(33):11667-11672. doi: 10.1073/pnas.0804979105. Epub Aug. 6, 2008.

Chang, et al. Rapid characterization of sugar-binding specificity by in-solution proximity binding with photosensitizers. Glycobiology. Jul. 2011;21(7):895-902. doi: 10.1093/glycob/cwr021. Epub Feb. 16, 2011.

Chen, et al. Advances of Olefin Polymerization in Aqueous Solutions. Progress in Chemistry. 2003; 15(5):401-408. (in Chinese with English abstract).

Chien, et al. Significant structural and functional change of an antigen-binding site by a distant amino acid substitution: proposal of a structural mechanism. Proc Natl Acad Sci U S A. Jul. 1989; 86(14):5532-6.

Choay, et al. Structure-activity relationship in heparin: a synthetic pentasaccharide with high affinity for antithrombin III and eliciting high anti-factor Xa activity. Biochem Biophys Res Commun. Oct. 31, 1983;116(2):492-9.

Clark, et al. Direct in-gel fluorescence detection and cellular imaging of O-GlcNAc-modified proteins. J Am Chem Soc. Sep. 3, 2008;130(35):11576-11577. doi: 10.1021/ja8030467. Epub Aug. 7, 2008.

Coats, et al. Trimethylsilyl-directed 1,3-dipolar cycloaddition reactions in the solid-phase synthesis of 1,2,3-triazoles. Org Lett. Apr. 14, 2005;7(8):1469-72.

Colnaghi, et al. A multiparametric study by monoclonal antibodies in breast cancer. In: R.L. Ceriani (ed.) Immunological approaches to the diagnosis and therapy of breast cancer. pp. 21-32, Plenum Publishing Corp., 1987.

Cornish, et al. Site-Specific Protein Modification Using a Ketone Handle. J. Am. Chem. Soc. 1996; 118(34):8150-.8151.

Cote, et al. Generation of human monoclonal antibodies reactive with cellular antigens. Proc Natl Acad Sci U S A. Apr. 1983;80(7):2026-30.

Cote, et al. The EBV-Hybridoma technique and its application to human lung cancer. In Monoclonal antibodies and cancer therapy. Alan R. Liss, Inc. 1985; 77-96.

(56) References Cited

OTHER PUBLICATIONS

Das, et al. Synthesis of Conformationally Locked 1-Iduronic Acid Derivatives: Direct Evidence for a Critical Role of the Skew-Boat 2S0 Conformer in the Activation of Antithrombin by Heparin. Chemistry—A European Journal. Nov. 19, 2001; 7 (22): 4821-4834.
Davie, et al. The coagulation cascade: initiation, maintenance, and regulation. Biochemistry. Oct. 29, 1991;30(43):10363-70.
De Paz, et al. Profiling heparin-chemokine interactions using synthetic tools. ACS Chem Biol. Nov. 20, 2007;2(11):735-44.
Delves. The role of glycosylation in autoimmune disease. Autoimmunity. 1998;27(4):239-53.
Deng, et al. Phosphorylation of bad at Thr-201 by JNK1 promotes gycolysis through activation of phosphofructokinase-1. J Biol Chem, Jul. 25, 2008, vol. 283, No. 30, pp. 20754-20760, entire document.
Dewitt, et al. Chondroitin sulfate proteoglycans are a common component of neuronal inclusions and astrocytic reaction in neurodegenerative diseases. Brain Res. Sep. 5, 1994;656(1):205-9.
Dilhas, et al. Efficient selective preparation of methyl-1,2,4-tri-O-acetyl-3-O-benzyl-beta-L-idopyranuronate from methyl 3-O-benzyl-L-iduronate. Carbohydr Res. Mar. 28, 2003;338(7):681-6.
Dou, et al. Differential effects of glycosaminoglycans on neurite growth on laminin and L1 substrates. J. Neurosci. 1995; 15:8053-8066.
Dube, et al. Glycans in cancer and inflammation—potential for therapeutics and diagnostics. Nat Rev Drug Discov, Jun. 2005, vol. 4, No. 6, pp. 477-488, entire document.
Emerling, et al. Inhibitors and promoters of thalamic neuron adhesion and outgrowth in embryonic neocortex: functional association with chondroitin sulfate. Neuron. 1996; 17:1089-1100.
Falshaw, et al. Comparison of the glycosaminoglycans isolated from the skin and head cartilage of Gould's arrow squid (*Nototodarus gouldi*). Carbohydrate Polymers. 2000; 41:357-364.
Fan, et al. Orthogonal sulfation strategy for synthetic heparan sulfate ligands. Org Lett. Oct. 27, 2005;7(22):5095-8.
Fang, et al. The ER UDPase ENTPD5 promotes protein N-glycosylation, the warburg effect, and proliferation in the PTEN pathway. Cell, Nov. 24, 2010, vol. 143, No. 5, pp. 711-724, entire document.
Fournier, et al. Identification of a receptor mediating Nogo-66 inhibition of axonal regeneration. Nature. Jan. 18, 2001; 409(6818):341-6.
Frauwirth, et al. Regulation of T lymphocyte metabolism. The Jounral of Immunology, Apr. 15, 2004, vol. 172, No. 8, pp. 4661-4665, entire document.
Fukui, et al. Oligosaccharide microarrays for high-throughput detection and specificity assignments of carbohydrate-protein interactions. Nat Biotechnol. Oct. 2002;20(10):1011-7. Epub Sep. 3, 2002.
Fundamental Immunology p. 242 (William E. Paul, M.D. ed., 3d ed; 1993.
Gama, et al. Sulfation patterns of glycosaminoglycans encode molecular recognition and activity. Nat Chem Biol. Sep. 2006; 2(9):467-73.
Garland, Ed. Immunobiology. Janeway, 2001, pp. 102-103.
Garrett and Grisham. "Biochemistry" Published 1999 by Saunders College Publishers, p. 236.
Gavard, et al. Efficient Preparation of Three Building Blocks for the Synthesis of Heparan Sulfate Fragments: Towards the Combinatorial Synthesis of Oligosaccharides from Hypervariable Regions. European Journal of Organic Chemistry. Sep. 2003; 2003(18): 3603-3620.
Geng, et al. Site-directed conjugation of "clicked" glycopolymers to form glycoprotein mimics: binding to mammalian lectin and induction of immunological function. J Am Chem Soc. Dec. 12, 2007;129(49):15156-63. Epub Nov. 17, 2007.
Geoghegan, et al. Site-directed conjugation of nonpeptide groups to peptides and proteins via periodate oxidation of a 2-amino alcohol. Application to modification at N-terminal serine. Bioconjug Chem. Mar.-Apr. 1992;3(2):138-46.
Gerard, et al. Chemokines and disease. Nat Immunol. Feb. 2001;2(2):108-15.
Gerotziafas, et al. Effect of the anti-factor Xa and anti-factor IIa activities of low-molecular-weight heparins upon the phases of thrombin generation. J Thromb Haemost. May 2007;5(5):955-62.
Giusti, et al. Somatic diversification of S107 from an antiphosphocholine to an anti-DNA autoantibody is due to a single base change in its heavy chain variable region. Proc Natl Acad Sci U S A. May 1987; 84(9):2926-30.
Goger, et al. Different affinities of glycosaminoglycan oligosaccharides for monomeric and dimeric interleukin-8: a model for chemokine regulation at inflammatory sites. Biochemistry. Feb. 5, 2002;41(5):1640-6.
Gololobov, et al. Sixty years of staudinger reaction. Tetrahedron. 1981; 37(3):437-472.
Gololobov. Recent advances in the staudinger reaction. 1992; 48(8):1353-1406.
Goodman, et al. The Pharmacological Basis of Therapeutics. Tenth edition, McGraw Hill, 2001.
Green, et al. Antigen-specific human monoclonal antibodies from mice engineered with human Ig heavy and light chain YACs. Nat Genet. May 1994; 7(1):13-21.
Greene, et al. Protective Groups in Organic Synthesis. Published by John Wiley and Sons. 1999; pp. 67-74.
Griffith, MJ. Kinetics of the heparin-enhanced antithrombin III/thrombin reaction. Evidence for a template model for the mechanism of action of heparin. J Biol Chem. Jul. 10, 1982;257(13):7360-5.
Grubbs, R. H. Handbook of Metathesis, 1st ed. (vol. 3, sec. 3.3.5, pp. 98-103); Wiley-VCH: Weinheim, Germany, 2003.
Gussow, et al. Humanization of monoclonal antibodies. Methods Enzymol. 1991; 203:99-121.
Habeeb, A. F. Determination of free amino groups in proteins by trinitrobenzenesulfonic acid. Anal Biochem. Mar. 1966;14(3):328-36.
Habuchi, et al. Enzymatic synthesis of chondroitin sulfate E by N-acetylgalactosamine 4-sulfate 6-O-sulfotransferase purified from squid cartilage. An Bio. 2002; 310(2):129-136.
Hang, et al. Ketone isosteres of 2-N-acetamidosugars as substrates for metabolic cell surface engineering. J Am Chem Soc. Feb. 14, 2001;123(6):1242-3.
Hart, et al. Cycling of O-linked-N-acetylglucosamine on nucleocytoplasmic proteins. Nature, Apr. 26, 2007, vol. 446, No. 7139, pp. 1017-1022, entire document.
Haugland, Richard P. Handbook of fluorescent probes and research products. Molecular Probes, Inc; 9th edition. 2002.
Hirsh, et al. Heparin and low-molecular-weight heparin: mechanisms of action, pharmacokinetics, dosing considerations, monitoring, efficacy, and safety. Chest. Nov. 1998;114(5 Suppl):489S-510S.
Holm, et al. Functional mapping and single chain construction of the anti-cytokeratin 8 monoclonal antibody TS1. Mol Immunol. Feb. 2007;44(6):1075-84.
Holt, et al. Sugar codes for axons? Neuron. Apr. 21, 2005;46(2):169-72.
Hong, et al. Highly active water-soluble olefin metathesis catalyst. J Am Chem Soc. Mar. 22, 2006;128(11):3508-9.
Hu, et al. Divergent synthesis of 48 heparan sulfate-based disaccharides and probing the specific sugar-fibroblast growth factor-1 interaction. J Am Chem Soc. Dec. 26, 2012;134(51):20722-7. doi: 10.1021/ja3090065. Epub Dec. 14, 2012.
Hu, et al. Synthesis of 3-O-sulfonated heparan sulfate octasaccharides that inhibit the herpes simplex virus type 1 host-cell interaction. Nat Chem. Jun. 19, 2011;3(7):557-63. doi: 10.1038/nchem.1073.
Hue, et al. Role of fructose 2,6-biphosphate in the control of glycolysis in mammalian tissues. Biochem. J, Jul. 15, 1987, vol. 245, No. 2,313-324, entire document.
Huisgen, R. in 1,3-Dipolar Cycloaddition Chemistry, (1984) Ed. Padwa, A., Wiley, New York, p. 1-176.
Huse, et al. Generation of a large combinatorial library of the immunoglobulin repertoire in phage lambda. Science. Dec. 8, 1989;246(4935):1275-81.
Immunobiology for life scientists (Wiley, Ed. Eales, p. 14, 2003.

(56) References Cited

OTHER PUBLICATIONS

International preliminary report on patentability dated Nov. 29, 2006 for PCT Application No. US2005/018906.
International search report and written opinion dated Dec. 3, 2010 for PCT Application No. US2010/043256.
International search report dated Jan. 30, 2014 for PCT Application No. US2013/055606.
International search report dated Mar. 10, 2006 for PCT Application No. US2005/018906.
Ito, et al. Structural characterization of the epitopes of the monoclonal antibodies 473HD, CS-56, and MO-225 specific for chondroitin sulfate D-type using the oligosaccharide library. Glycobiology. Jun. 2005;15(6):593-603.
Iyer, et al. Design and synthesis of hyaluronan-mimetic Gemini disaccharides. Tetrahedron (2003) 59:631-638.
Jacquinet, et al. Multigram syntheses of the disaccharide repeating units of chondroitin 4- and 6-sulfates. Carbohydr-Res. Dec. 31, 1998; 314(3-4): 283-8.
Jacquinet, J. Synthesis of the methyl glycosides of the repeating units of chondroitin 4- and 6-sulfate. Carb. Res. (1990) 199:153-181.
Janssen, et al. 4-Iodoveratrole. Org. Synth. 1963; 4: 547.
Jencks. Studies on the Mechanism of Oxime and Semicarbazone Formation. J. Am. Chem. Soc. 1959; 81(2): 475-481.
Jewett, et al. Cu-free click cycloaddition reactions in chemical biology. Chem Soc Rev. Apr. 2010;39(4):1272-9.
Kalovidouris, et al. A role for fucose a (1-2) galactose carbohydrates in neuronal growth. J. Am. Chem. Soc. 2005; 127:1340-1341.
Kanai, et al. Varying the size of multivalent ligands: The dependence of Concanavalin A inhibition on neoglycopolymer length. J. Am. Chem. Soc. 1997; 119:9931-9932.
Kang, et al. O-GlcNAc protein modification in cancer cells increases in response to glucose deprivation through glycogen degradation. J Biol Chem, Dec. 11, 2009, vol. 284, No. 50, pp. 34777-34784, entire document.
Karst, et al. Chemical synthesis of β-D-GlcpA(2SO4)-(1->3)-D-GalpNAc(6SO4), the disaccharide repeating unit of shark cartilage chondroitin sulfate D, and of its methyl Γ-D-glycoside derivative. J. Chem. Soc. Perkin Trans. 2000; 1:2709-2717.
Karst, et al. Stereocontrolled total syntheses of shark cartilage chondroitin sulfate D-related tetra- and hexasaccharide methyl glycosides. Eur. J. Org. Chem. 2002; 815-825.
Katzung. Basic and Clinical Pharmacology. Ninth edition, McGraw Hill, 20037ybg.
Khidekel, et al. A Chemoenzymatic Approach toward the Rapid and Sensitive Detection of O-GlcNAc Posttranslational Modifications. J. Am. Chem. Soc. 2003; 125(52):16162-16163.
Kiessling, et al. Synthetic multivalent ligands in the exploration of cell-surface interactions. Curr Opin Chem Biol. Dec. 2000;4(6):696-703.
Kim, et al. Perspectives on the significance of altered glycosylation of glycoproteins in cancer. Glycoconj J. Aug. 1997;14(5):569-76.
Kinoshita, et al. Isolation and structural determination of novel sulfated hexasaccharides from squid cartilage chondroitin sulfate E that exhibits neuroregulatory activities. Biochemistry. Oct. 23, 2001;40(42):12654-65.
Kitagawa, et al. Developmental regulation of the sulfation profile of chondroitin sulfate chains in the chicken embryo brain. J Biol Chem. Dec. 12, 1997;272(50):31377-81.
Kitaura, et al. Molecular cloning of human eotaxin, an eosinophil-selective CC chemokine, and identification of a specific eosinophil eotaxin receptor, CC chemokine receptor 3. J Biol Chem. Mar. 29, 1996;271(13):7725-30.
Kohler, et al. Continuous cultures of fused cells secreting antibody of predefined specificity. Nature. Aug. 7, 1975;256(5517):495-7.
Kolonko, et al. General synthetic route to cell-permeable block copolymers via ROMP. J Am Chem Soc. Jun. 3, 2009;131(21):7327-33. doi: 10.1021/ja809284s.
Koshiishi, et al. Analysis of chondroitin sulfate/dermatan sulfate chains in rat peritoneal resident macrophages. J. Biol. Pharm. Bull. 1993; 16:307-308.
Kozbor, et al. The production of monoclonal antibodies from human lymphocytes. Immunology Today. 1983; 4:72-79.
Lee, et al. End-functionalized glycopolymers as mimetics of chondroitin sulfate proteoglycans. Chem Sci. Sep. 1, 2010;1(3):322-325.
Lee, et al. Expression of blood-group antigen A—a favorable prognostic factor in non-small-cell lung cancer. N Engl J Med. Apr. 18, 1991;324(16):1084-90.
Lewis, et al. Click chemistry in situ: acetylcholinesterase as a reaction vessel for the selective assembly of a femtomolar inhibitor from an array of building blocks. Angew Chem Int Ed Engl. Mar. 15, 2002;41(6):1053-7.
Li, et al. 1,3-Dipolar cycloaddition of azides with electron-deficient alkynes under mild condition in water. Tetrahedron Letters. 2004; 45(15):3143-3146.
Li, et al. Structure of the antithrombin-thrombin-heparin ternary complex reveals the antithrombotic mechanism of heparin. Nat Struct Mol Biol. Sep. 2004;11(9):857-62. Epub Aug. 15, 2004.
Liang, et al. Glycan array: a powerful tool for glycomics studies. Expert Rev Proteomics. Dec. 2009;6(6):631-45. doi: 10.1586/epr.09.82.
Lohman, et al. Synthesis of iduronic acid building blocks for the modular assembly of glycosaminoglycans. J Org Chem. Sep. 19, 2003;68(19):7559-61.
Lortat-Jacob, et al. Structural diversity of heparan sulfate binding domains in chemokines. Proc Natl Acad Sci U S A. Feb. 5, 2002;99(3):1229-34.
Lu, et al. Differential induction of glioblastoma migration and growth by two forms of pleiotrophin. J Biol Chem. Jul. 22, 2005;280(29):26953-64. Epub May 20, 2005.
Lucas, et al. Synthesis of heparin-like pentamers containing "opened" uronic acid moieties. Tetrahedron. 1990; 46:8207-8228.
Lynn, et al. Water-Soluble Ruthenium Alkylidenes: Synthesis, Characterization, and Application to Olefin Metathesis in Protic Solvents. J. Am. Chem. Soc. 2000; 122(28):6601-6609.
MacCallum, et al. Antibody-antigen interactions: contact analysis and binding site topography. J Mol Biol. Oct. 11, 1996;262(5):732-45.
Mackman, et al. Triggers, targets and treatments for thrombosis. Nature. Feb. 21, 2008;451(7181):914-8. doi: 10.1038/nature06797.
Maeda, et al. The binding of chondroitin sulfate to pleiotrophin/heparin-binding growth-associated molecule is regulated by chain length and oversulfated structures. J Biol Chem. Feb. 24, 2006;281(8):4894-902. Epub Dec. 22, 2005.
Maehr, et al. Synthetic (S)-5-(benzoyloxy)-6-oxohexanoic acid ethyl ester and [S,S-(E)-3-(hydroxymethyl)oxiranebutanoic acid methyl ester, important synthons for leukotrienes B4 and A4, from D-arabinose. J. Org. Chem., 1988, 53 (4), pp. 832-836.
Maggio (Immunoenzyme technique I, CRC press 1980, pp. 186-187).
Mahal, et al. Engineering chemical reactivity on cell surfaces through oligosaccharide biosynthesis. Science. May 16, 1997;276(5315):1125-8.
Manimala, et al. High-throughput carbohydrate microarray analysis of 24 lectins.Angew. Chem. 2006;118:3689-3692.
Manimala, et al. High-throughput carbohydrate microarray profiling of 27 antibodies demonstrates widespread specificity problems. Glycobiology. Aug. 2007;17(8):17C-23C. Epub May 4, 2007.
Mariuzza, et al. The structural basis of antigen-antibody recognition. Annu Rev Biophys Biophys Chem. 1987;16:139-59.
Marra, et al. Synthesis of disaccharide fragments of dermatan sulfate. Carb. Res. 1989; 195:39-50.
Marsh, et al. Signal transduction events mediated by the BDNF receptor gp145trkB in primary hippocampal pyramidal cell culture. J Neurosci. Oct. 1993;13(10):4281-92.
Martin, et al. Structural and functional analysis of the RANTES-glycosaminoglycans interactions. Biochemistry. May 29, 2001;40(21):6303-18.
Martindale. The Extra Pharmacopoeia. 32nd Edition, The Pharmaceutical Press, London, 1999.

(56) References Cited

OTHER PUBLICATIONS

Mattaini, et al. Cancer glycosylation to adapt to stress. Science, Aug. 24, 2012, vol. 337, No. 6097, pp. 925-926, entire document.
McCabe, et al. Passive avoidance training increases fucose incorporation into glycoproteins in chick forebrain slices in vitro. Neurochemical research 10.8 (1985): 1083-1095.
Menard, et al. Generation of monoclonal antibodies reacting with normal and cancer cells of human breast. Cancer Res. Mar. 1983;43(3):1295-300.
Meuleman, et al. Antifactor Xa activity and antithrombotic activity in rats of structural analogues of the minimum antithrombin III binding sequence: discovery of compounds with a longer duration of action than of the natural pentasaccharide. Semin Thromb Hemost. 1991;17 Suppl 1:112-7.
Miyake, et al. Correlation of expression of H/Le(y)/Le(b) antigens with survival in patients with carcinoma of the lung. N Engl J Med. Jul. 2, 1992;327(1):14-8.
Mizuguchi, et al. Chondroitin proteoglycans are involved in cell division of Caenohabditis elegans. Nature. 2003; 423:443-448.
Moon, et al. Regeneration of CNS axons back to their target following treatment of adult rat brain with chondroitinase ABC. Nat Neurosci. May 2001;4(5):465-6.
Morissette, et al. High-throughput crystallization: polymorphs, salts, co-crystals and solvates of pharmaceutical solids. Adv Drug Deliv Rev. Feb. 23, 2004;56(3):275-300.
Murrey, et al. Identification of the plasticity-relevant fucose-alpha(1-2)-galactose proteome from the mouse olfactory bulb. Biochemistry. Aug. 4, 2009;48(30):7261-70. doi: 10.1021/bi900640x.
Murrey, et al. Protein fucosylation regulates synapsin Ia/Ib expression and neuronal morphology in primary hippocampal neurons. Proc Nail Acad Sci U S A. Jan. 3, 2006;103(1):21-6. Epub Dec. 22, 2005.
Nadanaka, et al. Characteristic hexasaccharide sequences in octasaccharides derived from shark cartilage chondroitin sulfate D with a neurite outgrowth promoting activity. J. Biol. Chem. 1998; 273:3296-3307.
Nandini, et al. Structural and functional characterization of oversulfated chondroitin sulfate/dermatan sulfate hybrid chains from the notochord of hagfish. Neuritogenic and binding activities for growth factors and neurotrophic factors. J Biol Chem. Dec. 3, 2004;279(49):50799-809.
Notice of allowance dated Mar. 5, 2010 for U.S. Appl. No. 11/751,863.
Notice of allowance dated Aug. 6, 2009 for U.S. Appl. No. 11/140,618.
Notice of Allowance dated Aug. 15, 2014 for U.S. Appl. No. 12/315,168.
Notice of allowance dated Aug. 22, 2012 for U.S. Appl. No. 12/511,944.
Notice of allowance dated Sep. 16, 2013 for U.S. Appl. No. 11/751,880.
Notice of allowance dated Sep. 26, 2014 for U.S. Appl. No. 12/511,941.
Office action date Jun. 2, 2011 for JP Application No. 2007-515442 (in Japanese with English translation).
Office action dated Jan. 2, 2013 for U.S. Appl. No. 11/751,880.
Office action dated Jan. 6, 2011 for U.S. Appl. No. 12/511,941.
Office action dated Feb. 6, 2009 for U.S. Appl. No. 11/751,863.
Office action dated Feb. 9, 2009 for U.S. Appl. No. 11/140,618.
Office action dated Feb. 15, 2007 for U.S. Appl. No. 11/140,618.
Office action dated Feb. 16, 2011 for U.S. Appl. No. 11/751,880.
Office action dated Mar. 28, 2012 for U.S. Appl. No. 11/751,880.
Office action dated Apr. 11, 2013 for U.S. Appl. No. 12/843,758.
Office action dated May 10, 2012 for U.S. Appl. No. 12/315,168.
Office action dated Jun. 5, 2008 for U.S. Appl. No. 11/140,618.
Office action dated Jun. 19, 2014 for U.S. Appl. No. 12/511,941.
Office action dated Jun. 24, 2010 for U.S. Appl. No. 12/511,941.
Office action dated Jun. 27, 2012 for U.S. Appl. No. 12/843,758.
Office action dated Sep. 1, 2010 for U.S. Appl. No. 11/751,880.
Office action dated Sep. 28, 2007 for U.S. Appl. No. 11/140,618.
Office action dated Sep. 30, 2014 for U.S. Appl. No. 12/843,758.
Office action dated Oct. 21, 2011 for U.S. Appl. No. 11/751,880.
Office action dated Oct. 23, 2009 for U.S. Appl. No. 11/751,863.
Office action dated Oct. 31, 2011 for U.S. Appl. No. 12/315,168.
Office action dated Dec. 21, 2011 for U.S. Appl. No. 12/511,944.
Ohno, et al. Synthesis of a well-defined glycopolymer by atom transfer radical polymerization. Journal of Polymer Science Part A: Polymer Chemistry. Oct. 1998; 36(14): 2473-2481.
Orgueira, et al. Modular synthesis of heparin oligosaccharides. Chemistry. Jan. 3, 2003;9(1):140-69.
Ori, et al. A systems biology approach for the investigation of the heparin/heparan sulfate interactome. J Biol Chem. Jun. 3, 2011;286(22):19892-904. doi: 10.1074/jbc.M111.228114. Epub Mar. 30, 2011.
Padwa. Comprehensive Organic Synthesis, vol. 4, (1991) Ed. Trost, B. M., Pergamon, Oxford, p. 1069-1109.
Pan, et al. Oversulfated chondroitin sulfate is not the sole contaminant in heparin. Nat Biotechnol. Mar. 2010;28(3):203-7; author reply 203-7. doi: 10.1038/nbt0310-203.
Pathania, et al. Opportunities in discovery and delivery of anticancer drugs targeting mitochondria and cancer cell metabolism. Advanced Drug Delivery Reviews, Nov. 30, 2009, vol. 61, No. 14, pp. 1250-1275, entire document.
Peracaula, et al. Altered glycosylation pattern allows the distinction between prostate-specific antigen (PSA) from normal and tumor origins. Glycobiology. Jun. 2003;13(6):457-70. Epub Jan. 3, 2003.
Petitou, et al. A synthetic antithrombin III binding pentasaccharide is now a drug! What comes next? Angew Chem Int Ed Engl. Jun. 14, 2004;43(24):3118-33.
Petitou, et al. Synthesis of thrombin-inhibiting heparin mimetics without side effects. Nature. Apr. 1, 1999;398(6726):417-22.
Plaas, et al. Glycosaminoglycan sulfation in human osteoarthritis. Disease-related alterations at the non-reducing termini of chondroitin and dermatan sulfate. J Biol Chem. May 15, 1998;273(20):12642-9.
Pohle, et al. Incorporation of [3H]fucose in rat hippocampal structures after conditioning by perforant path stimulation and after LTP-producing tetanization. Brain research 1987; 410(2): 245-56.
Powell, et al. Generating heparan sulfate saccharide libraries for glycomics applications. Nat Protoc. May 2010;5(5):821-33. doi: 10.1038/nprot.2010.17. Epub Apr. 8, 2010.
Pratt, et al. Princples of Drug Action. Third edition, Churchill Livingston, New York, 1990.
Proudfoot, et al. Glycosaminoglycan binding and oligomerization are essential for the in vivo activity of certain chemokines. Proc Natl Acad Sci U S A. Feb. 18, 2003;100(4):1885-90. Epub Feb. 5, 2003.
Qin, et al. The chemokine receptors CXCR3 and CCR5 mark subsets of T cells associated with certain inflammatory reactions. J Clin Invest. Feb. 15, 1998;101(4):746-54.
Rabuka, et al. Hierarchical assembly of model cell surfaces: synthesis of mucin mimetic polymers and their display on supported bilayers. J Am Chem Soc. May 2, 2007;129(17):5462-71. Epub Apr. 11, 2007.
Ravida, et al. Synthesis of glycosyl phosphates from 1,2-orthoesters and application to in situ glycosylation reactions. Org Lett. Apr. 27, 2006;8(9):1815-8.
Rawat, et al. Neuroactive chondroitin sulfate glycomimetics. J Am Chem Soc. Mar. 12, 2008;130(10):2959-61. doi: 10.1021/ja709993p. Epub Feb. 15, 2008.
Remington's Pharmaceutical Sciences, 20th Ed., Lippincott Williams & Wilkins., 2000.
Rexach, et al. Chemical approaches to understanding O-GlcNAc glycosylation in the brain. Nat Chem Biol. Feb. 2008;4(2):97-106. doi: 10.1038/nchembio.68.
Rexach, et al. Quantification of O-glycosylation stoichiometry and dynamics using resolvable mass tags. Nat Chem Biol. Sep. 2010;6(9):645-51. doi: 10.1038/nchembio.412. Epub Jul. 25, 2010.
Rhodes, et al. Chondroitin sulphate proteoglycans: preventing plasticity or protecting the CNS? J Anat. Jan. 2004;204(1):33-48.
Richards, et al. Probing bacterial-toxin inhibition with synthetic glycopolymers prepared by tandem post-polymerization modifica-

(56) References Cited

OTHER PUBLICATIONS tion: role of linker length and carbohydrate density. Angew Chem Int Ed Engl. Jul. 27, 2012;51(31):7812-6. doi: 10.1002/anie. 201202945. Epub Jun. 19, 2012.

Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.

Rudikoff, et al. Single amino acid substitution altering antigen-binding specificity. Proc Natl Acad Sci U S A. Mar. 1982;79(6):1979-83.

Sandson, et al. The potential application of cyclo-oxygenase type 2 inhibitors to Alzheimer's disease. Expert Opin Investig Drugs. Apr. 1998;7(4):519-26.

Sanford, et al. A Versatile Precursor for the Synthesis of New Ruthenium Olefin Metathesis Catalysts. Organometallics. 2001; 20 (25): 5314-5318.

Saxon, et al. Investigating cellular metabolism of synthetic azidosugars with the Staudinger ligation. J Am Chem Soc. Dec. 18, 2002;124(50):14893-902.

Scholl, et al. Synthesis and activity of a new generation of ruthenium-based olefin metathesis catalysts coordinated with 1,3-dimesityl-4,5-dihydroimidazol-2-ylidene ligands. Org Lett. Sep. 23, 1999;1(6):953-6.

Schroder, et al. Screening and prostate-cancer mortality in a randomized European study. N Engl J Med. Mar. 26, 2009;360(13):1320-8. doi: 10.1056/NEJMoa0810084. Epub Mar. 18, 2009.

Schuda, et al. A facile method for the oxidative removal of benzyl ethers: the oxidation of benzyl ethers to benzoates by ruthenium tetraoxide. Tetrahedron Letters. 1983; 24(36): 3829-3830.

Schuda, et al. The synthesis of dl-Coriolin. Tetrahedron Letters. 1983; 24(40): 4267-4270.

Seo, et al. Click chemistry to construct fluorescent oligonucleotides for DNA sequencing. J Org Chem. Jan. 24, 2003;68(2):609-12.

Shao, et al. Unprotected Peptides as Building Blocks for the Synthesis of Peptide Dendrimers with Oxime, Hydrazone, and Thiazolidine Linkages. J. Am. Chem. Soc. 1995; 117(14):3893-3899.

Shaw, et al. The X-ray structure of RANTES: heparin-derived disaccharides allows the rational design of chemokine inhibitors. Structure. Nov. 2004;12(11):2081-93.

Sheng, et al. Tunable heparan sulfate mimetics for modulating chemokine activity. J Am Chem Soc. Jul. 31, 2013;135(30):10898-901. doi: 10.1021/ja4027727. Epub Jul. 23, 2013.

Shi, et al. Luteolin sensitizes tumor necrosis factor-alpha-induced apoptosis in human tumor cells. Oncogene. Oct. 7, 2004;23(46):7712-21.

Shipp, et al. Profiling the sulfation specificities of glycosaminoglycan interactions with growth factors and chemotactic proteins using microarrays. Chem Biol. Feb. 2007;14(2):195-208.

Shirayev, et al. Synthesis of Novel Adamantylalkoxyurea Derivatives from 2-(1-Adamantylimino)-1,3-oxathiolane. Journal of Synthetic Organic Chemistry. 1997; 1:38-40.

Siuzdak, Gary. Mass spectrometry for biotechnology. Academic Press, 1996.

Skinner, et al. The 2.6 A structure of antithrombin indicates a conformational change at the heparin binding site. J Mol Biol. Feb. 28, 1997;266(3):601-9.

Smetsers, et al. Human Single-Chain Antibodies Reactive with Native Chondroitin Sulfate Detect Chondroitin Sulfate Alterations in Melanoma and Psoriasis. J Invest Dermatol. Mar. 2004;122(3):707-16.

Smith, et al. Use of glycan microarrays to explore specificity of glycan-binding proteins. Methods Enzymol. 2010;480:417-44. doi: 10.1016/S0076-6879(10)80033-3.

Sotogaku, et al. Activation of phospholipase C pathways by a synthetic chondroitin sulfate-E tetrasaccharide promotes neurite outgrowth of dopaminergic neurons. J Neurochem. Oct. 2007;103(2):749-60.

Staudinger, et al. New organic compounds of phosphorus. III. Phosphinemethylene derivatives and phosphinimines Helv. Chim. Acta. 1919; 2: 635-646.

Stevens, et al. Synthesis of chondroitin sulfate E glycosaminoglycan onto p-nitrophenyl-β-d-xyloside and its localization to the secretory granules of rat serosal mast cells and mouse bone marrow-derived mast cells. JBC.1983; 258;5977-5984.

Su, et al. Human H+ ATPase a4 subunit mutations cuasing renal tubular acidosis reveal a role for interaction with phosphofructokinase-1. Am J Physiol, Oct. 2008, vol. 295, No. 4, pp. F950-F958, entire document.

Suchman, et al. Diagnostic uses of the activated partial thromboplastin time and prothrombin time. Ann Intern Med. Jun. 1986;104(6):810-6.

Sugahara, et al. Recent advances in the structural biology of chondroitin sulfate and dermatan sulfate. Curr. Opin. Chem. Biol. 2003; 13:612-620.

Sugahara, et al. Structural studies on the chondroitinase ABC-resistant sulfated tetrasaccharides isolated from various chondroitin sulfate isomers. Carbohydr Res. Mar. 4, 1994;255:145-63.

Suzuki, et al. Formation of three types of disulfated disaccharides from chondroitin sulfates by chondroitinase digestion. J Biol Chem. Apr. 10, 1968;243(7):1543-50.

Tabeur, et al. Oligosaccharides corresponding to the regular sequence of heparin: chemical synthesis and interaction with FGF-2. Bioorg Med Chem. Sep. 1999;7(9):2003-12.

Takagaki, et al. Domain structure of chondroitin sulfate E octasaccharides binding to type V collagen. J Biol Chem. Mar. 15, 2002;277(11):8882-9.

Tamura, et al. A regio- and stereoselective synthesis of 4-O-sulfated chondroitin di- and tetrasaccharides based on the strategy designed for the elongation of the repeating unit. Bioorg. Medic. Chem. Lett. 1995; 5:1351-1354.

Tamura, et al. Synthetic approach towards sulfated chondroitin di-, tri- and tetrasaccharides corresponding to the repeating unit. Carb. Res. 1998; 305:43-63.

Taylor, et al. A colorimetric method for the quantitation of uronic acids and a specific assay for galacturonic acid. Anal Biochem. Feb. 14, 1992;201(1):190-6.

The Merck Manual of Diagnosis and Therapy. 17th ed. Merck Research Laboratories. 1999; 1341-1359.

Tiunova, et al. Two critical periods of protein and glycoprotein synthesis in memory consolidation for visual categorization learning in chicks. doi: 10.1101/lm. Learning & Memory 4.5 (1998): 401-410.

Tornoe, et al. Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Tsuchida, et al. Appican, the proteoglycan form of the amyloid precursor protein, contains chondroitin sulfate E in the repeating disaccharide region and 4-O-sulfated galactose in the linkage region. J. Biol. Chem. 2001; 276:37155-37160.

Tully, et al. A chondroitin sulfate small molecule that stimulates neuronal growth. J. Am. Chem. Soc. 2004; 126:7736-7737.

Tully, et al. Discovery of a TNF-alpha antagonist using chondroitin sulfate microarrays. J Am Chem Soc. Jun. 21, 2006;128(24):7740-1.

Urbano, et al. Effects of overexpression of the liver subunit of 6-phosphofructo-1-kinase on the metabolism of a culture mammalian cell line. Biochem J, Dec. 15, 2000, vol. 352, Pt. 3, pp. 921-927, entire document.

Van Boeckel, et al. Synthesis of a potent antithrombin activating pentasaccharide: a new heparin-like fragment containing two 3-O-sulphated glucosamines. Tetrahedron Lett 1988; 29: 803-806.

Vippagunta, et al. Crystalline solids. Adv Drug Deliv Rev. May 16, 2001;48(1):3-26.

Viskov, et al. Description of the chemical and pharmacological characteristics of a new hemisynthetic ultra-low-molecular-weight heparin, AVE5026. J Thromb Haemost. Jul. 2009;7(7):1143-51. doi: 10.1111/j.1538-7836.2009.03447.x. Epub Apr. 27, 2009.

Volpi, N. Disaccharide mapping of chondroitin sulfate of different origins by high-performance capillary electrophoresis and high-performance liquid chromatography. Carbohyd. Polym. 2004; 55, 273-281.

(56) References Cited

OTHER PUBLICATIONS

Wan, et al. N-desulfated non-anticoagulant heparin inhibits leukocyte adhesion and transmigration in vitro and attenuates acute peritonitis and ischemia and reperfusion injury in vivo. Inflamm Res. Sep. 2002;51(9):435-43.
Wang, et al. Heparin's anti-inflammatory effects require glucosamine 6-O-sulfation and are mediated by blockade of L- and P-selectins. J Clin Invest. Jul. 2002;110(1):127-36.
Warkentin, et al. Heparin-induced thrombocytopenia in patients treated with low-molecular-weight heparin or unfractionated heparin. N Engl J Med. May 18, 1995;332(20):1330-5.
Winkler, et al. Changing the antigen binding specificity by single point mutations of an anti-p24 (HIV-1) antibody. J Immunol Oct. 15, 2000;165(8):4505-14.
Xu, et al. Chemoenzymatic synthesis of homogeneous ultralow molecular weight heparins. Science. Oct. 28, 2011;334(6055):498-501. doi: 10.1126/science.1207478.
Yamagata, et al. A monoclonal antibody that specifically recognizes a glucuronic acid 2-sulfate-containing determinant in intact chondroitin sulfate chain. J Biol Chem. Mar. 25, 1987;262(9):4146-52.
Yamagata, et al. Tissue variation of two large chondroitin sulfate proteoglycans (PG-M/versican and PG-H/aggrecan) in chick embryos. Anat Embryol (Berl). May 1993;187(5):433-44.
Yeung, et al. An essential role for the interferon-inducible, double-stranded RNA-activated protein kinase PKR in the tumor necrosis factor-induced apoptosis in U937 cells. Proc Natl Acad Sci U S A. Oct. 29, 1996;93(22):12451-5.
Yi, et al. Bacterial homologue of human blood group A transferase. J Am Chem Soc. Nov. 5, 2008;130(44):14420-1. doi: 10.1021/ja805844y. Epub Oct. 9, 2008.
Yi, et al. Phosphofructokinase 1 glycosylation regulatres cell growth and metabolism. Science, Aug. 24, 2012, vol. 337, No. 6097, pp. 975-980, entire document.
Yiu, et al. Glial inhibition of CNS axon regeneration. Nat Rev Neurosci. Aug. 2006;7(8):617-27.
Young, E. The anti-inflammatory effects of heparin and related compounds. Thromb Res. 2008;122(6):743-52. Epub Aug. 28, 2007.
Zhang, et al. DDQ-mediated oxidation of 4,6-O-methoxybenzylidene-protected saccharides in the presence of various nucleophiles: formation of 4-OH, 6-Cl, and 6-Br derivatives. J. Org. Chem. 1996; 61:2394-2400.
Zhang, et al. Oversulfated chondroitin sulfate: impact of a heparin impurity, associated with adverse clinical events, on low-molecular-weight heparin preparation. J Med Chem. Sep. 25, 2008;51(18):5498-501. doi: 10.1021/jm800785t.
Zhang, et al. Selection of tumor antigens as targets for immune attack using immunohistochemistry: protein antigens. Clin Cancer Res. Nov. 1998;4(11):2669-76.
Zheng, et al. Tracking N-acetyllactosamine on cell-surface glycans in vivo. Angew Chem Int Ed Engl. Apr. 26, 2011;50(18):4113-8. doi: 10.1002/anie.201100265. Epub Mar. 29, 2011.
Adang, et al. The reconstruction and expression of a Bacillus thuringiensis cryIIIA gene in protoplasts and potato plants. Plant Mol Biol. Mar. 1993;21(6):1131-45.
Armitage, et al. Molecular and biological characterization of a murine ligand for CD40. Nature. May 7, 1992;357(6373):80-2.
Ausubel, et al. Current Protocols in Molecular Biology, 1987.
Ausubel, et al. Short Protocols in Molecular Biology. 3rd Edition, John Wiley and Sons, 1999.
Baines, et al. Purification of immunoglobulin g (IgG). Methods Mol Biol. 1992;10:79-104. doi: 10.1385/0-89603-204-3:79.
Bambot, et al. Efficient total gene synthesis of 1.35-kb hybrid alpha-lytic protease gene using the polymerase chain reaction. PCR Methods Appl. Feb. 1993;2(3):266-71.
Bitter, et al. Expression and secretion vectors for yeast. Methods Enzymol. 1987;153:516-44.
Bradbury, et al. Chondroitinase ABC promotes functional recovery after spinal cord injury. Nature. Apr. 11, 2002;416(6881):636-40.
Bruggemann, et al. Production of human antibody repertoires in transgenic mice. Curr Opin Biotechnol. Aug. 1997;8(4):455-8.
Cairns, et al. Regulation of cancer cell metabolism. Nat Rev Cancer. Feb. 2011;11(2):85-95. doi: 10.1038/nrc2981.
Caldwell, et al. Nutrient sensor O-GlcNAc transferase regulates breast cancer tumorigenesis through targeting of the oncogenic transcription factor FoxM1. Oncogene. May 13, 2010;29(19):2831-42. doi: 10.1038/onc.2010.41. Epub Mar. 1, 2010.
Carter, et al. Humanization of an anti-p185HER2 antibody for human cancer therapy. Proc Natl Acad Sci U S A. May 15, 1992;89(10):4285-9.
Chalfie, et al. Green fluorescent protein as a marker for gene expression. Science. Feb. 11, 1994;263(5148):802-5.
Chaubard, et al. Chemoenzymatic probes for detecting and imaging fucose-α(1-2)-galactose glycan biomarkers.J Am Chem Soc. Mar. 14, 2012;134(10):4489-92. doi: 10.1021/ja211312u. Epub Feb. 29, 2012.
Chen, et al. TiProD: the Tissue-specific Promoter Database. Nucleic Acids Res. Jan. 1, 2006;34(Database issue):D104-7.
Clark. Antibody humanization: a case of the 'Emperor's new clothes'? Immunol Today. Aug. 2000;21(8):397-402.
Coligan, et al. Current Protocols in Immunology. John Wiley and Sons, 1991.
Dillon, et al. Use of polymerase chain reaction for the rapid construction of synthetic genes. Methods Mol Biol. 1993;15:263-8. doi: 10.1385/0-89603-244-2:263.
Eglitis, et al. Retroviral vectors for introduction of genes into mammalian cells. Biotechniques. Jul.-Aug. 1988;6(7):608-14.
Freshney. Culture of Animal Cells: A Manual of Basic Technique, 1987.
GenBank Accession No. U55762, pEGFP-N1 Vector Information. Gene 173 (1 Spec No), 33-38 (1996).
Gold, et al. Diversity of oligonucleotide functions. Annu Rev Biochem. 1995;64:763-97.
Gossen, et al. Tight control of gene expression in mammalian cells by tetracycline-responsive promoters. Proc Natl Acad Sci U S A. Jun. 15, 1992;89(12):5547-51.
Gramsbergen; A., "Clumsiness and disturbed cerebellar development: insights from animal experiments. Neural Plast. 2003;10(1-2)129-40.".
Griffiths, et al. Strategies for selection of antibodies by phage display. Curr Opin Biotechnol. Feb. 1998;9(1):102-8.
Haller, et al. In vitro selection of a 7-methyl-guanosine binding RNA that inhibits translation of capped mRNA molecules. Proc Natl Acad Sci U S A. Aug. 5, 1997;94(16):8521-6.
Harlow, et al. Antibodies: A Laboratory Manual, 1988.
Heim, et al. Engineering green fluorescent protein for improved brightness, longer wavelengths and fluorescence resonance energy transfer. Curr Biol. Feb. 1, 1996;6(2):178-82.
Ichiki, et al. Regulation of the expression of human C epsilon germline transcript. Identification of a novel IL-4 responsive element. J Immunol. Jun. 15, 1993;150(12):5408-17.
Jones, et al. Replacing the complementarity-determining regions in a human antibody with those from a mouse. Nature. May 29-Jun. 4, 1986;321(6069):522-5.
Kaufman, et al. Amplification and expression of sequences cotransfected with a modular dihydrofolate reductase complementary dna gene. J Mol Biol. Aug. 25, 1982;159(4):601-21.
Levine, et al. The control of the metabolic switch in cancers by oncogenes and tumor suppressor genes. Science. Dec. 3, 2010;330(6009):1340-4. doi: 10.1126/science.1193494.
Lynch, et al. Critical role of O-Linked β-N-acetylglucosamine transferase in prostate cancer invasion, angiogenesis, and metastasis. J Biol Chem. Mar. 30, 2012;287(14):11070-81. doi: 10.1074/jbc.M111.302547. Epub Jan. 24, 2012.
McPherson, et al. Methods in Enzymology: PCR 2: A Practical Approach. Academic Press, 1995.
Nolan, et al. Fluorescence-activated cell analysis and sorting of viable mammalian cells based on beta-D-galactosidase activity after transduction of *Escherichia coli* lacZ. Proc Natl Acad Sci U S A. Apr. 1988;85(8):2603-7.

(56) References Cited

OTHER PUBLICATIONS

O'Connor, et al. Humanization of an antibody against human protein C and calcium-dependence involving framework residues. Protein Eng. Apr. 1998;11(4):321-8.
Office action dated May 27, 2015 for U.S. Appl. No. 12/843,758.
Office action dated Dec. 3, 2015 for U.S. Appl. No. 14/147,446.
Possemato, et al. Functional genomics reveal that the serine synthesis pathway is essential in breast cancer. Nature. Aug. 18, 2011;476(7360):346-50. doi: 10.1038/nature10350.
Queen, et al. A humanized antibody that binds to the interleukin 2 receptor. Proc Natl Acad Sci U S A. Dec. 1989;86(24):10029-33.
Remington's Pharmaceutical Sicences. 18th Edition, 1990.
Riechmann, et al. Reshaping human antibodies for therapy. Nature. Mar. 24, 1988;332(6162):323-7.
Sambrook, et al. Molecular Cloning: A Laboratory Manual. 2nd Edition, 1989.
Scahill, et al. Expression and characterization of the product of a human immune interferon cDNA gene in Chinese hamster ovary cells. Proc Natl Acad Sci U S A. Aug. 1983;80(15):4654-8.
Sidorenko, et al. Comparison of metabolic flux distributions for MDCK cell growth in glutamine- and pyruvate-containing media. Biotechnol Prog. Mar.-Apr. 2008;24(2):311-20. doi: 10.1021/bp0702673. Epub Jan. 24, 2008.
Slawson, et al. O-GlcNAc signalling: implications for cancer cell biology. Nat Rev Cancer. Aug. 18, 2011;11(9):678-84. doi: 10.1038/nrc3114.
Sola-Penna, et al. Regulation of mammalian muscle type 6-phosphofructo-1-kinase and its implication for the control of the metabolism. IUBMB Life. Nov. 2010;62(11):791-6. doi: 10.1002/iub.393.
Southern, et al. Transformation of mammalian cells to antibiotic resistance with a bacterial gene under control of the SV40 early region promoter. J Mol Appl Genet. 1982;1(4):327-41.
Stauber, et al. Development and applications of enhanced green fluorescent protein mutants. Biotechniques. Mar. 1998;24(3):462-6, 468-71.
Steinberg. Protein gel staining methods: an introduction and overview. Methods Enzymol. 2009;463:541-63. doi: 10.1016/S0076-6879(09)63031-7.
Subramani, et al. Expression of the mouse dihydrofolate reductase complementary deoxyribonucleic acid in simian virus 40 vectors. Mol Cell Biol. Sep. 1981;1(9):854-64.
Taylor, et al. Glucose deprivation stimulates O-GlcNAc modification of proteins through up-regulation of O-linked N-acetylglucosaminyltransferase. J Biol Chem. Mar. 7, 2008;283(10):6050-7. doi: 10.1074/jbc.M707328200. Epub Jan. 3, 2008.
Urlaub, et al. Isolation of Chinese hamster cell mutants deficient in dihydrofolate reductase activity. Proc Natl Acad Sci U S A. Jul. 1980;77(7):4216-20.
Vander-Heiden, et al. Understanding the Warburg effect: the metabolic requirements of cell proliferation. Science. May 22, 2009;324(5930):1029-33. doi: 10.1126/science.1160809.
Verhoeyen, et al. Reshaping human antibodies: grafting an antilysozyme activity. Science. Mar. 25, 1988;239(4847):1534-6.
Wang, et al. A DNA aptamer which binds to and inhibits thrombin exhibits a new structural motif for DNA. Biochemistry. Mar. 2, 1993;32(8):1899-904.
Wilson, et al. A cloning of the B cell membrane protein CD22: a mediator of B-B cell interactions. J Exp Med. Jan. 1, 1991;173(1):137-46.
Wilson, et al. Genomic structure and chromosomal mapping of the human CD22 gene. J Immunol. Jun. 1, 1993;150(11):5013-24.
Wu, et al. Receptor-mediated in vitro gene transformation by a soluble DNA carrier system. J Biol Chem. Apr. 5, 1987;262(10):4429-32.
Zheng, et al. Lectin arrays for profiling cell surface carbohydrate expression. J Am Chem Soc. Jul. 20, 2005;127(28):9982-3.
Office action dated Apr. 22, 2016 for U.S. Appl. No. 14/450,192.
Office action dated Apr. 11, 2017 for U.S. Appl. No. 14/450,192.

\* cited by examiner

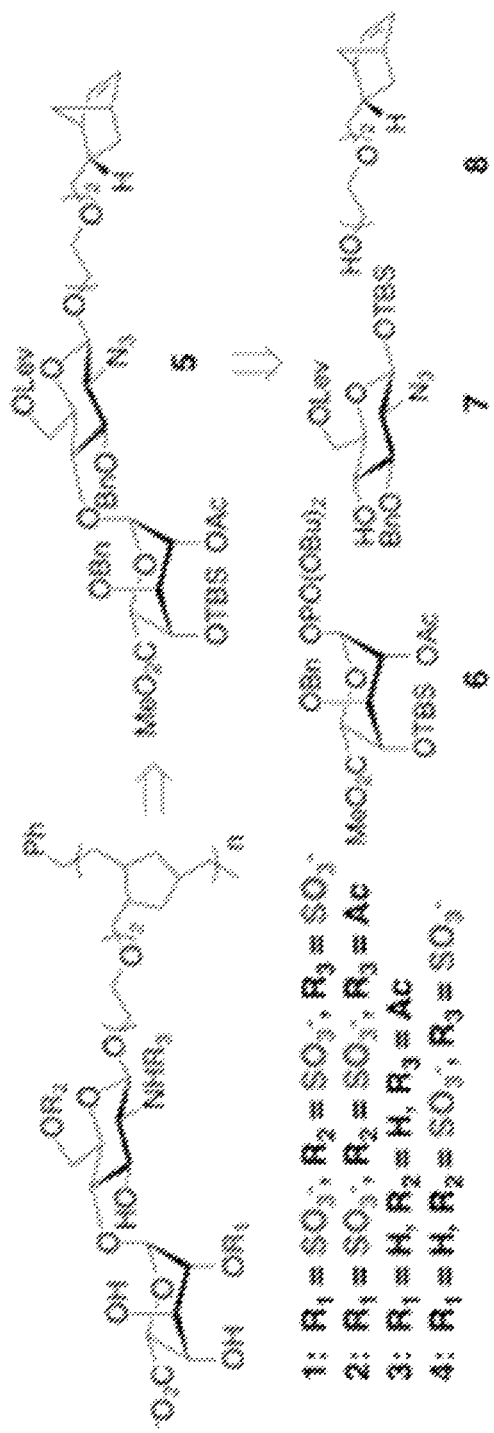
Fig. 1A
Fig. 1B

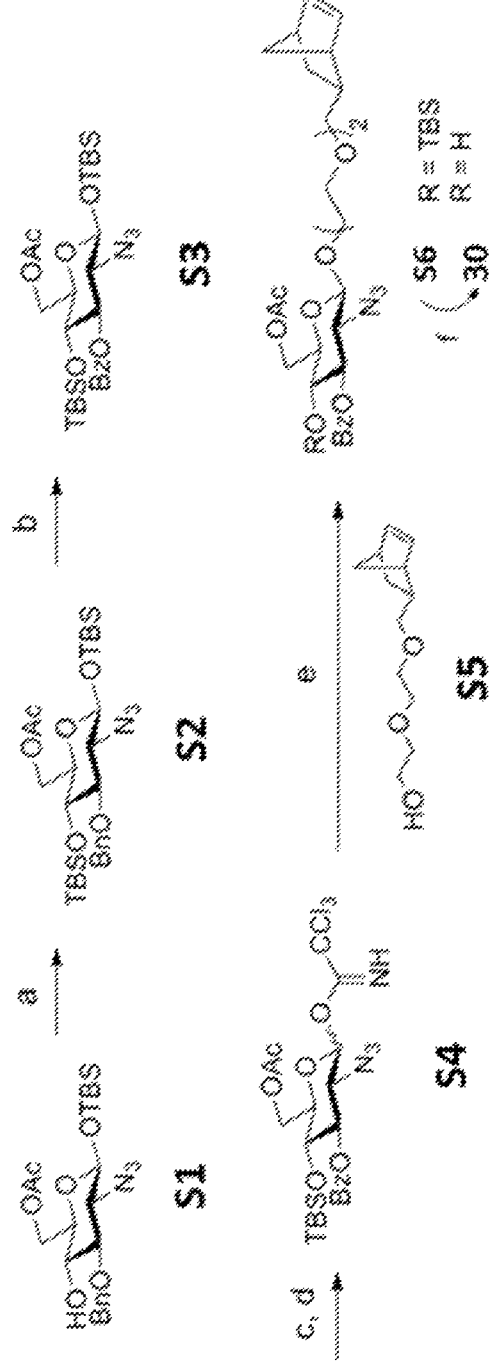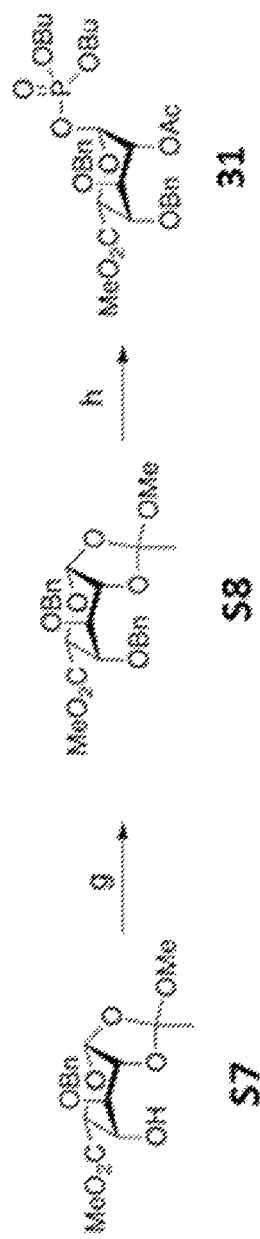
Fig. 10A
Fig. 10B

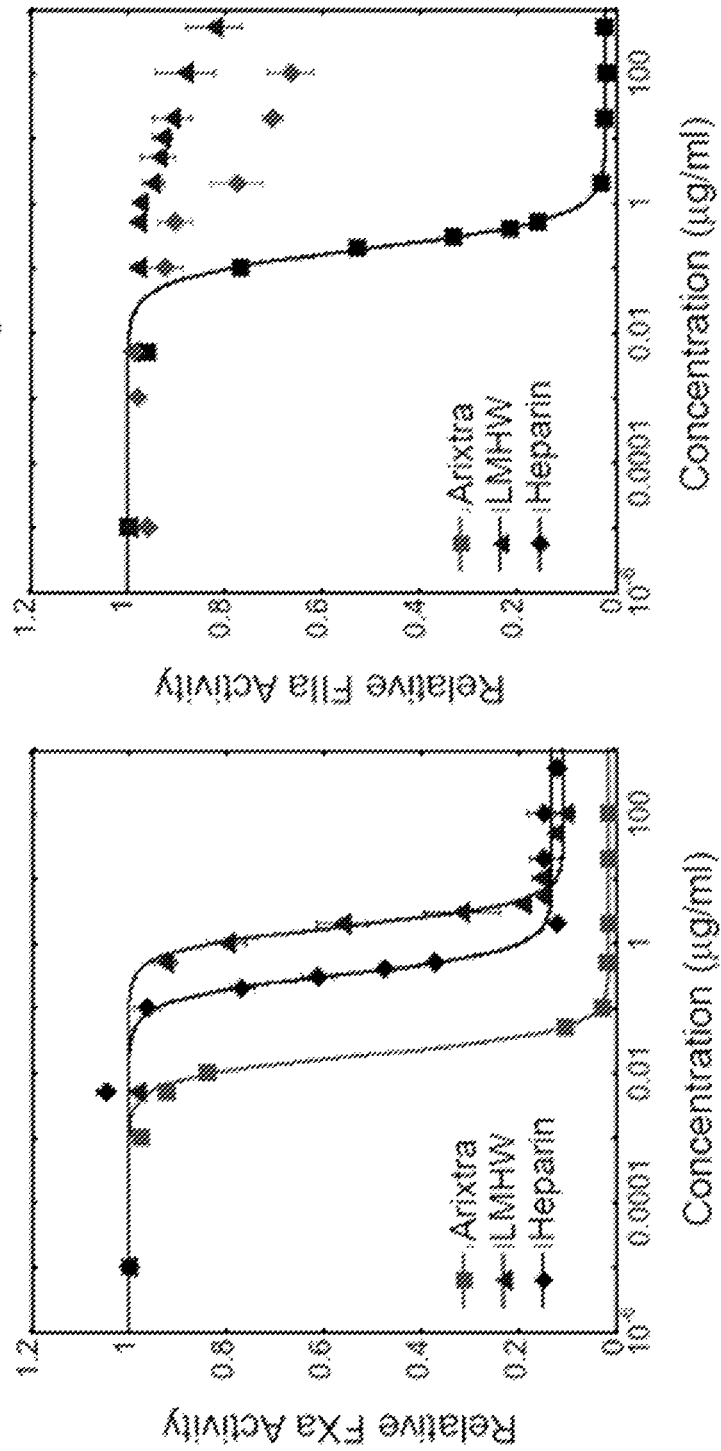

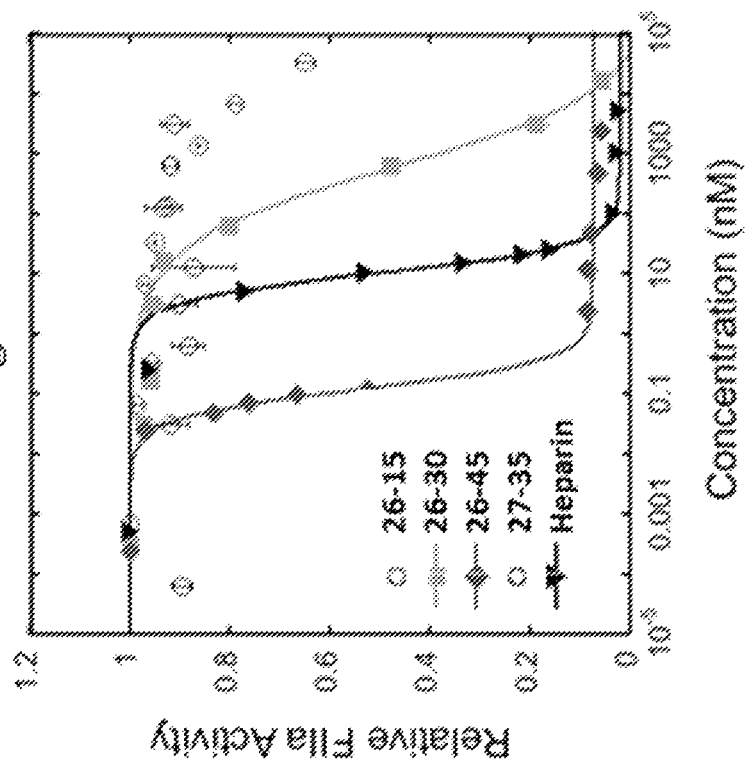
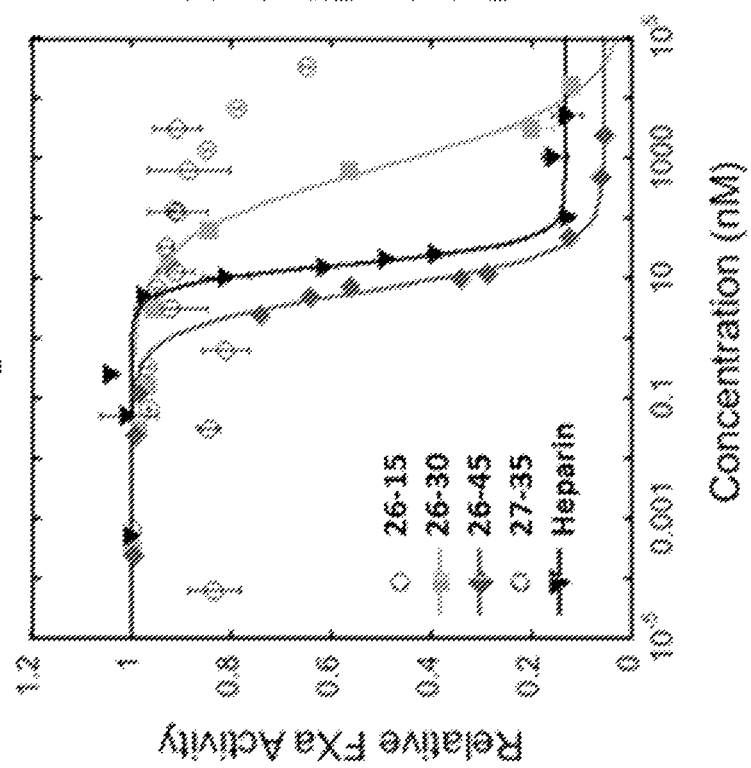

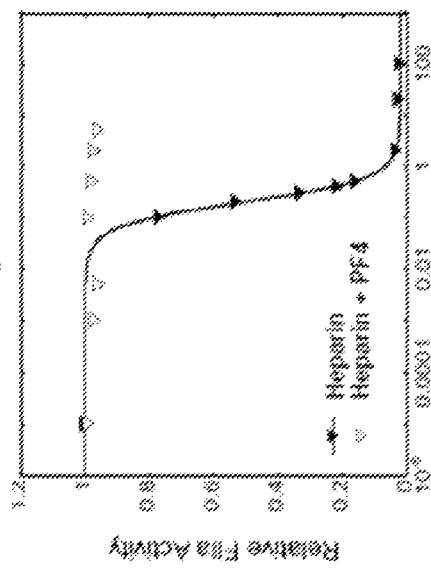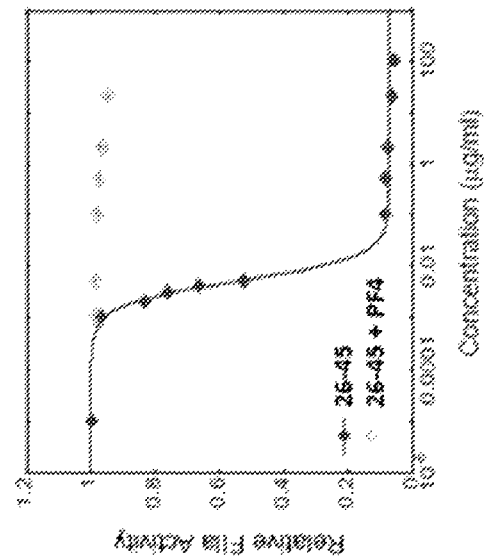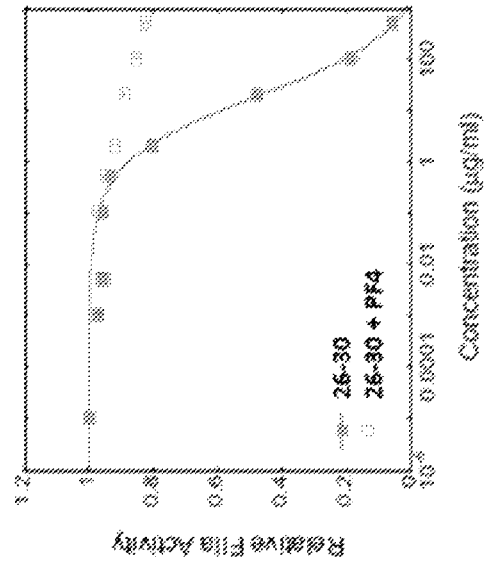

TAILORED GLYCOPOLYMERS AS ANTICOAGULANT HEPARIN MIMETICS

CROSS-REFERENCE

This application claims the benefit of U.S. Provisional Application No. 61/861,567, filed on Aug. 2, 2013, which application is incorporated herein by reference.

STATEMENT AS TO FEDERALLY SPONSORED RESEARCH

This invention was made with the support of the United States government under Contract number R01 GM093627 by the National Institutes of Health.

BACKGROUND OF THE INVENTION

Glycosaminoglycans, a ubiquitous class of sulfated polysacchrides, play a critical role in various physiological processes, such as development, wound healing, angiogenesis, cell division, inflammation and spinal cord injury. The complexity of this class of natural molecules has made correlating structure to function difficult. Synthetic glycopolymers with tunable properties may offer an alternative to natural molecules.

SUMMARY OF THE INVENTION

In one aspect, the present disclosure provides a glycopolymer comprising a plurality of repeating units, wherein each of the repeating units comprises a saccharide moiety (SA), a linking group (L) and a polymer backbone moiety (PB). The repeating units are optionally connected by one or more carbon-carbon double bonds, wherein the glycopolymer is of the formula:

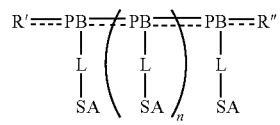

and the saccharide moiety is of the formula:

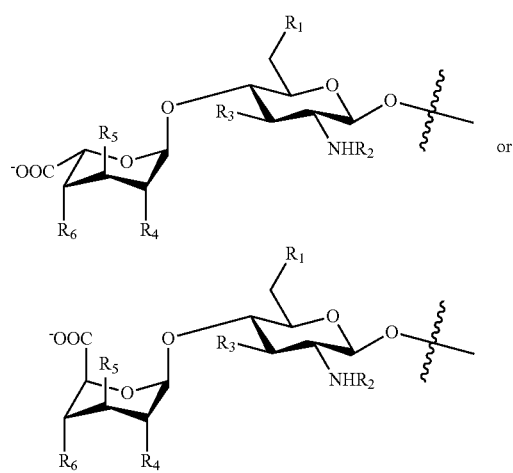

wherein:

n can an integer between 1 and 1000000;

R' and R" can each be independently selected from the group consisting of unsubstituted or substituted alkyl, unsubstituted or substituted heteroalkyl, unsubstituted or substituted aryl, unsubstituted or substituted heteroaryl, unsubstituted or substituted cycloalkyl, and unsubstituted or substituted heterocycloalkyl;

$R_1$, $R_2$, $R_4$, $R_5$ and $R_6$ can each be independently selected from the group consisting of hydrogen, hydroxyl, sulfite, sulfate, acetyl, phosphate and carboxylate; and $R_3$ can be sulfate.

In some cases, $R_2$ can be sulfite. In further cases, each of $R_1$ and $R_4$ can be independently sulfate; and $R_2$ can be sulfite. In some cases, $R_5$ and $R_6$ are hydroxyl.

In another aspect, the present disclosure provides a glycopolymer comprising a plurality of repeating units, wherein each of the repeating units comprises a saccharide moiety (SA), a linking group (L) and a polymer backbone moiety (PB). The repeating units can be optionally connected by one or more carbon-carbon double bonds. In some cases, the glycopolymer can be of the formula:

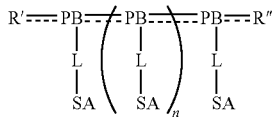

wherein:

n can be an integer between 1 and 1000000;

R' and R" can each be independently selected from the group consisting of unsubstituted or substituted alkyl, unsubstituted or substituted heteroalkyl, unsubstituted or substituted aryl, unsubstituted or substituted heteroaryl, unsubstituted or substituted cycloalkyl, and unsubstituted or substituted heterocycloalkyl;

the saccharide moiety can comprise one or more heparan sulfate (HS) units; and the saccharide moiety can comprise three or more sulfate groups.

In some cases, the saccharide moiety can be selected from the group consisting of a monosaccharide, a disaccharide, a trisaccharide, a tetrasaccharide, a pentasaccharide and an oligosaccharide. In further cases, the saccharide moiety can consist of a disaccharide.

In some cases, the polydispersity of the glycopolymer can be less than about 4. In some cases, n can be greater than about 10.

In some cases, each of the repeating units can be of the formula

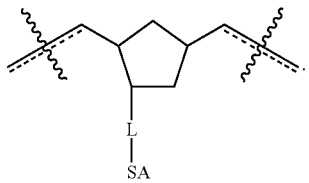

In some cases, each of the repeating units can be of the formula:

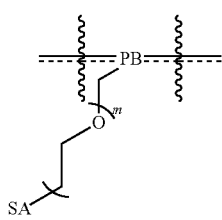

wherein m is an integer between 1 and 1000. In some examples, m is 2.

In some cases, each of the repeating units can be of the formula:

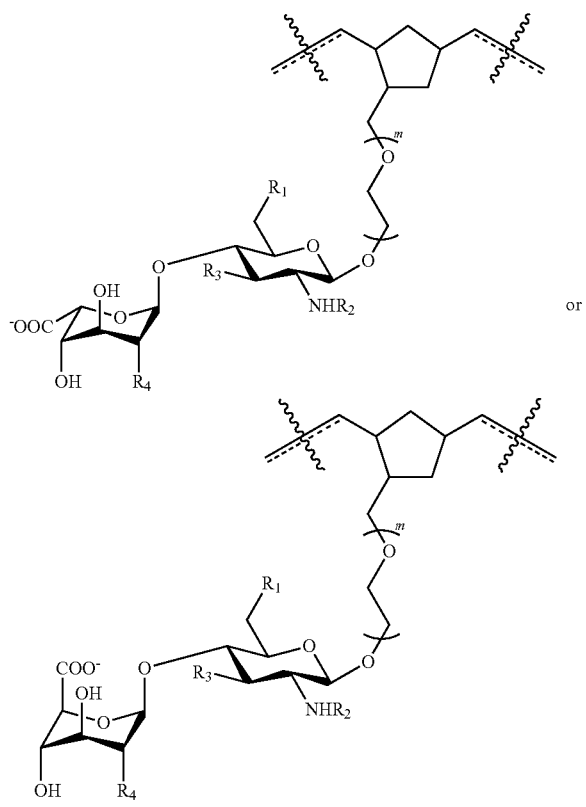

wherein $R_1$, $R_2$, $R_3$ and $R_4$ are each independently selected from the group consisting of hydrogen, hydroxyl, sulfite, sulfate, acetyl, phosphate and carboxylate. In some examples, m is 2. In some examples, each of $R_1$, $R_3$ and $R_4$ are sulfate; and $R_2$ is sulfite.

In another aspect, the present disclosure provides a method of reducing coagulation in a blood population comprising subjecting a therapeutically effective amount of a glycopolymer of the present disclosure to the blood population. In some cases, the blood population can be in a mammalian subject. In other cases, the blood population can be isolated from a mammalian subject.

In some cases, the reduction in coagulation is ascertained by an in vitro assay. In some cases, the glycopolymer can inhibit FXa activity with an IC50 value of 11.0 nM or less as ascertained by the in vitro assay. In further cases, the glycopolymer can inhibit FXa activity with IC50 of 114 pM or less as ascertained by the in vitro assay. In some cases, the composition can have an anticoagulant efficacy with prothrombin time (PT) of 13.3 s or more as ascertained by the in vitro assay.

In yet another aspect, the present disclosure comprises a composition comprising a substantially homogeneous population of a glycopolymer of the present disclosure. In some cases, the composition can comprise greater than 50% (w/w) of the glycopolymer. In some cases, the composition can comprise greater than 80% (w/w) of the glycopolymer. In further cases, the composition can comprise greater than 95% (w/w) of the glycopolymer.

In one aspect, the present disclosure provides a pharmaceutical composition comprising a glycopolymer of the present disclosure and a pharmaceutically acceptable carrier.

In another aspect, the present disclosure provides a pharmaceutical composition comprising a glycopolymer of the present disclosure and a second pharmaceutical agent.

In yet another aspect, the present disclosure provides a kit comprising a glycopolymer of the present disclosure.

In a further aspect, the present disclosure provides a substrate, wherein a glycopolymer of the present disclosure is immobilized thereon. In some cases, the substrate can comprise a solid support. In some cases, the substrate can be an array.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A provides schematics of heparin/heparan sulfate (HS) polysaccharides and their synthetic mimetics.

FIG. 1B shows an exemplary route for the retrosynthesis of glycopolymers.

FIGS. 10A and 10B show exemplary methods for synthesizing a polymer-conjugated acceptor and a glycosyl phosphate donor.

FIGS. 12A and 12B show the relative FXa and FIIa activity of heparin, LMWH and Arixtra.

FIGS. 13A and 13B show the relative FXa and FIIa activity of heparin and glycopolymers.

FIGS. 14A, 14B and 14C show the neutralization of the anti-FIIa activity of heparin, glycopolymers 26-30 and 26-45 by PF4.

DETAILED DESCRIPTION

Figure 2:
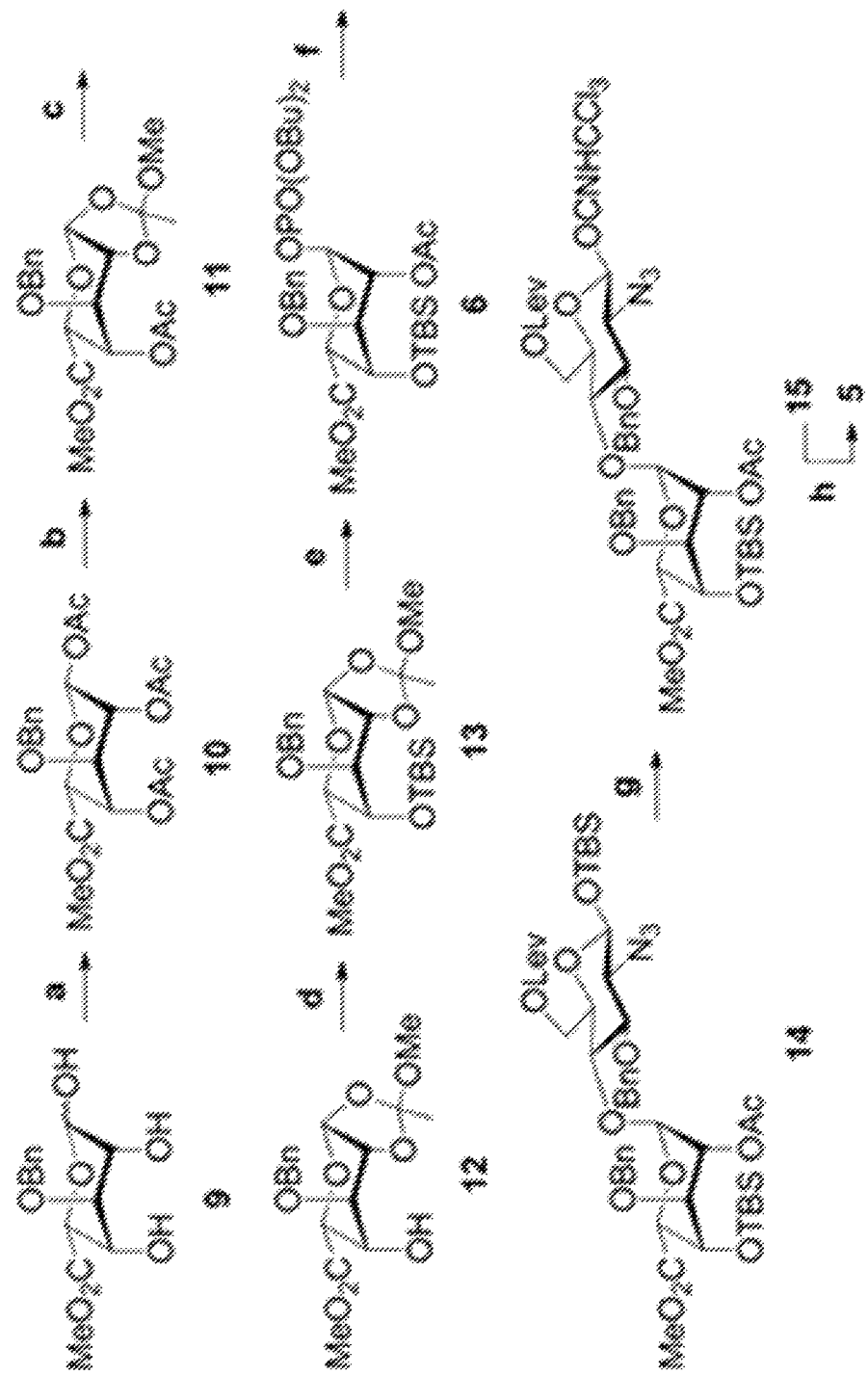
FIG. 2 shows an exemplary method for synthesizing compounds.

Glycosaminoglycans such as heparan sulfate (HS) participate in critical biological processes by modulating the activity of a diverse set of protein binding partners. Such proteins include all known members of the chemokine superfamily, which are thought to guide the migration of immune cells through their interactions with HS. A major challenge to understanding the structure-activity relationship of HS and developing HS-based therapeutic approaches has been the chemical complexity and heterogeneity of HS in vivo. Heparin, a close structural relative of HS, displays less heterogeneity and is used clinically as an anti-coagulant drug for the prevention and treatment of thrombosis. Elegant studies have demonstrated that a unique sulfated sequence found within heparin is primarily responsible for its anti-coagulant activity. Heparin has also been shown to have potent anti-inflammatory activity in models of asthma, chronic dermatitis, and ulcerative colitis, but it is not recommended as an anti-inflammatory agent in clinical practice due to its anti-coagulant activity.

Moreover, heparin isolated from natural sources can induce other undesirable physiological effects due to its structural complexity and heterogeneity. First, it carries the potential risk of contamination. The global distribution of contaminated heparin in 2007, for example, resulted in over 100 deaths and hundreds of additional cases reporting adverse clinical effects. Second, heparin displays a variable dose-response relationship among patients, in part due to its structural heterogeneity, and thus often requires active monitoring to fine-tune the dosages. Lastly, approximately 3% of patients undergoing prolonged heparin therapy experience heparin-induced thrombocytopenia (HIT), a severe autoimmune response triggered by the complex formation of heparin and platelet factor 4 (PF4). Therefore, there is a need to develop safer alternatives to natural-sourced glycosaminoglycans that have more predictable bioactivity and reduced side effects.

As used herein, the singular form "a", "an", and "the" include plural references unless the context clearly dictates otherwise.

As used herein, the term "glycopolymer" refers to any polymer that comprises one or more saccharide moieties, for example, a polysaccharide, or a glycosaminoglycan.

As used herein, the term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

The term "treatment", "treating", "palliating" or "ameliorating" are used interchangeably herein and can refer to an approach for obtaining beneficial or desired results including but not limited to therapeutic benefit and/or a prophylactic benefit. Therapeutic benefit can mean eradication or amelioration of the underlying disorder being treated. A therapeutic benefit can be achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. For purposes of this invention, beneficial or desired clinical results include, but are not limited to, one or more of the following: reducing the proliferation of, or destroying, cancerous cells or other diseased cells, reducing metastasis of cancerous cells found in cancers, shrinking the size of the tumor, decreasing symptoms resulting from the disease, increasing the quality of life of those suffering from the disease, palliating the pain resulting from the disease, decreasing the dose of other medications required to treat the disease, delaying the progression of the disease, and/or prolonging survival of individuals. Treatment can include preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a glycosaminoglycan, a glycomimetic, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one organ, or portion of the body, to another organ, or portion of the body. Each carrier must be "acceptable" in the sense of being compatible with the other ingredients of the formulation and not injurious to the subject.

As used herein, the term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

As used herein, the term "homogeneous" refers to a mixture or blend of components that is generally uniform in structure and composition with little variability throughout the mixture. Different portions of a homogeneous mixture exhibit the same physical and chemical properties at every place throughout the mixture. The stoichiometry in a homogeneous mixture is also constant throughout the mixture.

As used herein, the term "anti-inflammatory activity" means an ability to reduce or prevent one or more biological processes associated with inflammatory events.

As used herein, the term "anti-coagulant activity" we mean an ability to reduce or prevent coagulation (i.e. the clotting of blood) or an associated signal or effect.

As used herein, the term "administer" or "administering" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

As used herein, a "subject" means a human or an animal, such as a patient, a domesticated animal (e.g., dog, cat, and the like), a farm animal (e.g., cow, sheep, pig, horse, and the like) or a laboratory animal (e.g., rat, mouse, guinea pig, and the like).

As used herein, the term "in vivo" refers to an event that takes place in a subject's body.

As used herein, the term "in vitro" refers to an event that takes places outside of a subject's body. For example, an in vitro assay may encompass any assay run outside of a subject assay. In vitro assays may encompass cell-based assays in which cells alive or dead are employed. In vitro assays may also encompass a cell-free assay in which no intact cells are employed.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium (3H), iodine-125 (125I) or carbon-14 (14C). All isotopic variations of the compounds of the present invention, whether radioactive or not, are encompassed within the scope of the present invention.

As used herein, the term "alkyl" refers to a straight or branched hydrocarbon chain radical consisting solely of carbon and hydrogen atoms, containing no unsaturation, having from one to one hundred carbon atoms (e.g., C1-C100 alkyl). Whenever it appears herein, a numerical range such as "1 to 100" refers to each integer in the given range; e.g., "1 to 100 carbon atoms" means that the alkyl group may consist of 1 carbon atom, 2 carbon atoms, 3 carbon atoms, etc., up to and including 100 carbon atoms, although the present definition also covers the occurrence of the term "alkyl" where no numerical range is designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso propyl), n-butyl, n-pentyl, 1,1-dimethylethyl (t butyl), 3-methylhexyl, 2-methylhexyl, and the like. An alkyl moiety may be unsubstituted or substituted.

As used herein, the term "heteroalkyl" refers to a straight- or branched-chain alkyl group preferably having from 2 to 100 carbons, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group. A heteroalkyl moiety may be unsubstituted or substituted.

As used herein, the term "aromatic" or "aryl" refers to an aromatic radical with three to sixteen carbon atoms (e.g., —C3-16aromatic or —C3-16aryl) which has at least one ring having a conjugated pi electron system which is carbocyclic (e.g., phenyl, fluorenyl, and naphthyl). Whenever it appears herein, a numerical range such as "C3-10" refers to each integer in the given range; e.g., "—C3-10aryl" means that the aryl group may consist of 3 ring atoms, 4 ring atoms, etc., up to and including 10 ring atoms. The term includes monocyclic or fused-ring polycyclic (i.e., rings which share adjacent pairs of ring atoms) groups. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxynaphthyl, 4-(trifluoromethyl)naphthyl, 2-iodo-4-methylnaphthyl, and the like. An aryl moiety may be unsubstituted or substituted.

As used herein, the term "heteroaryl" or, alternatively, "heteroaromatic", "hetaryl", "heteroar" or "hetar" refers to an aromatic radical with one to sixteen carbon atoms (e.g., —C1-16heteroaryl) that further includes one or more ring heteroatoms selected from nitrogen, oxygen and sulfur, and which may be a monocyclic, bicyclic, tricyclic or tetracyclic ring system. Whenever it appears herein, a numerical range such as "C1-10" refers to each integer in the given range; e.g., "—C1-10hetaryl" means that the heteroaryl group may consist of 1 carbon atoms, 2 carbon atoms, etc., up to and including 10 carbon atoms. An "N-containing heteroaromatic" or "N-containing heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). A heteroaryl moiety may be unsubstituted or substituted.

As used herein, the term "cycloalkyl" refers to a saturated or partially unsaturated ring structure with three to ten carbon atoms (i.e. —C3-10cycloalkyl). Whenever it appears herein, a numerical range such as "C3-10" refers to each integer in the given range; e.g., "—C3-10cycloalkyl" means that the cycloalkyl group may consist of 3 carbon atoms, 4 carbon atoms, etc., up to and including 10 carbon atoms. The term includes monocyclic or fused-ring polycyclic (i.e., rings which share adjacent pairs of ring atoms) groups. A cycloalkyl moiety may be unsubstituted or substituted.

As used herein, the term "heterocyclyl", "hetcyclyl", or "heterocycloalkyl" refers to a 3-, 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Whenever it appears herein, a numerical range such as "C1-10" refers to each integer in the given range; e.g., "—C1-10heterocyclyl" means that the heterocycloalkyl group may consist of 1 carbon atoms, 2 carbon atoms, etc., up to and including 10 carbon atoms. Examples of heterocyclyl include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and chromanyl. A heterocycloalkyl moiety may be unsubstituted or substituted.

As used herein, the term "alkoxy" denotes an optionally substituted straight or branched chain alkyl-oxy group wherein the "alkyl" portion is as defined such as methoxy, ethoxy, n-propyloxy, i-propyloxy, n-butyloxy, i-butyloxy, tert.-butyloxy, pentyloxy, hexyloxy, heptyloxy including their isomers.

As used herein, the term "substituted" means that the referenced group may be substituted with any one or more additional chemical group(s) known in the art. Examples of such chemical groups include, but are not limited to, alkyl, cycloalkyl, aryl, heteroaryl, heterocyclyl, hydroxy, alkoxy, aryloxy, mercapto, alkylthio, arylthio, cyano, halo, amino (unsubstituted, or mono- or disubstituted), acyl, carbonyl, carboxyl, ester, amido, thiocarbonyl, isocyano, thiocyano, isothiocyano, nitro, perhaloalkyl, (e.g. perfluoroalkyl), phosphate, silyl, sulfinyl, sulfonyl, sulfonamidyl, sulfoxyl, sulfonate, carbohydrates, and any protected derivatives thereof. The substituents themselves may be substituted, for example, a cycloalkyl substituent may have a halide substituted at one or more ring carbons, and the like. The protecting groups that may form the protected derivatives of the above substituents are known to those of skill in the art and may be found in references such as Wuts P.; Greene T., (Greene's Protective Groups in Organic Synthesis, 4th Edition, 2006) which is herein incorporated by reference in its entirety.

Compounds described herein can contain one or more asymmetric centers and may thus give rise to diastereomers and optical isomers. The present disclosure includes all such possible diastereomers as well as their racemic mixtures, their substantially pure resolved enantiomers, all possible geometric isomers, and pharmaceutically acceptable salts thereof. Furthermore, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present disclosure includes all manner of rotamers and conformationally restricted states of a compound of the invention.

Compounds

I. General Structure

In one aspect, the present disclosure provides a glycopolymer. The glycopolymer can comprise a plurality of repeating units, wherein each of the repeating units comprises a saccharide moiety (SA), a linking group (L) and a polymer backbone moiety (PB). The repeating units can be optionally connected by one or more carbon-carbon double bonds. For example, the glycopolymer can be of the formula:

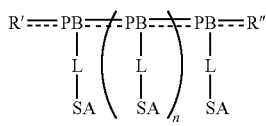

wherein n is an integer between 1 and 1000000; R' and R" are each independently selected from the group consisting of unsubstituted or substituted alkyl, unsubstituted or substituted heteroalkyl, unsubstituted or substituted aryl, unsubstituted or substituted heteroaryl, unsubstituted or substituted cycloalkyl, and unsubstituted or substituted heterocycloalkyl.

In some cases, n can be an integer greater than 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 600, 700, 800, 900, 1000, 1500, 2000, 2500, 3000, 4000, 5000, 6000, 7000, 8000, 9000, 10000, 15000, 20000, 25000, 30000, 40000, 50000, 60000, 70000, 80000, 90000, 100000, 150000, 200000, 250000, 300000, 400000, 500000, 600000, 700000, 800000, 900000, or 1000000. For example, n may be greater than 10 or 45. Alternatively, n can be an integer less than 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 600, 700, 800, 900, 1000, 1500, 2000, 2500, 3000, 4000, 5000, 6000, 7000, 8000, 9000, 10000, 15000, 20000, 25000, 30000, 40000, 50000, 60000, 70000, 80000, 90000, 100000, 150000, 200000, 250000, 300000, 400000, 500000, 600000, 700000, 800000, 900000, or 1000000. For example, n can be smaller than 1000 or 500. In some cases, n may be in a range between any of the two values described herein. For example, n can be 48 or 155.

In some cases, R' and R" can be each independently selected from the group consisting of unsubstituted or substituted alkyl, unsubstituted or substituted aryl, and unsubstituted or substituted cycloalkyl. In other cases, R' and R" are each independently selected from the group consisting of unsubstituted or substituted heteroalkyl, unsubstituted or substituted heteroaryl, and unsubstituted or substituted heterocycloalkyl. In some cases, R' and R" are each independently selected from the group consisting of unsubstituted or substituted alkyl, unsubstituted or substituted heteroalkyl, unsubstituted or substituted aryl, and unsubstituted or substituted heteroaryl. In some examples, R' and R" can independently be unsubstituted or substituted alkyl. For example, R' can be methyl and R" can be benzyl (i.e. a methyl substituted with a phenyl). In some examples, R' can be unsubstituted or substituted aryl, and R" can be unsubstituted or substituted heteroalkyl. For example, R' can be 3-chloro-4-nitro-phenyl and R" can be a polyethylene glycol (PEG) linker substituted with another polymer (e.g. a glycopolymer). In some cases, the glycopolymer can be linked to other polymer(s) via the R' and/or R" to form a block copolymer.

In some cases, the repeating units can each be connected to two carbon-carbon double bonds. In some cases, the carbon-carbon double bonds can be fully or partially reduced. The ratio of the total number of carbon-carbon double bonds in the glycopolymer to the total number of the repeating units can be less than about 1. The total number of carbon-carbon double bonds can be less than the total number of repeating units. In further cases, the carbon-carbon double bonds can be fully reduced. The repeating units can each be connected to zero carbon-carbon double bonds. In some cases, the polymer backbone moiety may not comprise a tetrahydrofuranyl group, such as in the Ring-Opening Metathesis Polymerization (ROMP) product of an oxanorbornene monomer In some cases, the saccharide moiety may comprise one or more heparan sulfate (HS) units, which are known to one skilled in the art. Heparan sulfate (HS) units can comprise a first unit [e.g. β-D-glucuronic acid (GlcA) or α-L-iduronic acid (IdoA)] linked to a second unit [e.g. 2-deoxy-2-acetamido-α-D-glucopyranosy (GlcNAc) or 2-deoxy-2-sulfamido-α-D-glucopyranosyl (GlcNS)], wherein the first unit and/or second unit can be optionally substituted with one, two, three or more sulfate groups. For example, a heparan sulfate unit can be of the formula:

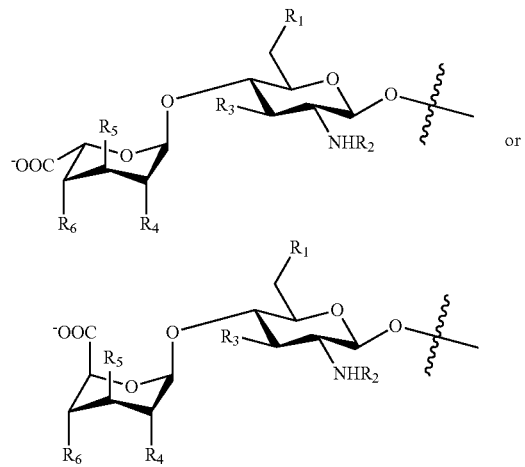

wherein $R_1$, $R_2$, $R_4$, $R_5$, $R_6$ may each be independently hydrogen, hydroxyl, sulfite, sulfate, phosphate, acetyl or carboxylate.

The saccharide moiety may comprise three or more sulfate groups. For example, the saccharide moiety may consist of three sulfate groups. Alternatively, the saccharide moiety can comprise four, five, six, or more sulfate groups.

II. Polymer Backbone Moiety (PB)

In some cases, the polymer backbone moiety can be derived from a strained ring system that can be used for Ring-Opening Metathesis Polymerization (ROMP). Examples include but are not limited to cyclobutene, cyclopentene, cyclooctene, cyclooctatetraene, norbornene, oxonorbornene, dicyclopentadiene, or substituted derivatives thereof.

In some cases, the polymer backbone moiety may be a natural polymer moiety. As used herein, "natural polymer"

refers to polymers that exist in nature, such polymers found in plants, animals and humans. In some cases, the polymer backbone moiety may be a synthetic polymer moiety. As used herein, "synthetic polymer" refers to polymers that are artificially produced by chemical processes. In some cases, the polymer backbone moiety may be a combination of natural polymer moieties and synthetic polymer moieties. Examples of natural polymer moieties include but are not limited to amino acids, saccharides (e.g. monosaccharides, dissacharides), nucleic acids, and other natural polymers, or combinations thereof. Non-limiting examples of synthetic polymer moieties may include moieties of acrylate, nylon, silicone, spandex, viscose rayon, carboxylic acid, vinyl acetate, acrylamide, ethylene glycol, cyclobutene, cyclopentene, norbornene, cyclooctene, cyclooctatetraene, urethane, lactic acid, silica, styrene, acrylonitrile, butadiene, carbonate, ethylene, ethylene terephthalate, chlorotrifluoroethylene, ethylene oxide, ethylene terephthalate, ethylene, isobutylene, methyl methacrylate, oxymethylene, formaldehyde, propylene, tetrafluoroethylene, vinyl acetate, vinyl alcohol, vinyl chloride, vinylidene dichloride, vinylidene difluoride, vinyl fluoride, or combinations (e.g., block copolymers, alternating copolymers, random copolymers etc.) thereof.

In some cases, the polymer backbone moiety can comprise a cyclopentyl group. For example, the glycopolymer may be of the formula:

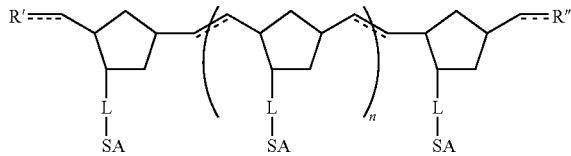

wherein R' and R" are each independently selected from the group consisting of unsubstituted or substituted alkyl, unsubstituted or substituted heteroalkyl, unsubstituted or substituted aryl, unsubstituted or substituted heteroaryl, unsubstituted or substituted cycloalkyl, and unsubstituted or substituted heterocycloalkyl.

In some cases, the polymer backbone moiety may not comprise a tetrahydrofuranyl group, such as in the Ring-Opening Metathesis Polymerization (ROMP) product of 7-oxonorbornene.

Polymer backbone moiety may be biodegradable. By "biodegradable" we mean the absorbability or degradation of a compound or composition when administered in vivo or under in vitro conditions. Biodegradation may occur through the action of biological agents, either directly or indirectly. Examples of biodegradable polymer backbone moieties include but are not limited to lactides, glycolide, trimethylene carbonate, lactide-co-glycolide, ethylene terephtalate, caprolactone, catgut suture material, collagen (e.g., equine collagen foam), lactic acid, or hyaluronic acid.

In some cases, a certain percentage of the overall population of the repeating units may comprise natural polymer backbone moieties. For example, in some cases, none of the repeating units may comprise natural polymer backbone moieties. In some cases, about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise natural polymer backbone moieties. In one example, about 10% of the repeating units may comprise natural polymer backbone moieties. In another example, about 50% of the repeating units may comprise natural polymer backbone moieties. In some cases, more than about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% of the repeating units may comprise natural polymer backbone moieties. For example, more than about 50% or 75% of the repeating units may comprise natural polymer backbone moieties. In some cases, less than about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise natural polymer backbone moieties. For example, less than about 25% or 50% of the repeating units may comprise natural polymer backbone moieties. In some cases, the percentage of repeating units that comprise natural polymer backbone moieties may fall between any of the two values described herein. For example, about 99% of the repeating units may comprise natural polymer backbone moieties.

In some cases, a certain percentage of the overall population of the repeating units may comprise synthetic polymer backbone moieties. For example, in some cases, none of the repeating units may comprise synthetic polymer backbone moieties. In some cases, about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise synthetic polymer backbone moieties. In one example, about 100% of the repeating units may comprise synthetic polymer backbone moieties. In another example, about 85% of the repeating units may comprise synthetic polymer backbone moieties. In some cases, at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% of the repeating units may comprise synthetic polymer backbone moieties. For example, at least about 75% or 90% of the repeating units may comprise synthetic polymer backbone moieties. In some cases, no more than about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise synthetic polymer backbone moieties. For example, less than about 25% or 10% of the repeating units may comprise synthetic polymer backbone moieties. In some cases, the percentage of repeating units that comprise synthetic polymer backbone moieties may fall between any of the two values described herein. For example, about 99% of the repeating units may comprise synthetic polymer backbone moieties.

In some cases, it may be desirable to have glycopolymers with a population of repeating units that comprise identical polymer backbone moieties. For example, in some cases, about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise identical polymer backbone moieties. In one example, about 50% of the repeating units may comprise identical polymer backbone moieties. In another example, about 100% of the repeating units may comprise polymer backbone moieties. In some cases, at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% of the repeating units may comprise identical polymer backbone moieties. For example, at least about 75% or 90% of the repeating units may comprise identical polymer backbone moieties. In some cases, no more than about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise identical polymer backbone moieties. For example, no more than 10% or 50% of the repeating units may comprise identical polymer backbone moieties. In some cases, the percentage of repeating units that comprise identical polymer backbone moieties may fall between any of the two values described herein. For example, about 99.5% or 99.9% of the repeating units may comprise identical polymer backbone moieties.

Additionally or alternatively, in some cases, glycopolymers with a population of repeating units that comprise differing polymer backbone moieties may be prepared. In some cases, about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise differing polymer backbone moieties. For example, about 5% or 50% of the repeating units may comprise differing polymer backbone moieties. In some cases, at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% of the repeating units may comprise differing polymer backbone moieties. For example, at least about 1% or 10% of the repeating units may comprise differing polymer backbone moieties. In some cases, no more than about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the repeating units may comprise differing polymer backbone moieties. For example, no more than 25% or 50% of the repeating units may comprise differing polymer backbone moieties. In some cases, the percentage of repeating units that comprise differing polymer backbone moieties may fall between any of the two values described herein. For example, about 0.5% of the repeating units may comprise differing polymer backbone moieties.

The polymer backbone moiety may be fully saturated, partially saturated, or unsaturated. A "partially saturated" polymer backbone moiety comprises, or is directly connected to, at least one carbon-carbon bond is unsaturated (e.g., a carbon-carbon double bond, a carbon-carbon triple bond). To modify the properties (e.g., conformation, rigidity, flexibility) of the glycopolymer, one or more of the carbon-carbon double bonds may be reduced. The degree of reduction may be determined by the ratio between total number of carbon-carbon double bonds in polymer backbone moieties and the number of repeating units. For example, if all of the carbon-carbon double bonds are reduced, the ratio is zero. Alternatively, if each of the polymer backbone moieties is connected to one or more carbon-carbon double bonds, then the ratio is greater than 1.

Based on the desired properties of glycopolymers, this ratio may be varied. In some cases, the ratio may be zero. In some cases, the ratio may be about 0.000001, 0.000005, 0.00001, 0.00005, 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1. For example, the ratio may be about 0.0001 or 0.001. In some cases, the ratio may be more than about 0.000001, 0.000005, 0.00001, 0.00005, 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1. For example, the ratio may be more than about 0.0001 or 0.1. In some cases, the ratio may be less than about 0.000001, 0.000005, 0.00001, 0.00005, 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1. For example, the ratio may be less than about 1 or 0.5. In some cases, the ratio may fall into a range of any of the two values described herein. For example, the ratio may be 0.015 or 0.12.

To tune the properties of glycopolymers, the polymer backbone moiety may be modified or functionalized (e.g., substituted, hydrothiolated, reduced, hydrogenated, hydrolyzed etc.). The polymer backbone moiety may be modified or functionalized during the formation of the glycopolymer (i.e., simultaneously), or after the formation of the glycopolymer (i.e., sequentially).

III. Linking Group (L)

As described herein, a linking group may be any groups or bonds, through which, the saccharide moiety are attached to the polymer backbone moiety. The linking group may be selected from the groups consisting alkyl, heteroalkyl, aryl, heteroaryl, cycloalkyl, heterocyclyl, alkenylalkyl, alkynyl, alkynylalkyl, hydroxyalkyl, haloalkyl and heterocycloalkyl, which may or may not be substituted by one or more of substituents. Examples of substituents may include, but not limited to alkyl, aryl, heterocyclyl, cycloalkyl, nitro, cyano, azido, amino, alkyl amino, dialkyl amino, cycloalkyl amino, aryl amino, diarylamino, heterocyclyl amino, hydroxy, alkoxy, aryloxy, heterocyclyloxy, cycloalkoxy, thio, alkylthio, arylthio, heterocyclylthio, alkyl carbonyl, cycloalkyl carbonyl, aryl carbonyl, heterocyclyl carbonyl, carboxy, alkoxycarbonyl, aminocarbonyl, alkylaminocarbonyl, arylaminocarbonyl, dialkylaminocarbonyl, diarylaminocarbonyl, heterocyclylaminocarbonyl. In some cases, substituents may be further substituted. In some cases, the linking group may be a bond (e.g. a carbon-carbon bond).

In some embodiments, the linking group may comprise a bifunctional linker, a trifunctional linker, a multifunctional linker, or a combination thereof. Examples of linking groups may include but are not limited to ethylene, ethylene glycol, oxyethylene, methylene glycol, trimethylene glycol, vinylpyrrolidones, Alkyne-PEG5-acid, N-Alloc-1,4-butandiamine hydrochloride, N-Alloc-1,6-hexanediamine hydrochloride, N-Alloc-1,3-propanediamine hydrochloride, 4-Acetyl-3,5-dioxo-1-methylcyclohexanecarboxylic acid, Allyl(4-methoxyphenyl)dimethylsilane, 6-(Allyloxycarbonylamino)-1-hexanol, 3-(Allyloxycarbonylamino)-1-propanol, 4-Aminobutyraldehyde diethyl acetal, (E)-N-(2-Aminoethyl)-4-{2-[4-(3-azidopropoxy)phenyl]diazenyl}benzamide hydrochloride, N-(2-Aminoethyl) maleimide trifluoroacetate salt, Amino-PEG4-alkyne, Benzyl N-(3-hydroxypropyl)carbamate, 4-(Boc-amino)-1-butanol, 4-(Boc-amino)butyl bromide, 2-(Boc-amino)ethanethiol, 2-[2-(Boc-amino)ethoxy]ethoxyacetic acid (dicyclohexylammonium) salt, 2-(Boc-amino)ethyl bromide, 6-(Boc-amino)-1-hexanol, 21-(Boc-amino)-4,7,10,13,16,19-hexaoxaheneicosanoic acid purum, 6-(Boc-amino)hexyl bromide, 5-(Boc-amino)-1-pentanol, 3-(Boc-amino)-1-propanol, 3-(Boc-amino)-1-propanolpurum, 3-(Boc-amino)propyl bromide, 15-(Boc-amino)-4,7,10,13-tetraoxapentadecanoic acid purum, N-Boc-1,4-butanediamine, N-Boc-cadaverine, N-Boc-ethanolamine, N-Boc-ethylenediamine, N-Boc-2,2'-(ethylenedioxy)diethylamine, N-Boc-1,6-hexanediamine, N-Boc-1,6-hexanediamine hydrochloride purum, N-Boc-1,6-hexanediamine hydrochloride, N-Boc-4-isothiocyanatoaniline, N-Boc-4-isothiocyanatobutylamine, N-Boc-2-isothiocyanatoethylamine, N-Boc-3-isothiocyanatopropylamine, N-Boc-N-methylethylenediamine, N-Boc-m-phenylenediamine, N-Boc-p-phenylenediamine, 2-(4-Boc-1-piperazinyl)acetic acid, N-Boc-1,3-propanediamine, N-Boc-1,3-propanediamine, N-Boc-N'-succinyl-4,7,10-trioxa-1,13-tridecanediamine, N-Boc-4,7,10-trioxa-1,13-tridecanediamine, N-(4-Bromobutyl)phthalimide, 4-Bromobutyric acid, 4-Bromobutyryl chloride purum, 4-Bromobutyryl chloride, N-(2-Bromoethyl)phthalimide, N-(2-Bromoethyl)phthalimide, 6-Bromo-1-hexanol, 6-Bromo-1-hexanol purum, 3-(Bromomethyl)benzoic acid N-succinimidylester, 4-(Bromomethyl)phenyl isothiocyanate, 8-Bromooctanoic acid, 8-Bromo-1-octanol, 4-(2-Bromopropionyl)phenoxyacetic acid, N-(3-Bromopropyl) phthalimide, 4-(tert-Butoxymethyl)benzoic acid, tert-Butyl 2-(4-{[4-(3-azidopropoxy)phenyl]azo}benzamido)ethylcarbamate, tert-Butyl trans-17-bromo-4,7,10,13-tetraoxa-15-heptadecenoate, 2-[2-(tert-Butyldimethylsilyloxy)ethoxy] ethanamine, tert-Butyl 4-hydroxybutyrate, 4-(2-Chloropropionyl)phenylacetic acid, 1,11-Diamino-3,6,9-trioxaundecane, di-Boc-cystamine, Diethylene glycol monoallyl ether, 3,4-Dihydro-2H-pyran-2-methanol, 4-[(2,4-Dimethoxyphenyl)(Fmoc-amino)methyl]phenoxyacetic acid, 4-(Diphenylhydroxymethyl)benzoic acid, 4-(Fmoc-amino)-1-butanol, 2-(Fmoc-amino)ethanol, 2-[2-(Fmoc-amino)ethoxy]ethylamine hydrochloride, 2-(Fmoc-amino) ethyl bromide, 6-(Fmoc-amino)-1-hexanol, 5-(Fmoc-amino)-1-pentanol, 3-(Fmoc-amino)-1-propanol, 3-(Fmoc-amino)propyl bromide, N-Fmoc-2-bromoethylamine, N-Fmoc-1,4-butanediamine hydrobromide, N-Fmoc-cadaverine hydrobromide, N-Fmoc-ethylenediamine hydrobromide, N-Fmoc-1,6-hexanediamine hydrobromide, N-Fmoc-1,3-propanediamine hydrobromide, N-Fmoc-N''-succinyl-4,7,10-trioxa-1,13-tridecanediamine, (3-Formyl-1-indolyl) acetic acid, 6-Guanidinohexanoic acid, 4-Hydroxybenzyl alcohol purum, 4-Hydroxybenzyl alcohol, N-(4-Hydroxybutyl)trifluoroacetamide, 4'-Hydroxy-2,4-dimethoxybenzophenone, N-(2-Hydroxyethyl)maleimide, 4-[4-(1-Hydroxyethyl)-2-methoxy-5-nitrophenoxy]butyric acid, N-(2-Hydroxyethyl)trifluoroacetamide, N-(6-Hydroxyhexyl) trifluoroacetamide, 4-Hydroxy-2-methoxybenzaldehyde, 4-Hydroxy-3-methoxybenzyl alcohol, 4-(Hydroxymethyl) benzoic acid, 4-Hydroxymethyl-3-methoxyphenoxyacetic acid, 4-(4-Hydroxymethyl-3-methoxyphenoxy)butyric acid, 4-(Hydroxymethyl)phenoxyacetic acid, 3-(4-Hydroxymethylphenoxy)propionic acid, N-(5-Hydroxypentyl)trifluoroacetamide, 4-(4'-Hydroxyphenylazo)benzoic acid, N-(3-Hydroxypropyl)trifluoroacetamide, 2-Maleimidoethyl mesylate, 4-Mercapto-1-butanol, 6-Mercapto-1-hexanol, Phenacyl 4-(bromomethyl)phenylacetate, 4-Sulfamoylbenzoic acid, N-Trityl-1,2-ethanediamine hydrobromide, 4-(Z-Amino)-1-butanol, 6-(Z-Amino)-1-hexanol, 5-(Z-Amino)-1-pentanol, N—Z-1,4-Butanediamine hydrochloride, N—Z-Ethanolamine, N—Z-Ethylenediamine hydrochloride purum, N—Z-Ethylenediamine hydrochloride, N—Z-1,6-hexanediamine hydrochloride, N—Z-1,5-pentanediamine hydrochloride, N—Z-1,3-Propanediamine hydrochloride, $N^1,N^4$-Bis-Boc-spermidine, $N^1,N^5$-Bis-Boc-spermidine, N-Boc-diethanolamine, $N^1$-Boc-2,2'-iminodiethylamine, N-Boc-iminodipropionic acid, N1-Boc-3,3'-iminodipropylamine, N,N''-Di-Z-diethylenetriamine, and derivatives thereof.

In some cases, the linking group may have one of the formulas selected from: —O—$(CH_2)_m$—, —O—$(CH_2)_m$—X—, —NH—$(CH_2)_m$—, —NH—$(CH_2)_m$—X—, —O—$(CH_2—CH_2—O)_m$—, —O—$(CH_2—CH_2—O)_m$—X—, —NH—$(CH_2—CH_2—O)_m$—, —NH—$(CH_2—CH_2—O)_m$—X—, where X is O or S and m is between 1 and 1000.

The linking groups may be identical or varied. In some cases, all of the repeating units may comprise an identical linking group. In some cases, equal to or less than about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise an identical linking group. For example, equal to or less than about 75% or 95% of the repeating units may comprise identical linking groups. In some cases, more than about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise an identical linking group. For example, more than about 50% or 90% of the repeating units may comprise identical linking groups. In some cases, the repeating units comprising an identical linking group may constitute a percentage of the whole population falling between any of the two values described herein. For example, about 98.5% of the repeating units may comprise identical linking groups.

Alternatively, in some cases, it may be advantageous to have repeating units that comprise differing linking groups. For example, in some cases, equal to or less than about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise different linking groups. For example, equal to or less than about 50% or 25% of the repeating units may comprise different linking groups. In some cases, more than about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise different linking groups. For example, more than about 5% or 25% of the repeating units may comprise different linking groups. In some cases, the percentage of repeating units that comprise different linking groups may be between any of the two values described herein. For example, about 2.5% or 12.5% of the repeating units may comprise different linking groups.

IV. Saccharide Moiety (SA)

As provided herein, the saccharide moiety may refer to any sugar or carbohydrate. The saccharide moiety may be natural (e.g., heparin) or synthetic. The saccharide moiety may be straight chain or cyclic, i.e., mono-, di- and poly-, straight chain and cyclic saccharides. The saccharide moiety may be a monosaccharide, a disaccharide, a trisaccharide, a tetrasaccharide, a pentasaccharide, an oligosacchride (i.e., a saccharide moiety with about 6-40 sugar residues), a polysaccharide (i.e., a saccharide moiety with about 40-3000 sugar residues), or a combination thereof. Non-limiting examples of saccharide moieties may include glucose, fructose, galactose, sucrose, lactulose, lactose, maltose, trehalose, cellobiose, chondrotin sulfate, dermatan sulfate, keratan sulfate, heparin, heparan sulfate, or combinations thereof.

In some cases, the saccharide moieties may vary in the type of uronic sugar (e.g., glucuronic acid, iduronic acid, galactose etc.) and amino sugar (e.g., glucosamine, galactosamine etc.) they contain. For example, saccharide moieties may consist of glucuronic acid and acetylgalactosamine (or GlcUA-GalNAc); iduronic acid and acetylgalactosamine (or IdoUA-GlcNAc); glucuronic acid and acetylglucosamine (or GlcUA-GlcNS); or iduronic acid and acetylglucosamine (or IdoUA-GlcNS). In some other cases, saccharide moieties may consist of galactose and acetylgalactosamine (or Gal-GlaNAc).

The saccharide moieties may be processed and functionalized (e.g., substituted). The saccharide moieties may be substituted by one or more substituents which independently are: sulfate, phosphate, carboxylate, acetyl, alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR_a$, —$SR_a$, —$OC(O)R_a$, —$N(R_a)_2$, —$C(O)R_a$, —$C(O)OR_a$, —$OC(O)N(R_a)_2$, —$C(O)N(R_a)_2$, —$N(R_a)C(O)OR_a$, —$N(R_a)C(O)R_a$, —$N(R_a)C(O)N(R_a)_2$, —$N(R_a)C(NR_a)N(R_a)_2$, —$N(R_a)S(O)_tR_a$ (where t is 1 or 2), —$S(O)_tOR_a$ (where t is 1 or 2), —$S(O)_tN(R_a)_2$ (where t is 1 or 2), or —$PO_3(R_a)_2$, where each $R_a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. The functionalization of saccharide moieties may be carried our prior to, during, or after the preparation of glycopolymers.

In some cases, the saccharide moieties may be sulfated. The sulfation pattern may be varied. By altering the sulfation pattern of the saccharide moieties, the molecular recognition and activity of glycopolymers may be defined and encoded. The precise positioning of sulfate groups may determine the affinity of glycopolymers for target molecules. For example, a single alteration in sulfation pattern (e.g., removal of a sulfate group from a specific position) may greatly change the properties of glycopolymers (e.g., abrogate a certain type of activity). In some cases, one or more sites of saccharide moieties may be sulfated, for example, in the case of disaccharide, N-sulfated, 2-O-sulfated, 3-O-sulfated, 4-O-sulfaterd, or 6-O-sulfated. In some cases, to tune the properties of glycopolymers, it may be desirable to have saccharide moieties with one or more desulfated sites, e.g., N-desulfated, 2-O-desulfated, 3-O-desulfated, 4-O-desulfated, or 6-O-desulfated if a disaccharide moiety is included.

The degree of sulfation may be altered. For example, in some cases, each saccharide moiety may consist of 1, 2, 3, 4, 5, 6, 7, 8, 9, 10, 11, 12, 13, 14, 15, 16, 17, 18, 19, 20, 25, 30, 35, 40, 45, 50, 55, 60, or more sulfate groups. In one example, each saccharide moiety may consist of three sulfate groups. In another example, each saccharide moiety may consist of four sulfate groups. In some cases, each saccharide moiety may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, or more sulfate groups. For example, each saccharide moiety may comprise at least three or four sulfate groups. In some cases, each saccharide moiety may comprise no more than about 1, 2, 3, 4, 5, 6, 7, 8, 9, 10, 11, 12, 13, 14, 15, 16, 17, 18, 19, 20, 25, 30, 35, 40, 45, 50, 55, 60, or more sulfate groups. For example, each saccharide moiety may comprise no more than 10 or 6 sulfate groups. In some cases, the number of sulfate groups contained in each saccharide moiety falls into a range of any of the two values described herein.

In some cases, the saccharide moiety may be of the formula:

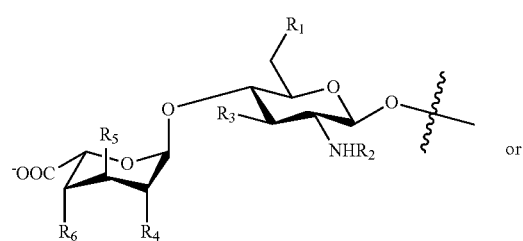

or

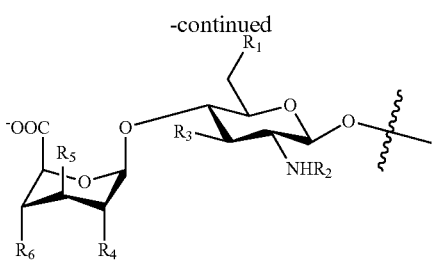

wherein $R_1$, $R_2$, $R_3$, $R_4$, $R_5$, $R_6$ are each independently hydrogen, hydroxyl, sulfite, sulfate, phosphate, acetyl, or carboxylate.

In some cases, $R_1$, $R_2$, $R_4$, $R_5$ may each be independently hydrogen, hydroxyl, sulfite, sulfate, phosphate, acetyl, or carboxylate; and $R_3$ and $R_6$ may each be independently hydroxyl or sulfate. In some cases, $R_1$, $R_2$, $R_4$, $R_6$ may each be independently hydrogen, hydroxyl, sulfite, sulfate, phosphate, acetyl, or carboxylate; and $R_3$ and $R_5$ may each be independently hydroxyl or sulfate. In some cases, $R_1$, $R_2$, $R_4$ may each be independently hydrogen, hydroxyl, sulfite, sulfate, phosphate, acetyl, or carboxylate; and $R_3$, $R_5$ and $R_6$ may each be independently hydroxyl or sulfate. In some cases, $R_1$ and $R_2$ may each be independently hydrogen, hydroxyl, sulfite, sulfate, phosphate, acetyl, or carboxylate; and $R_3$, $R_4$, $R_5$ and $R_6$ may each be independently hydroxyl or sulfate. In some cases, $R_2$ may each be independently hydroxyl, sulfite, sulfate, phosphate, acetyl or carboxylate; and $R_1$, $R_3$, $R_4$, $R_5$ and $R_6$ may each be independently hydroxyl or sulfate. For example, in some cases, $R_1$, $R_3$ and $R_4$ may each be independently sulfate; $R_2$ can be sulfite; and $R_5$ and $R_6$ may each be independently hydroxyl. In another example, $R_1$ and $R_4$ may each be independently sulfate; $R_2$ can be sulfite; and $R_3$, $R_5$ and $R_6$ may each be independently hydroxyl. In a further example, $R_1$ may each be sulfate; $R_2$ may be sulfite; and $R_3$, $R_4$, $R_5$ and $R_6$ may each be independently hydroxyl.

As will be appreciated, in certain cases, it may be desirable to prepare a glycopolymer with an indicated percentage of repeating units that comprise identical saccharide moieties. For example, in some cases, at least 80% of the saccharide in the repeating units may comprise a heparan sulfate unit. In some cases, about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise identical saccharide moieties. For example, about 75% or 95% of the repeating units may comprise identical saccharide moieties. In some cases, at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise identical saccharide moieties. For example, at least about 50% or 90% of the repeating units may comprise identical saccharide moieties. In some cases, no more than about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise identical saccharide moieties. For example, no more than 99% or 90% of the repeating units may comprise identical saccharide moieties. In some cases, the repeating units comprising identical saccharide moieties may constitute a percentage of the whole population falling between any of the two values described herein. For example, about 98.5% of the repeating units may comprise identical saccharide moieties.

Alternatively, in some cases, a glycopolymer with an indicated percentage of repeating units that comprise different saccharide moieties may be prepared. For example, part of the repeating units may comprise a disaccharide moiety, while another part of the repeating units may comprise a monosaccharide moiety, a trisaccharide moiety, or a pentasaccharide moiety. In some cases, about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise different saccharide moieties. For example, about 25% or 50% of the repeating units may comprise different saccharide moieties. In some cases, at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise different saccharide moieties. For example, at least about 10% or 25% of the repeating units may comprise different saccharide moieties. In some cases, no more than about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the repeating units may comprise different saccharide moieties. For example, no more than about 10% or 25% of the repeating units may comprise different saccharide moieties. In some cases, the repeating units comprising different saccharide moieties may make up a percentage of the whole population falling into a range of any of the two values described herein. For example, about 2.5% of the repeating units may comprise different saccharide moieties.

V. Repeating Units

As described above, each glycopolymer disclosed herein may comprise a plurality of repeating units. Each repeating unit may comprise a polymer backbone moiety (PB), and/or a linking group (L), and/or a saccharide moiety (SA). The glycopolymer may comprise a plurality of identical or different repeating units. By "identical repeating units" we mean that each of the repeating units comprise identical PB, L and SA, which are each connected in the same configuration. In some cases, the glycopolymers can comprise identical repeating units. In other cases, the glycopolymers can comprise a certain percentage of differing repeating units (i.e., at least one of PB, L, or SA, is not identical among different repeating units).

In some cases, a certain population of the repeating units included in a glycopolymer may be identical. For example, in some cases, equal to or less than about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the repeating units in a glycopolymer are identical. In one example, equal to or less than about 75% of the repeating units are identical. In another example, equal to or less than about 99% of the repeating units are identical. In some cases, more than about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the repeating units in a glycopolymer are identical. For example, no more than 90% or 75% of the repeating units are identical. In some cases, the identical repeating units included may constitute a certain percentage of the whole population which may fall into a range of any of the two values described herein. For example, about 99.5% of the repeating units are identical.

In some cases, it may be preferred to have glycopolymers with a certain percentage of differing repeating units such that the properties of glycopolymers may be tuned. For example, in the case where highly charged saccharide moieties are attached, to have a less rigid polymer chain, the number or the percentage of the repeating units that comprise saccharide moieties may be controlled or adjusted (e.g., 80% of the repeating units may comprise saccharide moieties). In some cases, equal to or less than about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the repeating units in a glycopolymer are different. For example, equal to or less than about 25% or 50% of the repeating units are different. In some cases, more than about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the repeating units in a glycopolymer are different. For example, more than about 10% or 25% of the repeating units are different. In some cases, the percentage of different repeating units may fall between any of the two values described herein. For example, about 7.5% of the repeating units are different.

In some cases, the repeating unit may be of the formula:

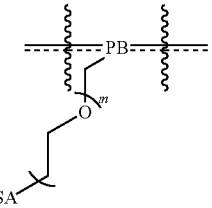

wherein PB is a polymer backbone moiety and SA is a saccharide moiety; and m is an integer between 1 and 1000.

In some cases, the repeating units may be of the formula:

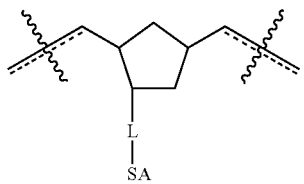

wherein L is a linking group and SA is a saccharide moiety.

In some cases, the repeating units may be of the formula:

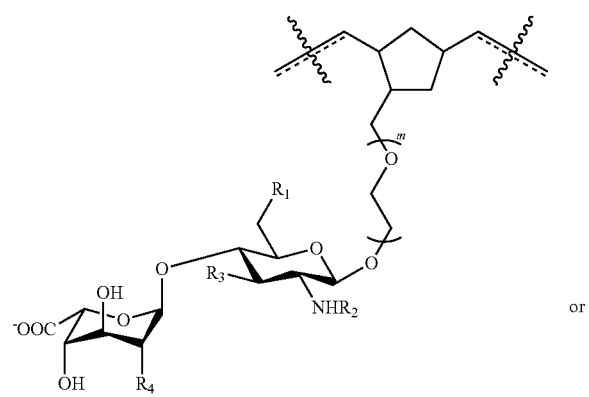

or

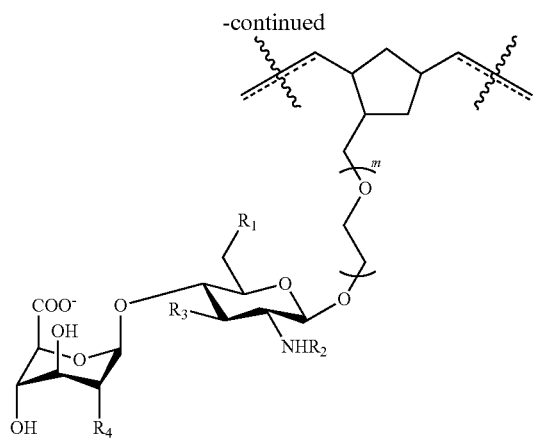

wherein $R_1$, $R_2$, $R_3$ and $R_4$ may each be independently selected from the group consisting of hydrogen, hydroxyl, sulfite, sulfate, acetyl, phosphate and carboxylate; and m is an integer between 1 and 1000. In some examples, $R_3$ can be hydroxyl. In other examples, $R_3$ can be sulfate.

VI. Embodiments/Properties

By utilizing different preparing (e.g., polymerization) conditions, the properties of glycopolymers can be controlled and tuned. Exemplary properties may include, but not limited to the degree of polymerization, length, size, structure, conformation, rigidity, sulfation degree, sulfation pattern, degree of reduction, polydispersity, or combinations thereof.

The degree of polymerization (DP) may be determined by the number of repeating unit, n. In some cases, glycopolymer with a higher DP (i.e., larger n) may be prepared. In some cases, glycopolymer with a lower DP (i.e., smaller n) may be prepared In some cases, n may be about 1, 2, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 50000, 100000, 500000, or 1000000. For example, n may be 15, 30 or 45. In some cases, n may be more than about 1, 2, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 50000, 100000, 500000, or 1000000. For example, n may be more than about 10, 30, 100 or 500. In some cases, n may be less than about 2, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 50000, 100000, 500000, or 1000000. For example, n may be less than about 50, 100, 300 or 1000. In some cases, n may fall between any two of the values described herein. For example, n may be 46, 48, 99 or 155.

The polydispersity index (PDI) or heterogeneity index, is a measure of the distribution of molar mass in a given polymer sample, or the uniformity of the given polymer sample. The PDI can be determined by the ratio of $M_w/M_n$, where $M_w$ and $M_n$ are weight-averaged and number-averaged molecular weight (or molar mass), respectively. As the polymer chains approach uniform chain length, the PDI approaches unity (1). Experimental methods for determining the PDI include mass spectrometry, gel permeation chromatography and light scattering.

In many cases, the preparing conditions are used to ensure that the generated glycopolymers have a lower PDI, or a narrower distribution. Glycopolymers with a narrow polydispersity (or lower PDI) may be free of interfering glycopolymers with differing DP and thus differing biological effects. For example, in some cases, the PDI may be less than about 2. In some cases, a higher PDI may be needed. In some cases, the PDI may be about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.5, 6, 6.5, 7, 7.5, 8, 8.5, 9, 9.5, 10. For example, the PDI may be about 1.3, 1.4 or 2.0. In some cases, the PDI may be at least about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.5, 6, 6.5, 7, 7.5, 8, 8.5, 9, 9.5, 10. For example, the PDI may be at least about 1 or 1.2. In some cases, the PDI may be no more than about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.5, 6, 6.5, 7, 7.5, 8, 8.5, 9, 9.5, 10. For example, the PDI may be no more than 2, 3 or 4. In some cases, the PDI may fall between any two of the values described herein. For example, the PDI may be about 1.25, 1.29 or 1.32.

In some embodiments of the present disclosure, the methods described herein may provide glycopolymers with substantial homogeneity. Exemplary methods for purifying the prepared glycopolymers may include but are not limited to thin layer chromatography; silica gel, reverse phase, ion-exchange, and gel permeation chromatography; and lypholization. As used herein, substantial homogeneity means at least about 25% pure including about 30%, 35%, 40%, 45%, 50%, 55%, 60%, 65%, 70%, 75%, 80%, 85%, 90%, 95%, 97.5%, 99%, or about 99.5% pure or higher. In some cases, substantially homogeneous may additionally mean having a PDI of less than about 5, less than about 4, less than about 3, less than about 2 or less than about 1.5. Methods for determine the purity may include but are not limited to chromatographic methods with the use of refractive index and electrochemical detection, light scattering, mass spectrometry, and sedimentation velocity. In some cases, a chromophore or fluorophore may be covalently linked to the glycopolymers of the present disclosure allowing detection by spectrophotometric (UVNis) or fluorometric techniques In some embodiments of the present disclosure, the methods described herein may provide glycopolymers in high yield. Synthetic yields may be calculated by a number of methods. An exemplary method may comprise steps: (1) determining the amount and purity of the starting material and the final product; (2) dividing the pure amount of the final product by that of the starting material; and (3) multiplying the quotient determined from step (2) by 100 to obtain a percent yield. To determine the yield, one may further take into consideration the stoichiometry of the reaction. Methods for determining the amount of starting material and/or final product may include but are not limited to weighing. In some cases, the final yield may be determined by multiplying the yield at each step of the synthetic scheme. In some cases, the yield may be about 50%, 55%, 60%, 65%, 70%, 75%, 80%, 85%, 90%, 95%, or 100%. For example, the yield may be about 90%. In some cases, the yield may be at least about 50%, 55%, 60%, 65%, 70%, 75%, 80%, 85%, 90%, 95%, or 100%. For example, the yield may be at least about 75% or 90%. In some cases, the yield may be between any two of the values described herein. For example, the yield may be about 91%, 93% or 97%.

Methods for Preparing Glycopolymers

The glycopolymer of the present disclosure can be prepared via a variety of routes and techniques, such as free radical polymerization, step-growth polymerization, condensation polymerization, cationic addition polymerization, anionic addition polymerization, living cationic polymerization, living anionic polymerization, living ring-opening metathesis polymerization, living free radical polymerization, reversible addition-fragmentation chain transfer polymerization (RAFT), atom transfer radical polymerization (ATRP), ring-opening polymerization, ring-opening metathesis polymerization (ROMP), emulsion polymerization, solution polymerization, suspension polymerization, and precipitation polymerization.

As described elsewhere herein, to temper the polymer properties, different preparing conditions (e.g., temperature, pressure, type and composition of initiator and optionally catalyst, type of solvent etc.) may be used.

In some cases, ROMP may be used to prepare the glycopolymers. ROMP is a variant of olefin metathesis and uses optionally substituted cyclic alkyls with at least one carbon-carbon double bond to produce polymers and co-polymers with a low polydispersity index. The mechanism for ROMP follows similar pathways as olefin metathesis. The catalysts used in the ROMP reaction include a wide variety of metals and range from a simple $RuCl_3$/alcohol mixture to Grubbs' catalysts (e.g. Grubbs' first generation catalyst, Grubbs' second generation catalyst, etc.). Organometallic catalysts, such as W, Mo, Re, Ru, and Ti carbenes complexes, may be used. The catalysts used in the ROMP reaction may also include Schrock catalyst, Grubbs catalyst or derivatives thereof.

ROMP may be applied to strained cyclic monomers. A number of cyclic structures may be used as monomers in ROMP reaction, such as homo-monocyclic-, hetero-monocyclic-, homo-bicyclic-, hetero-bicyclic-, homo-tricyclic-, hetero-tricyclic-, homo-polycyclic-, hetero-polycyclic- rings, or derivatives thereof. Non-limiting examples of monomers may include cyclobutene, cyclopentene, cyclooctene, cyclooctatetraene, norbornene, dicyclopentadiene, or derivatives thereof. In some cases, various substituents can be included in the monomers, in the transition metal catalyst, or in the reaction mixture to tune the polymerization reaction. Numerous organic and inorganic moieties may be used as substituents. Non-limiting examples of substituents may include alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $-OR_a$, $-SR_a$, $-OC(O)R_a$, $-N(R_a)_2$, $-C(O)R_a$, $-C(O)OR_a$, $-OC(O)N(R_a)_2$, $-C(O)N(R_a)_2$, $-N(R_a)C(O)OR_a$, $-N(R_a)C(O)R_a$, $-N(R_a)C(O)N(R_a)_2$, $-N(R_a)C(NR_a)N(R_a)_2$, $-N(R_a)S(O)_tR_a$ (where t is 1 or 2), $-S(O)_tOR_a$ (where t is 1 or 2), $-S(O)_tN(R_a)_2$ (where t is 1 or 2), or $-PO_3(R_a)_2$, where each $R_a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

As described elsewhere herein, to prepare glycopolymers with certain properties, when conducting ROMP reaction, different solvent and/or solvent systems may be used. The solvent may be polar or non-polar. Non-limiting examples of solvents may include water, methanol, ethanol, isopropanol, dichloromethane, toluene, hexane, tetrachloroethylene, pentane, cyclopentane, cyclohexane, benzene, dioxane, chloroform, diethyl ether, tetrahydrofuran, ethyl acetate, acetone, dimethylformamide, acetonitrile, dimethyl sulfoxide, formic acid, n-Butanol, acetic acid, n-propanol, or combinations thereof. In some cases, a solvent system (or a mix of solvents) may be used. The solvent system may include two or more different types of solvents, for example, the solvent system may comprise 2, 3, 4, 5 or more different type of solvents. In case where a solvent system is used, various ratios of composing solvents may be used. For example, in some cases, a solvent system may consist of two solvents A and B, where A and B can be any of the solvents described above, the ratio of A/B can be about 1:10, 1:9, 1:7, 1:6, 1:5, 1:4, 1:3, 1:2, or 1:1. Or, in some cases, the ratio of A/B may fall into a range of any two of the values described herein.

The preparation of the glycopolymers may comprise one or more steps. Further, one or more types of solvents and/or solvent systems may be used for each single step. The types of solvents and/or solvent systems used in the preparation process may also vary. In some cases, a single type of solvent or solvent systems may be used. In some cases, each step may involve a distinct type of solvent or solvent system. In some cases, some of the steps may use the same solvent or solvent system, while some other steps may involve the use of differing solvents and/or solvent systems.

It should be noted that, even in cases where the same solvent system (i.e., consisting of same solvent components) is applied, the ratios of different solvent components may vary, depending upon, the target properties of the product (e.g., DP or PDI of the synthesized glycopolymer). Or, in the cases where more than one step is contained in the reaction, some certain ratio of solvents in a solvent system may be used in some steps, and another ratio of solvents may be used in other steps. In some cases, the solvent system may consist of MeOH and $(CH_2Cl)_2$, and the ratio of MeOH:$(CH_2Cl)_2$ may be varied from 1:4 to 1:2.5 depending upon, the target polymer length. In one example, a ratio of 1:4 MeOH:$(CH_2Cl)_2$ may be used to synthesize polymers with n of 4, 6 and 8. In another example, a ratio of 1:3 MeOH:$(CH_2Cl)_2$ may be used to synthesize polymers with n of 10 and 15. In a further example, a ratio of 1:2.5 MeOH:$(CH_2Cl)_2$ may be used for the synthesis of polymers with n of 30 and 50.

As described elsewhere herein, by tuning the reaction conditions, or altering a number of variables of the reaction, we may adjust and control the properties (e.g., chain length, conformation, configuration, polydispersity, sulfation degree of the saccharide moiety, sulfation pattern of the saccharide moiety etc.) of synthesized glycopolymers. Examples of variables may include, but not limited to, temperature of the reaction, amount and type of solvent and/or solvent system, amount and type of catalyst, ratio of solvent system, amount and type of monomer, reaction method (e.g., RAFT, ATRP, ROMP etc.), and optionally amount and type of initiator. As will be appreciated, each of the variables descried herein may vary among steps, if more than one step is involved in the reaction.

Also described in the present disclosure is the modification or functionalization of the compound. The compound may comprise the polymer backbone moiety, the linking group, the saccharide moiety, or the glycopolymer. The modification or functionalization of the compound may occur anytime in the process, such as, for example, prior to, during, or after the preparation of the glycopolymer.

Methods for Assessing Glycopolymer Activity

The activity of the compound provided herein can be assessed by a number of methods and assays. For example, the biological activity can be assessed in assays which test the activities of saccharide, such as chondroitin sulfate, keratan sulfate, heparin, dermatan sulfate, or heparan sulfate.

In some cases, the anti-inflammatory activity of the compound may be assessed. Methods and assays for testing the anti-inflammatory activity may include, measuring LPS-induced release of pro-inflammatory cytokines from macrophages (e.g. TNFα, IL-6, IF-γ), or neutrophils (see Examples below). Other relevant assays may comprise effects of lipoteichoic acid, zymosan, DNA, RNA, flagellin or peptidoglycan in the above systems as well as determination of regulation at the transcriptional level (e.g. Gene-array, qPCR etc). Furthermore, dendritic cell activation or activation of thrombocytes may also be used as a measure of anti-inflammatory activity. In some cases, the anti-inflammatory activity of the compound may be determined by assays which may characterize the binding specificities for chemokines Non-limiting examples of chemokines may include, but not limited to, CCL2, CCL3, CCL4, CCL5 (or RNATES), CCL7, CCL8, CCL11 (or eotaxin), CCL13, CCL14, CCL19, CCL20, CCL21, CCL22, CCL24, CCL25, CCL26, CCL27, CXCL-8, CXCL10, CXCL12, and CXCL13. In some cases, the tested compound may inhibit RANTES binding by up to about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%. In some cases, the compound may inhibit RANTES binding by a percentage between any of the two values described herein, for example, it may be in a range of 10%-100%, 20%-100%, 30%-100%, 40%-100%, 50%-100%, 60%-100%, 70%-100%, 80%-100%, or 90%-100%. In some examples, the compound may inhibit RANTES binding by up to about 80% as ascertained by an immunosorbent assay. In further examples, the compound may inhibit RANTES binding up to about 90% as ascertained by an immunosorbent assay.

In some cases, the compounds may be tested to determine an effective or an inhibitory concentration. In some cases, the compounds may be tested to determine a concentration at which a biological effect is modulated by a specified percentage relative to a control or a normal protein cell or tissue. For example, the compounds provided herein may be contacted with neuronal cells at varying concentrations to determine at what concentration outgrowth of neurites or axons is affected (e.g. enhanced or inhibited) by a specified percentage such as for example 40%, 50%, 60%, 70%, 80%, 90%, 95%, 97.5%, 99%, or 99.5%. Such a concentration is termed the effective concentration or the EC. The EC may further include the specified percentage. For example, an EC50 is the concentration at which a biological effect is modulated (e.g. enhanced or inhibited) by 50% by a compound. Similarly an IC50 is the concentration at which a biological effect is inhibited by a compound.

In some cases, the anti-coagulant activity of the compound described herein may be tested. Such activity may be determined by various methods and assays, for example, by using the activated partial thromboplastin time (APTT) test, prothrombin time (PT) test or the thrombin clotting time (TCT) test. An ability to increase the prothrombin time (PT), the thrombin clotting time (TCT) and/or the activated partial thromboplastin time (APTT) may signal the anti-coagulant activity of the tested compound. In some cases, the APTT of the compound can be equal to or more than about 0.01 s, 0.05 s, 0.1 s, 0.5 s, 1 s, 5 s, 10 s, 15 s, 20 s, 25 s, 30 s, 35 s, 40 s, 45 s, 50 s, 55 s, 60 s, 65 s, 70 s, 75 s, 80 s, 85 s, 90 s, 95 s, 100 s, 110 s, 120 s, 130 s, 140 s, 150 s, 160 s, 170 s, 180 s, 190 s, 200 s, 225 s, 250 s, 275 s, 300 s, 350 s, 400 s, 450 s, 500 s, 550 s, 600 s, 650 s, 700 s, 750 s, 800 s, 850 s, 900 s, 950 s or 1000 s, when ascertained by an assay. In some cases, the APTT of the compound may be in a range of any of the two values described herein. For example, the APTT may be between 0.01 s-1000 s, 0.1 s-1000 s, 0.5 s-1000 s, 1 s-1000 s, 5 s-1000 s, 10 s-1000 s, 20 s-1000 s, 50 s-1000 s, 100 s-1000 s, 200 s-1000 s, 300 s-1000 s, 400 s-1000 s, 500 s-1000 s, 600 s-1000 s, 700 s-1000 s, 800 s-1000 s, 900 s-1000 s, 0.01 s-500 s, 0.1 s-500 s, 0.5 s-500 s, 1 s-500 s, 5 s-500 s, 10 s-500 s, 50 s-500 s, 100 s-500 s, 200 s-500 s, 300 s-500 s, 400 s-500 s, 0.01 s-250 s, 0.1 s-250 s, 0.5 s-250 s, 1 s-250 s, 5 s-250 s, 10 s-250 s, 50 s-250 s, 100 s-250 s, 200 s-250 s, 0.01 s-100 s, 0.1 s-100 s, 0.5 s-100 s, 1 s-100 s, 5 s-100 s, 10 s-100 s, 25 s-100 s, 50 s-100 s, 75 s-100 s, 0.01 s-50 s, 0.1 s-50 s, 0.5 s-50 s, 1 s-50 s, 5 s-50 s, 10 s-50 s, 20 s-50 s, 30 s-50 s, 40 s-50 s, 0.01 s-25 s, 0.1 s-25 s, 0.5 s-25 s, 1 s-25 s, 5 s-25 s, 10 s-25 s, 15 s-25 s, 20 s-25 s, 0.01 s-10 s, 0.1 s-10 s, 0.5 s-10 s, 1 s-10 s, 2.5 s-10 s, 5 s-10 s, or 7.5 s-10 s. In some cases, the PT of the compound can be equal to or more than about 0.01 s, 0.05 s, 0.1 s, 0.5 s, 1 s, 5 s, 10 s, 15 s, 20 s, 25 s, 30 s, 35 s, 40 s, 45 s, 50 s, 55 s, 60 s, 65 s, 70 s, 75 s, 80 s, 85 s, 90 s, 95 s, 100 s, 110 s, 120 s, 130 s, 140 s, 150 s, 160 s, 170 s, 180 s, 190 s, 200 s, 225 s, 250 s, 275 s, 300 s, 350 s, 400 s, 450 s, 500 s, 550 s, 600 s, 650 s, 700 s, 750 s, 800 s, 850 s, 900 s, 950 s or 1000 s, when ascertained by an assay. In some cases, the PT of an effective anti-coagulant compound may be in a range of any of the two values described herein. For example, the PT may be between 0.01 s-10005, 0.1 s-1000 s, 0.5 s-1000 s, 1 s-1000 s, 5 s-1000 s, 10 s-1000 s, 20 s-1000 s, 50 s-1000 s, 100 s-1000 s, 200 s-1000 s, 300 s-1000 s, 400 s-1000 s, 500 s-1000 s, 600 s-1000 s, 700 s-1000 s, 800 s-1000 s, 900 s-10005, 0.01 s-500 s, 0.1 s-500 s, 0.5 s-500 s, 1 s-500 s, 5 s-500 s, 10 s-500 s, 50 s-500 s, 100 s-500 s, 200 s-5005, 300 s-500 s, 400 s-500 s, 0.01 s-250 s, 0.1 s-250 s, 0.5 s-250 s, 1 s-250 s, 5 s-250 s, 10 s-250 s, 50 s-250 s, 100 s-250 s, 200 s-250 s, 0.01 s-100 s, 0.1 s-100 s, 0.5 s-100 s, 1 s-100 s, 5 s-100 s, 10 s-100 s, 25 s-100 s, 50 s-1005, 75 s-100 s, 0.01 s-50 s, 0.1 s-50 s, 0.5 s-50 s, 1 s-50 s, 5 s-50 s, 10 s-50 s, 20 s-50 s, 30 s-50 s, 40 s-50 s, 0.01 s-25 s, 0.1 s-25 s, 0.5 s-25 s, 1 s-25 s, 5 s-25 s, 10 s-25 s, 15 s-25 s, 20 s-25 s, 0.01 s-10 s, 0.1 s-10 s, 0.5 s-10 s, 1 s-10 s, 2.5 s-10 s, 5 s-10 s, or 7.5 s-10 s. For example, when ascertained by an in vitro assay, the prolonged APTT and/or PT with the addition of a compound may indicate its anti-coagulant activity. In one example, the APTT and PT of the control (i.e., none of the compound is added) may be about 31.2 s and 13.3 s, respectively, when ascertained by an in vitro assay, any compound that may elevate the APTT and/or PT (e.g., with APTT longer than 31.2 s and PT longer than 13.3 s) as assessed by the same assay would bear the anticoagulant activity.

In some cases, the anti-coagulant activity of the compound may be assessed by determining its ability to enable the antithrombin III (or ATIII) to inhibit the serine proteases Factor Xa (FXa) and FIIa, through the binding of the compound to ATIII. FIIa is activated downstream of FXa in the coagulation cascade, and facilitates blood clotting by converting soluble fibrinogen to insoluble fibrin strands. By utilizing this type of assay, the anti-coagulant activity of tested compound may be quantified by IC50, as described elsewhere herein. The lower the IC50 value, the more potent the tested compound may be in reducing the blood coagulation. For example, when ascertained by an assay, a control sample (i.e., without the addition of tested compound) may have an anti-FXa IC50 and/or an anti-FIIa IC50 of about 2000 nM or more, and any compound that has the ability to lower either one of the IC50s compared to the control may have the anti-coagulant activity. In cases where more than one tested compound have the anti-coagulant activity, as discussed above, the one that has the lowest IC50 value may have the highest anti-coagulant activity.

In some cases, the compound may have an anti-FXa IC50 value equal to or less than about 3000 nM, 2000 nM, 1000 nM, 500 nM, 250 nM, 100 nM, 90 nM, 80 nM, 70 nM, 60 nM, 50 nM, 40 nM, 30 nM, 20 nM, 10 nM, 7.5 nM, 5 nM, 2.5 nM, 1 nM, 0.5 nM, 0.25 nM, 0.1 nM, 0.05 nM, 0.025 nM, 0.01 nM, 0.005 nM, 0.0025 nM, 0.001 nM, 0.0005 nM, 0.00025 nM, 0.0001 nM, 0.00005 nM, 0.000025 nM, 0.00001 nM, 0.000005 nM, 0.0000025 nM, or 0.000001 nM, when ascertained by an assay. In some cases, the compound may have an anti-FXa IC50 value between any two of the values described herein, for example, between 0.000001 nM-3000 nM, 0.000005 nM-3000 nM, 0.00001 nM-3000 nM, 0.00005 nM-3000 nM, 0.0001 nM-3000 nM, 0.0005 nM-3000 nM, 0.001 nM-3000 nM, 0.005 nM-3000 nM, 0.01 nM-3000 nM, 0.05 nM-3000 nM, 1 nM-3000 nM, 10 nM-3000 nM, 50 nM-3000 nM, 100 nM-3000 nM, 250 nM-3000 nM, 500 nM-3000 nM, 1000 nM-3000 nM, 2000 nM-3000 nM, 0.000001 nM-2000 nM, 0.000005 nM-2000 nM, 0.00001 nM-2000 nM, 0.00005 nM-2000 nM, 0.0001 nM-2000 nM, 0.0005 nM-2000 nM, 0.001 nM-2000 nM, 0.005 nM-2000 nM, 0.01 nM-2000 nM, 0.05 nM-2000 nM, 1 nM-2000 nM, 10 nM-2000 nM, 50 nM-2000 nM, 100 nM-2000 nM, 250 nM-2000 nM, 500 nM-2000 nM, 1000 nM-2000 nM, 0.000001 nM-1000 nM, 0.000005 nM-1000 nM, 0.00001 nM-1000 nM, 0.00005 nM-1000 nM, 0.0001 nM-1000 nM, 0.0005 nM-1000 nM, 0.001 nM-1000 nM, 0.005 nM-1000 nM, 0.01 nM-1000 nM, 0.05 nM-1000 nM, 1 nM-1000 nM, 10 nM-1000 nM, 50 nM-1000 nM, 100 nM-1000 nM, 250 nM-1000 nM, 500 nM-1000 nM, 750 nM-1000 nM, 0.000001 nM-500 nM, 0.000005 nM-500 nM, 0.00001 nM-500 nM, 0.00005 nM-500 nM, 0.0001 nM-500 nM, 0.0005 nM-500 nM, 0.001 nM-500 nM, 0.005 nM-500 nM, 0.01 nM-500 nM, 0.05 nM-500 nM, 1 nM-500 nM, 10 nM-500 nM, 50 nM-500 nM, 100 nM-500 nM, 250 nM-500 nM, 0.000001 nM-250 nM, 0.000005 nM-250 nM, 0.00001 nM-250 nM, 0.00005 nM-250 nM, 0.0001 nM-250 nM, 0.0005 nM-250 nM, 0.001 nM-250 nM, 0.005 nM-250 nM, 0.01 nM-250 nM, 0.05 nM-250 nM, 1 nM-250 nM, 10 nM-250 nM, 50 nM-250 nM, 100 nM-250 nM, 125 nM-250 nM, 0.000001 nM-100 nM, 0.000005 nM-100 nM, 0.00001 nM-100 nM, 0.00005 nM-100 nM, 0.0001 nM-100 nM, 0.0005 nM-100 nM, 0.001 nM-100 nM, 0.005 nM-100 nM, 0.01 nM-100 nM, 0.05 nM-100 nM, 1 nM-100 nM, 10 nM-100 nM, 25 nM-100 nM, 50 nM-100 nM, 75 nM-100 nM, 500 nM-0.000001 nM-50 nM, 0.000005 nM-50 nM, 0.00001 nM-50 nM, 0.00005 nM-50 nM, 0.0001 nM-50 nM, 0.0005 nM-50 nM, 0.001 nM-50 nM, 0.005 nM-50 nM, 0.01 nM-50 nM, 0.05 nM-50 nM, 1 nM-50 nM, 10 nM-50 nM, 25 nM-50 nM, 0.000001 nM-10 nM, 0.000005 nM-10 nM, 0.00001 nM-10 nM, 0.00005 nM-10 nM, 0.0001 nM-10 nM, 0.0005 nM-10 nM, 0.001 nM-10 nM, 0.005 nM-10 nM, 0.01 nM-10 nM, 0.05 nM-10 nM, 1 nM-10 nM, 2.5 nM-10 nM, 5 nM-10 nM, 7.5 nM-10 nM, 0.000001 nM-1 nM, 0.000005 nM-1 nM, 0.00001 nM-1 nM, 0.00005 nM-1 nM, 0.0001 nM-1 nM, 0.0005 nM-1 nM, 0.001 nM-1 nM, 0.005 nM-1 nM, 0.01 nM-1 nM, 0.05 nM-1 nM, 0.1 nM-1 nM, 0.25 nM-1 nM, 0.5 nM-1 nM, or 0.75 nM-1 nM.

In some cases, the compound may have an anti-FIIa IC50 value equal to or less than about 3000 nM, 2000 nM, 1000 nM, 500 nM, 250 nM, 100 nM, 90 nM, 80 nM, 70 nM, 60 nM, 50 nM, 40 nM, 30 nM, 20 nM, 10 nM, 7.5 nM, 5 nM, 2.5 nM, 1 nM, 0.5 nM, 0.25 nM, 0.1 nM, 0.05 nM, 0.025 nM, 0.01 nM, 0.005 nM, 0.0025 nM, 0.001 nM, 0.0005 nM, 0.00025 nM, 0.0001 nM, 0.00005 nM, 0.000025 nM, 0.00001 nM, 0.000005 nM, 0.0000025 nM, or 0.000001 nM, when ascertained by an assay. In some cases, the anti-FIIa IC50 of the compound may be between any of the two values described herein, for example, between 0.000001 nM-3000 nM, 0.000005 nM-3000 nM, 0.00001 nM-3000 nM, 0.00005 nM-3000 nM, 0.0001 nM-3000 nM, 0.0005 nM-3000 nM, 0.001 nM-3000 nM, 0.005 nM-3000 nM, 0.01 nM-3000 nM, 0.05 nM-3000 nM, 1 nM-3000 nM, 10 nM-3000 nM, 50 nM-3000 nM, 100 nM-3000 nM, 250 nM-3000 nM, 500 nM-3000 nM, 1000 nM-3000 nM, 2000 nM-3000 nM, 0.000001 nM-2000 nM, 0.000005 nM-2000 nM, 0.00001 nM-2000 nM, 0.00005 nM-2000 nM, 0.0001 nM-2000 nM, 0.0005 nM-2000 nM, 0.001 nM-2000 nM, 0.005 nM-2000 nM, 0.01 nM-2000 nM, 0.05 nM-2000 nM, 1 nM-2000 nM, 10 nM-2000 nM, 50 nM-2000 nM, 100 nM-2000 nM, 250 nM-2000 nM, 500 nM-2000 nM, 1000 nM-2000 nM, 0.000001 nM-1000 nM, 0.000005 nM-1000 nM, 0.00001 nM-1000 nM, 0.00005 nM-1000 nM, 0.0001 nM-1000 nM, 0.0005 nM-1000 nM, 0.001 nM-1000 nM, 0.005 nM-1000 nM, 0.01 nM-1000 nM, 0.05 nM-1000 nM, 1 nM-1000 nM, 10 nM-1000 nM, 50 nM-1000 nM, 100 nM-1000 nM, 250 nM-1000 nM, 500 nM-1000 nM, 750 nM-1000 nM, 0.000001 nM-500 nM, 0.000005 nM-500 nM, 0.00001 nM-500 nM, 0.00005 nM-500 nM, 0.0001 nM-500 nM, 0.0005 nM-500 nM, 0.001 nM-500 nM, 0.005 nM-500 nM, 0.01 nM-500 nM, 0.05 nM-500 nM, 1 nM-500 nM, 10 nM-500 nM, 50 nM-500 nM, 100 nM-500 nM, 250 nM-500 nM, 0.000001 nM-250 nM, 0.000005 nM-250 nM, 0.00001 nM-250 nM, 0.00005 nM-250 nM, 0.0001 nM-250 nM, 0.0005 nM-250 nM, 0.001 nM-250 nM, 0.005 nM-250 nM, 0.01 nM-250 nM, 0.05 nM-250 nM, 1 nM-250 nM, 10 nM-250 nM, 50 nM-250 nM, 100 nM-250 nM, 125 nM-250 nM, 0.000001 nM-100 nM, 0.000005 nM-100 nM, 0.00001 nM-100 nM, 0.00005 nM-100 nM, 0.0001 nM-100 nM, 0.0005 nM-100 nM, 0.001 nM-100 nM, 0.005 nM-100 nM, 0.01 nM-100 nM, 0.05 nM-100 nM, 1 nM-100 nM, 10 nM-100 nM, 25 nM-100 nM, 50 nM-100 nM, 75 nM-100 nM, 500 nM-0.000001 nM-50 nM, 0.000005 nM-50 nM, 0.00001 nM-50 nM, 0.00005 nM-50 nM, 0.0001 nM-50 nM, 0.0005 nM-50 nM, 0.001 nM-50 nM, 0.005 nM-50 nM, 0.01 nM-50 nM, 0.05 nM-50 nM, 1 nM-50 nM, 10 nM-50 nM, 25 nM-50 nM, 0.000001 nM-10 nM, 0.000005 nM-10 nM, 0.00001 nM-10 nM, 0.00005 nM-10 nM, 0.0001 nM-10 nM, 0.0005 nM-10 nM, 0.001 nM-10 nM, 0.005 nM-10 nM, 0.01 nM-10 nM, 0.05 nM-10 nM, 1 nM-10 nM, 2.5 nM-10 nM, 5 nM-10 nM, 7.5 nM-10 nM, 0.000001 nM-1 nM, 0.000005 nM-1 nM, 0.00001 nM-1 nM, 0.00005 nM-1 nM, 0.0001 nM-1 nM, 0.0005 nM-1 nM, 0.001 nM-1 nM, 0.005 nM-1 nM, 0.01 nM-1 nM, 0.05 nM-1 nM, 0.1 nM-1 nM, 0.25 nM-1 nM, 0.5 nM-1 nM, or 0.75 nM-1 nM.

Alternative methods may also involve some specific measurements of prekallikrein activation or the activity of Factor X and other coagulation factors may be performed to assess the anti-coagulant activity of the compound. Additionally, peripheral blood mononuclear cells (PBMNC)s can be stimulated by *E. coli* LPS with or without the compound and tissue factor and clot formation followed after addition of human plasma, or clotting times for whole blood can be measured. In some cases, the compounds may be tested for their ability to bind proteins known to be or suspected of being involved in interactions with naturally occurring molecules. For example, the compounds may be tested for their concentration dependent binding abilities and/or specificities for proteins such as chemokines, tumor necrosis factor a, and midkine. Other exemplary proteins that bind glycosaminoglycans are provided in the following table:

TABLE 1

Exemplary Proteins that Bind to Glycosaminoglycans

| Class | Examples | Physiological/pathophysiological effects of binding multiple |
|---|---|---|
| Enzymes | glycosaminoglycan biosynthetic enzymes, thrombin and coagulation factors (proteases), complement proteins (esterases), extracellular superoxide dismutase, topoisomerase | |
| Enzyme inhibitors | antithrombin III, heparin cofactor II, secretory leukocyte proteinase inhibitor, Cl-esterase inhibitor | coagulation, inflammation, complement regulation |
| Cell adhesion proteins | P-selectin, L-selectin, some integrins | cell adhesion, inflammation, metastasis |
| Extracellular matrix proteins | laminin, fibronectin, collagens, thrombospondin, vitionectin, tenascin | cell adhesion, matrix organization |
| Chemokines | platelet factor IV, ry-interferon, interleukins | chemotaxis, signaling, inflammation |
| Growth factors | fibroblast growth factors, hepatocyte growth factor, vascular endothelial growth factor, insulin-like growth factor-binding proteins, TGF-13-binding proteins | mitogenesis, cell migration |
| Morphogens | hedgehogs, TGF-0 family members | cell specification, tissue differentiation, development |
| Tyrosine-kinase growth factor receptors | fibroblast growth factor receptors, vascular endothelium growth factor receptor | mitogenesis |
| Lipid-binding proteins | apolipoproteins E and B, lipoprotein lipase, hepatic lipase, annexins | lipid metabolism, cell membrane functions |
| Plaque proteins | prion proteins, amyloid protein | plaque formation |
| Nuclear proteins | histones, transcription factors | unknown |
| Pathogen surface proteins | malaria cirumsporozoite protein | pathogen infections |
| Viral envelope proteins | herpes simplex virus, dengue virus, human immunodeficiency virus, hepatitis C virus | viral infections |

Methods of Treatment

The present disclosure also provides methods for preventing, reducing or treating a variety of diseases, disorders or conditions in a subject or a biological source (e.g., a blood population) of a subject by administering the compounds to the subject or the source. In some cases, the methods may comprise administering to the subject a composition comprising a substantially homogeneous population of compounds. In some cases, the methods may comprise administering a pharmaceutical composition comprising a therapeutically effective amount of one or more of the compounds to the subject. The biological source may be in the subject, or may be isolated from the subject prior to the treatment.

The subject can be diagnosed or be at risk for developing or acquiring an inflammatory condition. The subject can be a human subject. Alternatively, the subject can be a non-human subject, including but not limited to a non-human primate such as a macaque, chimpanzee, gorilla, vervet, orangutan, baboon or any other non-human primate that can be used as a preclinical model. The non-human subject can be mammal, including but not limited to a mouse, rat, rabbit, pig, sheep, horse, bovine, goat, gerbil, hamster, guinea pig or any other mammal. The subject or biological source can be a non-mammalian vertebrate, for example, a higher vertebrate, or an avian, amphibian or reptilian species, or another subject or biological source. In some cases, the subject can be a transgenic animal. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

The compounds of the present disclosure may be useful for studying and/or treatment of a number of diseases and conditions. For example, in some cases, the compounds may be useful for the study of the patterning and/or growth of neurons, including neuronal cells from the CNS, brain, spinal cord, and peripheral nerves. In some embodiments, the compounds may be useful for the treatment of neurodegenerative diseases, neural development disorders, or injuries to neural tissues such as brain or spinal cord injuries. The methods of using the compounds may comprise contacting a cell or a tissue with a compound provided herein in an amount effective to modulate neuronal outgrowth. In some cases, the cell can be a neuronal cell. In some cases, the tissue can be a neuronal or nervous tissue. The tissue can be severed or injured. The method may be performed in vitro or in vivo.

In some cases, the compounds of the present disclosure may be used in an in vitro study of neuronal growth. Any variety of mammalian neuronal cells, including those from the brain, CNS, peripheral nerves and the like can be treated by the methods provided herein. In addition, the cells may be from any variety of mammalian species such as human, mouse, rat, and any other mammalian species including agricultural stock or non-domesticated animals, as described elsewhere herein.

In some cases, non-mammalian neuronal cells may be used to screen for compounds that affect neurite outgrowth, axon guidance, and/or neural cell viability. For example, teleosts may be used to study the effect of the compounds. The use of teleosts in the methods of the present disclosure to study neurite outgrowth has several advantages due to their small size, rapid development, ease of genetic and embryological manipulation, and transparency. The compounds of can be applied to teleosts topically, by injection, or in the liquid medium. The compounds can be applied to eggs, embryos, or adult teleosts. In some cases, the results of studies in teleosts may form the basis of future studies in mammalian or human subjects. In other cases, the methods of the present disclosure may provide for the study of the compounds in avian subjects such as but not limited to the use of a chicken embryo animal model.

In some cases, the compounds may be used to induce neuronal growth in cultured neurons, including but not limited to hippocampal neurons, dopaminergic neurons, motor neurons, sensory neurons, and dorsal root ganglion neurons. In certain embodiments, the compounds provided herein may be useful for inducing the growth of differentiated neural stem cells prior to implantation. In the case of Parkinson's disease, for instance, implanted tissue has promise as a replacement for dying dopaminergic neurons.

In some embodiments, the compounds of the present disclosure may affect axon guidance, nuerite outgrowth, neural proliferation, and/or neural cell viability. As neurons begin to assemble into recognizable structures, they can begin to extend elongated membrane-enclosed protrusions of cytoplasm that are called processes or neurites. Many of these neurites will eventually mature into dendrites or axons. These neurites grow toward tissues such as other regions of the nervous system or other structures on which the neurons will eventually form synapses or junctions with other tissues such as muscles or glands. These tissues are often referred to as targets of the neurons, and proper function of the nervous system depends on the proper connections between the neurons and their targets. In some cases, neurite outgrowth is guided by interaction between the neurons and molecules on the surface of cells or in the extracellular matrix of the tissues through which they grow. These physical interactions attract axons and neurites to grow in certain directions and avoid growing in other directions. In addition, there are diffusible molecules that are similarly attractive or repellent to neurite and/or axon growth.

Molecules that attract or repel neurite and/or axon growth may include but not limited to integrins, cadherins, IN-1, laminins, netrins, semaphorins, ephrins, BMPs, Wnts, hedgehog, FGFs, tenascins, proteoglycans, neurotransmitters, nerve growth factor, NCAM, L1, Slit proteins, fibronextin, Comm, Robo, DCC, Robo, Nogo, paxilin, retinoic acid, and glycosaminoglycans. Additionally, there are many known inhibitors or stimulators of neurite outgrowth that can be used to study neuronal patterning. Such compounds may include but not limited to Bis-I, K252a, okadaic acid, U0126, methyl-murcery, desamethasone, amphetamine, and vincristine. In some cases, antiproliferative compounds or neurotoxicants such as, for example, kinase inhibitors, inhibitors of tubulin polymerization, inhibitors of nucleic acid synthesis, inhibitors of metabolic pathways, cell cycle inhibitors, diphenhydramine, cadmium, lead, 5,5-diphenylhydantoin, and valproic acid can be used to inhibit neurite outgrowth, neuron proliferation, and/or neuron viability. Other antiproliferative compounds known to affect neural cell proliferation and/or viability may include but not limited to aphidicolin, hydroxyurea, cytosine arabinoside, 5-fluorouracil, and ochratoxin A.

The compounds of the present disclosure may be assayed individually for their effects on neurite outgrowth, neuron proliferation, and/or neuron viability, or they may be assayed in combination with other compounds or agents described in the present disclosure or in combination with other compounds known or suspected to affect neurons. The compounds may be tested for their ability to augment and/or mitigate the effect of other compounds on neurons. In some cases, the compounds provided herein may be administered in combination with tumor necrosis factor a (TNF-a), and/or nerve growth factor (NGF). In some cases, the compounds provided herein may interact with growth factors and cytokines such as but not limited to TNF-a, FGF, and NGF. In some cases, the compounds provided herein may be tested relative to one or more controls. Controls may include cells not contacted with the compounds of the present disclosure, or cells contacted with other compounds. In some cases, controls may be a value understood to be normal, that is not inhibited or enhanced. For example, neurons under the conditions tested may be known to exhibit neurite outgrowth to a specified degree or length. The compounds may be tested for their ability to induce or inhibit neurite outgrowth relative to that specified degree or length (i.e. relative to the control).

In some embodiments of the present disclosure, the compounds provided herein may be screened for their ability to induce neurite outgrowth. The methods may involve contacting a cultured neuron with a compound bearing one or more negatively charged groups (e.g. sulfates) and determining the increase in neurite length of a treated versus untreated control. In some cases, a compound of the present disclosure may inhibit neurite outgrowth when applied in solution to the neurons, but may induce neurite outgrowth when applied to a substratum. In some cases, the methods and compounds of the present invention may cause an increase in mean neurite length relative to an untreated cell between about 1% and about 50%. In other cases, the increase in mean neurite length is greater than about 1%, about 2%, about 5%, about 10%, about 15%, about 20%, about 25%, about 30%, about 35%, about 40%, about 45%, or greater than about 50%. In other cases, the increase in mean neurite length is greater than 10%, 20%, or 30% relative to an untreated cell.

In some embodiments, the compounds may be screened against neurons that exhibit various disease phenotypes. For example, superoxide dismutase or SOD1 mutant neurons develop an amyotrophic lateral sclerosis (ALS)-like phenotype. The compounds may be contacted with SOD1 mutant neurons and tested for their ability to inhibit the development of ALS. Similarly, the compounds may be tested against suitable model systems for Huntington's Disease, Parkinson's Disease, and Alzheimer's disease or any other neurodegenerative diseases including but not limited to Alexander's disease, Alper's disease, ataxia telangiectasia, Batten disease, bovine spongiform encephalopathy, Canavan disease, Cockayne syndrome, corticobasal degeneration, Creutzfeldt-Jakob disease, HIV-associated dementia, Kennedy's disease, Krabbe's disease, lewy body dementia, Machado-Joseph disease, multiple sclerosis, multiple system atrophy, narcolepsy, neuroborreliosis, Pelizaeus-Merzbacher Disease, peripheral neuropathy, Pick's disease, primary lateral sclerosis, prion diseases, Refsum's disease, Sandhoffs disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes dorsalis.

In some embodiments, the compounds of the present invention may be useful for the study and/or treatment of other diseases or conditions such as but not limited to osteoarthritis, spinal cord injury, neuronal injury, cancer, blood coagulation diseases or conditions, and deep vein thrombosis. It is known that growth factors involved in cancers interact with glycosaminoglycans such as but not limited to chondroitin and heparan sulfate. The methods of the present invention provide for the use of the compounds provided herein for modulation of cancer growth and/or progression.

The methods and compounds of the present disclosure can modulate the growth and/or proliferation of cancers, as well as cancer metastasis and angiogenesis, including but not limited to ductal carcinoma in duct tissue in a mammary gland, medullary carcinomas, colloid carcinomas, tubular carcinomas, inflammatory breast cancer; ovarian cancer, including epithelial ovarian tumors such as adenocarcinoma in the ovary and an adenocarcinoma that has migrated from the ovary into the abdominal cavity, uterine cancer, cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Mtillerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer In some embodiments, the pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments of the present disclosure the compounds may inhibit TNF-α and thus reduce inflammation. In some cases, this reduction in inflammation by the administration of compounds of the present disclosure may be useful for the treatment of inflammatory diseases including but not limited to chronic inflammatory disease such as arthritis, rheumatoid arthritis, atherosclerosis, and inflammatory bowel disease. Methods for assaying the effect of the compounds of the present invention on inflammation may include but not limited to a leukocyte adhesion assay, an NF-κB activation assay, a cytokine release assay, an elastase or tryptase release assay, a reactive oxygen species production and a reactive nitrogen species production assay.

In some embodiments, the compounds of the present disclosure may be useful for the enhancement of wound repair. The compounds of the present disclosure may be used as mimetics of the naturally occurring molecules to enhance wound repair. Compounds may be applied topically to a wound or integrated into a bandage or suture material. Methods for assaying wound healing may include but not limited to the scratch assay, the assay described in Rodriguez et al. Methods MOI Biol. 2005; 294:23-9, and the rodent ear-punch assay.

The methods and compounds of the present disclosure can modulate the growth and/or proliferation of neoplastic conditions, including but not limited to Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some cases, the methods may involve the treatment of solid tumors. Solid tumors may include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas may include colorectal cancers, renal-cell carcinoma, liver cancer, non-small cell carcinoma of the lung, and cancer of the small intestine. Additional exemplary solid tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In some cases, the methods may be used for detecting, preventing, reducing or treating coagulation disorders in the subject. Coagulation disorders deal with disruption of the body's ability to control blood clotting. Non-limiting examples of coagulation disorders may include Hemophilia, Hemophilia A, Hemophilia B, Hemophilia C, Christmas disease, Factor IX deficiency, Disseminated intravascular coagulation disorder, consumption coagulopathy, Thrombocytopenia, Von Willebrand's disease, Hypoprothrombinemia, Factor XI deficiency, Factor VII deficiency, and serum prothrombin conversion accelerator (SPCA) deficiency.

In some cases, the methods may comprise the treatment of autoimmune disorders. Examples of autoimmune disorders may include, but not limited to, Crohn's disease, ulcerative colitis, psoriasis, psoriatic arthritis, juvenile arthritis and ankylosing spondilitis, Other non-limiting examples of autoimmune disorders include autoimmune diabetes, multiple sclerosis, systemic lupus erythematosus (SLE), rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome. Undesirable immune response can also be associated with or result in, e.g., asthma, emphysema, bronchitis, psoriasis, allergy, anaphylaxis, auto-immune diseases, rhuematoid arthritis, graft versus host disease, transplantation rejection, lung injuries, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing. The methods of the invention can be further used to treat multiorgan failure.

In some cases, the methods can also be used for the treatment of disorders involving platelet aggregation or platelet adhesion, including but not limited to Bernard-Soulier syndrome, Glanzmann's thrombasthenia, Scott's syndrome, von Willebrand disease, Hermansky-Pudlak Syndrome, and Gray platelet syndrome.

In some cases, the compounds, compositions or pharmaceutical compositions may be used to prevent, reduce or treat an inflammatory condition. The inflammatory condition may be an acute systemic inflammatory disease or a chronic inflammatory disease. Examples of inflammatory conditions may include but not limited to systemic inflammatory response syndrome (SIRS), ARDS, sepsis, inflammatory bowel disease, inflammatory skin diseases, psoriasis, eczema, scleroderma severe sepsis, septic shock erysipelas, meningitis, arthritis, rheumatoid arthritis, toxic shock syndrome, diverticulitis, appendicitis, pancreatitis, cholecystitis, colitis, cellulitis, burn wound infections, pneumonia, urinary tract infections, postoperative infections, peritonitis cystic fibrosis, COPD and other pulmonary diseases, gastrointestinal disease including chronic skin and stomach ulcerations, atopic dermatitis, oral ulcerations, aphtous ulcers, genital ulcerations and inflammatory changes, parodontitis, eye inflammations including conjunctivitis and keratitis, external otitis, mediaotitis and genitourinary inflammations.

In some cases, the methods can be used for treating liver diseases (including diabetes), pancreatitis or kidney disease (including proliferative glomerulonephritis and diabetes-induced renal disease) or pain, neurological or neurodegenerative diseases (including, but not limited to, Alzheimer's disease, Huntington's disease, CNS trauma, and stroke).

In some cases, the methods can be used for the prevention of blastocyte implantation in a mammal skeletal muscle atrophy, skeletal muscle hypertrophy, leukocyte recruitment in cancer tissue, invasion metastasis, melanoma, sarcoma, acute and chronic bacterial and viral infections, sepsis, glomerulo sclerosis, glomerulo, nephritis, or progressive renal fibrosis.

As will be appreciated, compounds described in the present disclosure may be applied for the prevention and treatment for a specific type of disease (or condition) as noted above, or they may be used to prevent or treat a combination of diseases or conditions described in the present disclosure. For example, in some cases, the compounds may be used to treat only the inflammatory conditions in a subject. In some cases, the compounds may only be applicable in reducing the coagulation in a blood population of a subject. In some cases, the compounds disclosed herein may be useful both in treating the inflammatory conditions in a subject and reducing the coagulation in a blood population of a subject.

Compositions

I. General

One aspect of the present disclosure provides a composition comprising a substantially homogeneous population of one or more compounds disclosed elsewhere herein. By "substantially homogeneous" we mean the content or the concentration of compounds included in the composition exceeds a certain limit, for example, more than 50% (w/w).

In some cases, the concentration of one or more of the compounds may be about 100%, 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0:06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v. For example, the concentration of one or more of the compounds may be about 50%, 75%, 90% or 99% w/w, w/v or v/v.

In some cases, the concentration of one or more of the compounds may be less than about 100%, 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0:06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v. For example, the concentration of one or more of the compounds may be less than about 100%, 90%, 75% or 50% w/w, w/v or v/v.

In some case, the concentration of one or more of the compounds may be greater than 99.9999%, 99.999%, 99.99%, 99.9%, 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 15%, 10%, 5%, 2.5%, 1%, 0.5%, 0.25%, 0.1%, 0.05%, 0.025%, 0.01%, 0.005%, 0.0025%, 0.001%, 0.0005%, 0.00025%, or 0.0001% w/w, w/v, or v/v. For example, the concentration of one or more of the compounds may be greater than about 50%, 75%, 95% or 99% w/w, w/v or v/v.

In some cases, the concentration of one or more of the compounds may be in a range of any of the two values described herein. For example, the concentration may be from approximately 0.0001% to 100%, approximately 0.0001% to 90%, approximately 0.0001% to 80%, approximately 0.0001% to 70%, approximately 0.0001% to 60%, approximately 0.0001% to 50%, approximately 0.0001% to 40%, approximately 0.0001% to 30%, approximately 0.0001% to 20%, approximately 0.0001% to 10%, approximately 0.0001% to 5%, approximately 0.0001% to 2.5%, approximately 0.0001% to 1%, approximately 0.001% to 100%, approximately 0.001% to 90%, approximately 0.001% to 80%, approximately 0.001% to 70%, approximately 0.001% to 60%, approximately 0.001% to 50%, approximately 0.001% to 40%, approximately 0.001% to 30%, approximately 0.001% to 20%, approximately 0.001% to 10%, approximately 0.001% to 5%, approximately 0.001% to 2.5%, approximately 0.001% to 1%, approximately 0.01% to 100%, approximately 0.01% to 90%, approximately 0.01% to 80%, approximately 0.01% to 70%, approximately 0.01% to 60%, approximately 0.01% to 50%, approximately 0.01% to 40%, approximately 0.01% to 30%, approximately 0.01% to 20%, approximately 0.01% to 10%, approximately 0.01% to 5%, approximately 0.01% to 2.5%, approximately 0.01% to 1%, approximately 0.1% to 100%, approximately 0.1% to 90%, approximately 0.1% to 80%, approximately 0.1% to 70%, approximately 0.1% to 60%, approximately 0.1% to 50%, approximately 0.1% to 40%, approximately 0.1% to 30%, approximately 0.1% to 20%, approximately 0.1% to 10%, approximately 0.1% to 5%, approximately 0.1% to 2.5%, approximately 0.1% to 1%, approximately 1% to 100%, approximately 1% to 90%, approximately 1% to 80%, approximately 1% to 70%, approximately 1% to 60%, approximately 1% to 50%, approximately 1% to 40%, approximately 1% to 30%, approximately 1% to 20%, approximately 1% to 10%, approximately 1% to 5%, approximately 1% to 2.5 w/w, w/v or v/v.

The quantity of one or more of the compounds included in the composition may vary. In some cases, a large quantity of compounds may be used. In some cases, a small quantity of compounds may be used. In some cases, the quantity of compounds contained in the composition may be equal to or less than about 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g. For example, the quantity of one or more of the compounds included in may be equal to or less than about 5 g, 1 g, 0.5 g or 0.05 g.

In some cases, the quantity of compounds in the composition may be more than about 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g. For example, the quantity of one or more of the compounds in the composition may be more than about 0.0001 g, 0.05 g, 1 g or 2.5 g.

In some cases, the quantity of compounds in the composition may be in a range of any two of the values described herein. For example, a composition may comprise one or more of the compounds whose quantity is in the range of 0.0001-10 g, 0.0001-9 g, 0.0001-8 g, 0.0001-7 g, 0.0001-6 g, 0.0001-5 g, 0.0001-4 g, 0.0001-3 g, 0.0001-2 g, 0.0001-1 g, 0.0005-10 g, 0.0005-9 g, 0.0005-8 g, 0.0005-7 g, 0.0005-6 g, 0.0005-5 g, 0.0005-4 g, 0.0005-3 g, 0.0005-2 g, 0.0005-1 g, 0.001-10 g, 0.001-9 g, 0.001-8 g, 0.001-7 g, 0.001-6 g, 0.001-5 g, 0.001-4 g, 0.001-3 g, 0.001-2 g, 0.001-1 g, 0.005-10 g, 0.005-9 g, 0.005-8 g, 0.005-7 g, 0.005-6 g, 0.005-5 g, 0.005-4 g, 0.005-3 g, 0.005-2 g, 0.005-1 g, 0.01-10 g, 0.01-9 g, 0.01-8 g, 0.01-7 g, 0.01-6 g, 0.01-5 g, 0.01-4 g, 0.01-3 g, 0.01-2 g, 0.01-1 g, 0.05-10 g, 0.05-9 g, 0.05-8 g, 0.05-7 g, 0.05-6 g, 0.05-5 g, 0.05-4 g, 0.05-3 g, 0.05-2 g, 0.05-1 g, 0.1-10 g, 0.1-9 g, 0.1-8 g, 0.1-7 g, 0.1-6 g, 0.1-5 g, 0.1-4 g, 0.1-3 g, 0.1-2 g, 0.1-1 g, 0.5-10 g, 0.5-9 g, 0.1-8 g, 0.1-7 g, 0.1-6 g, 0.1-5 g, 0.1-4 g, 0.1-3 g, 0.1-2 g, 0.1-1 g, 0.5-10 g, 0.5-9 g, 0.5-8 g, 0.5-7 g, 0.5-6 g, 0.5-5 g, 0.5-4 g, 0.5-3 g, 0.5-2 g, 0.5-1 g, 1-10 g, 1-9 g, 1-8 g, 1-7 g, 1-6 g, 1-5 g, 1-4 g, 1-3 g, or 1-2 g.

II. Pharmaceutical Compositions and Methods of Administration

The present disclosure also provides pharmaceutical compositions. The pharmaceutical compositions are typically formulated to provide one or more compounds of the present disclosure as the active ingredient, or a pharmaceutically acceptable salt, ester, prodrug, solvate, hydrate or derivative thereof. The pharmaceutical composition may comprise a therapeutically effective amount of the compound of the present disclosure. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The pharmaceutical compositions can be administered alone or in combination with one or more other agents, which are also typically administered in the form of pharmaceutical compositions. In some cases, it may be desirable that the one or more of the compounds in the present disclosure and other agent(s) be mixed into a preparation or all components may be formulated into separate preparations to use them in combination separately or at the same time.

As will be appreciated, as the active ingredient, the concentration of one or more of the compounds contained in pharmaceutical compositions may vary. In some cases, a high concentration of compounds may be included. In some cases, a low concentration of compounds may be used. In some cases, the concentration of one or more of the compounds may be equal to or less than about 100%, 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0:06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v. For example, the concentration of one or more of the compounds may be equal to or less than about 50%, 75%, 90% or 99% w/w, w/v or v/v.

In some case, the concentration of one or more of the compounds may be greater than 99.9999%, 99.999%, 99.99%, 99.9%, 99%, 98.5%, 98%, 97.5%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, 2.5%, 1%, 0.5%, 0.25%, 0.1%, 0.05%, 0.025%, 0.01%, 0.005%, 0.0025%, 0.001%, 0.0005%, 0.00025%, or 0.0001% w/w, w/v, or v/v. For example, the concentration of one or more of the compounds may be greater than about 50%, 75%, 95% or 99% w/w, w/v or v/v.

In some cases, the concentration of one or more of the compounds may be in a range of any of the two values described herein. For example, the concentration may be from approximately 0.0001% to 100%, approximately 0.0001% to 90%, approximately 0.0001% to 80%, approximately 0.0001% to 70%, approximately 0.0001% to 60%, approximately 0.0001% to 50%, approximately 0.0001% to 40%, approximately 0.0001% to 30%, approximately 0.0001% to 20%, approximately 0.0001% to 10%, approximately 0.0001% to 5%, approximately 0.0001% to 2.5%, approximately 0.0001% to 1%, approximately 0.001% to 100%, approximately 0.001% to 90%, approximately 0.001% to 80%, approximately 0.001% to 70%, approximately 0.001% to 60%, approximately 0.001% to 50%, approximately 0.001% to 40%, approximately 0.001% to 30%, approximately 0.001% to 20%, approximately 0.001% to 10%, approximately 0.001% to 5%, approximately 0.001% to 2.5%, approximately 0.001% to 1%, approximately 0.01% to 100%, approximately 0.01% to 90%, approximately 0.01% to 80%, approximately 0.01% to 70%, approximately 0.01% to 60%, approximately 0.01% to 50%, approximately 0.01% to 40%, approximately 0.01% to 30%, approximately 0.01% to 20%, approximately 0.01% to 10%, approximately 0.01% to 5%, approximately 0.01% to 2.5%, approximately 0.01% to 1%, approximately 0.1% to 100%, approximately 0.1% to 90%, approximately 0.1% to 80%, approximately 0.1% to 70%, approximately 0.1% to 60%, approximately 0.1% to 50%, approximately 0.1% to 40%, approximately 0.1% to 30%, approximately 0.1% to 20%, approximately 0.1% to 10%, approximately 0.1% to 5%, approximately 0.1% to 2.5%, approximately 0.1% to 1%, approximately 1% to 100%, approximately 1% to 90%, approximately 1% to 80%, approximately 1% to 70%, approximately 1% to 60%, approximately 1% to 50%, approximately 1% to 40%, approximately 1% to 30%, approximately 1% to 20%, approximately 1% to 10%, approximately 1% to 5%, approximately 1% to 2.5% w/w, w/v or v/v.

The quantity of one or more of the compounds included in pharmaceutical compositions may vary. In some cases, a large quantity of compounds may be used. In some cases, a small quantity of compounds may be used. In some cases, the quantity of compounds contained in pharmaceutical compositions may be equal to or less than about 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g. For example, the quantity of one or more of the compounds contained in pharmaceutical compositions may be equal to or less than about 5 g, 1 g, 0.5 g or 0.05 g.

In some cases, the quantity of compounds contained in pharmaceutical compositions may be greater than about 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g. For example, the quantity of one or more of the compounds contained in pharmaceutical compositions may be greater than about 0.0001 g, 0.05 g, 1 g or 2.5 g.

In some cases, the quantity of compounds in pharmaceutical compositions may be in a range of any two of the values described herein. For example, a pharmaceutical composition may comprise one or more of the compounds whose quantity is in the range of 0.0001-10 g, 0.0001-9 g, 0.0001-8 g, 0.0001-7 g, 0.0001-6 g, 0.0001-5 g, 0.0001-4 g, 0.0001-3 g, 0.0001-2 g, 0.0001-1 g, 0.0005-10 g, 0.0005-9 g, 0.0005-8 g, 0.0005-7 g, 0.0005-6 g, 0.0005-5 g, 0.0005-4 g, 0.0005-3 g, 0.0005-2 g, 0.0005-1 g, 0.001-10 g, 0.001-9 g, 0.001-8 g, 0.001-7 g, 0.001-6 g, 0.001-5 g, 0.001-4 g, 0.001-3 g, 0.001-2 g, 0.001-1 g, 0.005-10 g, 0.005-9 g, 0.005-8 g, 0.005-7 g, 0.005-6 g, 0.005-5 g, 0.005-4 g, 0.005-3 g, 0.005-2 g, 0.005-1 g, 0.01-10 g, 0.01-9 g, 0.01-8 g, 0.01-7 g, 0.01-6 g, 0.01-5 g, 0.01-4 g, 0.01-3 g, 0.01-2 g, 0.01-1 g, 0.05-10 g, 0.05-9 g, 0.05-8 g, 0.05-7 g, 0.05-6 g, 0.05-5 g, 0.05-4 g, 0.05-3 g, 0.05-2 g, 0.05-1 g, 0.1-10 g, 0.1-9 g, 0.1-8 g, 0.1-7 g, 0.1-6 g, 0.1-5 g, 0.1-4 g, 0.1-3 g, 0.1-2 g, 0.1-1 g, 0.5-10 g, 0.5-9 g, 0.1-8 g, 0.1-7 g, 0.1-6 g, 0.1-5 g, 0.1-4 g, 0.1-3 g, 0.1-2 g, 0.1-1 g, 0.5-10 g, 0.5-9 g, 0.5-8 g, 0.5-7 g, 0.5-6 g, 0.5-5 g, 0.5-4 g, 0.5-3 g, 0.5-2 g, 0.5-1 g, 1-10 g, 1-9 g, 1-8 g, 1-7 g, 1-6 g, 1-5 g, 1-4 g, 1-3 g, or 1-2 g.

The pharmaceutical composition according to the disclosure may be effective over a wide dosage range. For example, in the treatment of adult humans, dosages from about 0.01 to about 1000 mg, from about 0.5 to about 100 mg, from about 1 to about 50 mg per day, and from about 5 to about 40 mg per day may be used. The exact dosage may depend upon, for example, the route of administration, the form in which the compound is administered, the subject to be treated, the body weight of the subject to be treated, and the preference and experience of the attending physician.

Provided in the present disclosure are a number of methods of administering pharmaceutical compositions described elsewhere herein to the subjects. Described below are non-limiting exemplary pharmaceutical compositions and methods for preparing the same.

A. Pharmaceutical Compositions for Oral Administration

In some embodiments, the invention provides a pharmaceutical composition for oral administration containing a compound of the disclosure, and a pharmaceutical excipient suitable for oral administration.

In some embodiments, the invention provides a solid pharmaceutical composition for oral administration comprising: (i) an effective amount of a compound of the disclosure; (ii) an effective amount of a second agent; and/or (iii) a pharmaceutical excipient suitable for oral administration. In some embodiments, the composition may further contain: (iv) an effective amount one or more of additional agents, e.g., a third agent.

In some embodiments, the pharmaceutical composition may be a liquid pharmaceutical composition suitable for oral consumption. Pharmaceutical compositions of the disclosure for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by a number of methods of pharmacy, but most, if not all methods may include the step of bringing the active ingredient into association with the carrier, which may constitute one or more necessary ingredients. In general, the compositions may be prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising one or more active ingredients, since water can facilitate the degradation of some ingredients. For example, water may be added (e.g., 5%) in the pharmaceutical arts as a method of simulating long-term storage in order to determine characteristics such as shelf-life or the stability of formulations over time Anhydrous pharmaceutical compositions and dosage forms of the disclosure can be prepared using anhydrous or low moisture containing ingredients and low moisture or low humidity conditions. Pharmaceutical compositions and dosage forms of the disclosure which may contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using a number of materials to prevent exposure to water such that they can be included in suitable formulary kits. Examples of suitable packaging may include, but are not limited to, hermetically sealed foils, plastic or the like, unit dose containers, blister packs, and strip packs.

An active ingredient can be combined in an intimate admixture with a pharmaceutical carrier according to various pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms may include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein may include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the disclosure to provide tablets that may disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a certain amount of disintegrant that is neither too little nor too much to detrimentally alter the release of the active ingredient(s) may be used to form the dosage forms of the glycopolymers disclosed herein. The amount of disintegrant used may vary based upon the type of formulation and mode of administration. About 0.5 to about 15 weight percent of disintegrant, or about 1 to about 5 weight percent of disintegrant, may be used in the pharmaceutical composition. Disintegrants that can be used to form pharmaceutical compositions and dosage forms of the disclosure may include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants may be used to form pharmaceutical compositions and dosage forms of the disclosure. Non-limiting examples of lubricants may include, but not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants may include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by a number of techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant can be used to form pharmaceutical compositions and dosage forms of the disclosure. Examples of surfactants may include, but not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

An empirical parameter used to characterize the relative hydrophilicity and hydrophobicity of non-ionic amphiphilic compounds is the hydrophilic-lipophilic balance ("HLB" value). A suitable hydrophilic surfactant may generally have an HLB value of at least about 10, while suitable lipophilic surfactants may generally have an HLB value of or less than about 10. Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Ionic surfactants may include, but not limited to, alkylammonium salts, fusidic acid salts, fatty acid derivatives of amino acids, oligopeptides, and polypeptides, glyceride derivatives of amino acids, oligopeptides, and polypeptides, lecithins and hydrogenated lecithins, lysolecithins and hydrogenated lysolecithins, phospholipids and derivatives thereof, lysophospholipids and derivatives thereof, carnitine fatty acid ester salts, salts of alkylsulfates, fatty acid salts, sodium docusate, acyl lactylates, mono- and diacetylated tartaric acid esters of mono- and di-glycerides, succinylated mono- and di-glycerides, citric acid esters of mono- and di-glycerides; and mixtures thereof.

Within the aforementioned group, ionic surfactants may include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants may include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Lipophilic surfactants may include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize the precipitation of the compound. A solubilizer may also be added to increase the solubility of the hydrophilic drug and/or other components, such as surfactants, or to maintain the composition as a stable or homogeneous solution or dispersion.

Examples of solubilizers may include, but are not limited to alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, $\epsilon$-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples may include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included may vary. In some cases, the amount of a given solubilizer may be limited to a bioacceptable amount. In some cases, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients may include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases may include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Additional examples of bases may be salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Acids may also be used in pharmaceutical compositions, such as pharmaceutically acceptable organic or inorganic acids. Examples of inorganic acids may include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

B. Pharmaceutical Compositions for Injection

The present invention also provides a pharmaceutical composition for injection comprising a compound of the disclosure and a pharmaceutical excipient suitable for injection. Components and amounts of agents in the compositions are as described herein.

The forms in which the pharmaceutical compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline may be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions may be prepared by incorporating the compound of the present invention in the required amount in the appropriate solvent with various other ingredients as enumerated above, as required, followed by filtered sterilization. Generally, dispersions may be prepared by incorporating the various sterilized active ingredients into a sterile vehicle which contains the basic dispersion medium and the required other ingredients from those enumerated above. In the case of sterile powders for the preparation of sterile injectable solutions, certain methods of preparation may be vacuum-drying and freeze-drying techniques which yield a powder of the active ingredient plus any additional desired ingredient from a previously sterile-filtered solution thereof.

C. Pharmaceutical Compositions for Topical (e.g., Transdermal) Delivery

In some embodiments, the disclosure provides a pharmaceutical composition for transdermal delivery containing a compound of the present disclosure and a pharmaceutical excipient for transdermal delivery.

Compositions of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions may also comprise suitable solid or gel phase carriers or excipients, which are compounds that allow increased penetration of, or assist in the delivery of, therapeutic molecules across the stratum corneum permeability barrier of the skin. Examples of such carriers and excipients may include, but not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present disclosure employs transdermal delivery devices ("patches"). Such transdermal patches may be used to provide continuous or discontinuous infusion of a compound of the present invention in controlled amounts, either with or without another agent.

D. Pharmaceutical Compositions for Inhalation

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described elsewhere herein. The compositions may be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

E. Pharmaceutical Compositions for Other Administration Methods

Pharmaceutical compositions may also be prepared from compositions described herein and one or more pharmaceutically acceptable excipients suitable for sublingual, buccal, rectal, intraosseous, intraocular, intranasal, epidural, or intraspinal administration. A number of methods may be used to prepare for such pharmaceutical compositions. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present disclosure can be effected by any method that enables delivery of the compounds to the site of action. These methods may include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

As described herein, the amount of the compound administered may be dependent upon, the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforementioned range may be more than adequate, while in other cases still larger doses may be employed without causing any harmful side effect, e.g. by dividing such larger doses into several small doses for administration throughout the day.

In some embodiments, a pharmaceutical composition may be administered in a single dose. In many cases, such administration may be by injection, e.g., intravenous injection, in order to introduce the agent quickly. However, other routes may be used as appropriate. A single dose of the pharmaceutical composition may also be used for treatment of an acute condition.

In some embodiments, a pharmaceutical composition may be administered in multiple doses. Dosing may be about once, twice, three times, four times, five times, six times, or more than six times per day. Dosing may be about once a month, once every two weeks, once a week, or once every other day. In some embodiments a composition and another agent may be administered together about once per day to about 6 times per day. In some embodiments the administration of a composition and an agent continues for less than about 7 days. In some embodiments the administration may continue for more than about 6, 10, 14, 28 days, two months, six months, or one year. In some embodiments, continuous dosing may be achieved and maintained as long as necessary.

Administration of the composition may continue as long as necessary. In some embodiments, a composition may be administered for more than 1, 2, 3, 4, 5, 6, 7, 14, or 28 days. In some embodiments, a composition may be administered for less than 28, 14, 7, 6, 5, 4, 3, 2, or 1 day. In some embodiments, a composition may be administered chronically on an ongoing basis, e.g., for the treatment of chronic effects.

An effective amount of a compound may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the disclosure may also be delivered via an impregnated or coated device such as a stent, or an artery-inserted cylindrical polymer. Such a method of administration may, for example, aid in the prevention or amelioration of restenosis following procedures such as balloon angioplasty. Without being bound by theory, a composition may slow or inhibit the migration and proliferation of smooth muscle cells in the arterial wall which contribute to restenosis. A composition may be administered, for example, by local delivery from the struts of a stent, from a stent graft, from grafts, or from the cover or sheath of a stent. In some embodiments, a composition may be admixed with a matrix. Such a matrix may be a polymeric matrix, and may serve to bond the compound to the stent. Polymeric matrices may include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Matrices may be degradable or nondegradable, releasing the ingredients. Glycopolymers may be applied to the surface of the stent by various methods such as dip/spin coating, spray coating, dip-coating, and/or brush-coating. The glycopolymers may be applied in a solvent and the solvent may be allowed to evaporate, thus forming a layer of compound onto the stent. Alternatively, the glycopolymers may be located in the body of the stent or graft, for example in microchannels or micropores. When implanted, the glycopolymer diffuses out of the body of the stent to contact the arterial wall. Such stents may be prepared by dipping a stent manufactured to contain such micropores or microchannels into a solution of the compound in a suitable solvent, followed by evaporation of the solvent. Excess drug on the surface of the stent may be removed via an additional brief solvent wash. In some embodiments, compound may be covalently linked to a stent or graft. A covalent linker may be used which may degrade in vivo, leading to the release of the compound of the invention. Any bio-labile linkage may be used for such a purpose, such as ester, amide or anhydride linkages. Compounds may additionally be administered intravascularly from a balloon used during angioplasty. Extravascular administration of the compounds via the pericard or via advential application of formulations of the disclosure may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

Kits

The present disclosure also provides kits. The kits include one or more compounds of the disclosure as described elsewhere herein, in packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals and studies involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Substrates

The present disclosure also contemplates many uses for glypolymers attached to, associated with, or immobilized on one or more substrates. In some embodiments, the substrate may include a solid support, such as a membrane, filter, microscope slide, microwell, array, tube, bead, bead array, or the like. The substrate may be made of various materials, including, but not limited to paper, cellulose, nylon, polystyrene, polycarbonate, plastics, glass, ceramic, stainless steel, or the like. In some cases, the substrate may have a rigid or semi-rigid surface. In some cases, the substrate may be spherical (e.g., bead) or substantially planar (e.g., flat surface) with appropriate wells, raised regions, etched trenches, or the like. In some cases, the substrate may include a gel or matrix in which glycopolymers may be embedded.

The substrate may be a part of, or in the form of a microparticle, nanoparticle, bandage, suture, catheter, stent, valve, pacemaker, implantable defibrillator, conduit, cannula, appliance, scaffold, central line (which may be a peripherally inserted central catheter (PICC or PIC line)), pessary, tube, drain, shunt, trochar, plug, or other implant or medical or surgical device. In some cases, the catheter may be a pulmonary artery, pericardial, pleural, urinary or intra-abdominal catheter. In some cases, the drain may be a cerebrospinal fluid drain. In some cases, the tube may be a tracheostomy, endotracheal or chest tube. In some other embodiments, the substrate may be a part of, or in the form of an implant, a rod (e.g. a spinal rod such as a posterior spinal rod), a plate, a screw, washer, wire, pin, internal fixation devices (e.g. fracture fixation devices), or other implantable orthopedic hardware known in the art.

Also provided in the present disclosure is that substrates may be flexible such that they may readily conform or bend to adopt a desired shape or configuration under conditions of use, or they may be rigid such that significant force may be required to cause an alteration in shape. In some embodiments the substrate may maintain its shape when supported at only one point or end. The surface could be substantially smooth or could be rough and/or comprise crevices.

EXAMPLES

Example 1: Synthesis and Characterization of Compounds

Exemplary methods of synthesizing the disaccharide compounds 5 and 15, and intermediates thereof, is shown in FIG. 2.

Methyl 3-O-benzyl-L-idopyranosyluronate (9)

Compound 9 was prepared in six steps from the commercially available diacetone glucose (Sigma Aldrich) using a number of procedures. (See e.g., Orgueira, H. A. et al., Chem. Eur. J. 2003, 9, 140; Lohman, G. J. S. et al., J. Org. Chem. 2003, 68, 7559). The analytical data were in agreement with the reported spectra.

Methyl 1,2,4-tri-O-acetyl-3-O-benzyl-β-L-idopyranosyluronate (10)

Compound 9 (0.30 g, 1.0 mmol) was added to $CH_2Cl_2$ (5.5 mL) at 0° C., and the solution was cooled to −40° C. 4-Dimethylaminopyridine (120 mg, 0.10 mmol) was added, followed by pyridine (700 µL, 10 mmol). Acetyl chloride (470 µL, 6.0 mmol) was then added dropwise to the reaction mixture, which was stirred for 10 h at −40° C. The reaction was quenched with aqueous $NaHCO_3$ (50 mL), extracted with $CH_2Cl_2$ (2.0×50 mL), and subsequently washed with $H_2O$, 1M $H_2SO_4$, and then $H_2O$ (50 mL for each wash). The combined organic layers were dried over $MgSO_4$ and concentrated under reduced pressure. Purification by silica gel flash chromatography (3:1 hexanes:EtOAc) afforded compound 10 (0.40 g) in quantitative yield. The analytical data were in agreement with previously reported spectra.[3] ESI-TOF HRMS: m/z calcd for $C_{20}H_{23}O_{10}$ [M+H]—$H_2$ 423.1286. found: 423.1286.

Methyl 4-O-acetyl-3-O-benzyl-β-L-idopyranuronate 1,2-(methyl-orthoacetate) (11)

$TiBr_4$ (8.1 g, 22 mmol) was added to a solution of compound 10 (6.9 g, 16 mmol) in $CH_2Cl_2$ (360 mL), and the reaction was stirred for 16 h at ambient temperature with exclusion of light. The reaction was quenched with ice-cold $H_2O$ (2.0×500 mL), filtered through Celite, and concentrated under reduced pressure. The resulting brown oil was immediately used in the next reaction without further purification. The crude bromide intermediate (16 mmol) was dissolved in $CH_2Cl_2$ (220 mL). 2,4,6-Collidine (11 mL, 80 mmol) and methanol (8.0 mL) were added to this solution, and the reaction was stirred for 14 h at room temperature (rt). The reaction mixture was then diluted with $CH_2Cl_2$ (500 mL), washed with aqueous $NaHCO_3$ and $H_2O$ (200 mL each), dried over $MgSO_4$, and concentrated under reduced pressure. Purification by silica gel flash chromatography (6:1 hexanes:EtOAc+1% $Et_3N$) afforded 11 (7.6 g, 75% over 2 steps) as a light yellow oil. $^1H$ NMR (500 MHz; $CDCl_3$): δ 7.44-7.30 (m, 5H, $OCH_2Ph$), 5.57 (d, J=2.7 Hz, 1H, H-1), 5.20 (dt, J=2.7, 1.3 Hz, 1H, H-4), 4.82 (d, J=11.7 Hz, 1H, $OCH_2Ph$), 4.69 (d, J=11.7 Hz, 1H, $OCH_2Ph$), 4.56 (d, J=1.4 Hz, 1H, H-5), 4.15 (dd, J=2.7, 1.9 Hz, 1H, H-3), 4.09 (ddd, J=2.9, 1.9, 1.2 Hz, 1H, H-2), 3.79 (s, 3H, $CO_2CH_3$), 3.26 (s, 3H, $OCH_3$), 2.05 (s, 3H, $OCOCH_3$), 1.74 (s, 3H, $CH_3$); $^{13}C$ NMR (125 MHz; $CDCl_3$): δ 170.1, 168.1, 136.8, 128.6, 128.4, 128.0, 96.6, 77.3, 76.1, 72.9, 71.3, 69.6, 68.9, 52.6, 49.1, 25.0, 20.1; ESI-TOF HRMS: m/z calcd for $C_{19}H_{23}O_9$ [M+H]—$H_2$ 395.1342. found: 395.1354.

Methyl 3-O-benzyl-β-L-idopyranuronate 1,2-(methyl-orthoacetate) (12)

Compound 11 (7.2 g, 18 mmol) was dissolved in methanol (90 mL) and cooled to −10° C. A 0.5 M solution NaOMe (1.8 mL, 0.91 mmol) was added, and the reaction mixture was stirred at −10° C. for 2 h and at 5° C. overnight. The solution was diluted with $CH_2Cl_2$ (200 mL) at 5° C., quenched with aqueous $NaHCO_3$ and $H_2O$ (500 mL each), and then extracted with (3.0×250 mL). The organic fractions were dried over $MgSO_4$ and concentrated under reduced pressure. Purification by silica gel flash chromatography (4:1→1:1 hexanes:EtOAc+1% $Et_3N$) yielded 12 (9.5 g, 80%) as a clear oil. $^1H$ NMR (500 MHz; $CDCl_3$): δ 7.36-7.34 (m, 5H, $OCH_2Ph$), 5.51 (d, J=2.4 Hz, 1H, H-1), 4.72 (d, J=11.7 Hz, 1H, $OCH_2Ph$), 4.62 (d, J=11.7 Hz, 1H, $OCH_2Ph$), 4.52 (s, 1H, H-4), 4.15-4.08 (m, 3H, H-2, H-5), 3.81 (s, 3H, $CO_2CH_3$), 3.30 (s, 3H, $OCH_3$), 2.78 (d, J=11.4 Hz, 1H, H-3), 1.76 (s, 3H, $CH_3$); $^{13}C$ NMR (125 MHz; $CDCl_3$): δ 168.3, 136.8, 128.7, 128.4, 127.9, 96.8, 75.8, 73.0, 72.9, 71.8, 67.0, 52.5, 50.3, 24.4; ESI-TOF HRMS: m/z calcd for $C_{17}H_{21}O_8$ [M+H]—$H_2$ 353.1236. found: 353.1226.

Methyl 3-O-benzyl-4-O-tert-butyldimethylsilyl-β-L-idopyranuronate 1,2-(methyl-orthoace-tate) (13)

Compound 12 (230 mg, 0.64 mmol) was dissolved in pyridine (7.8 mL) and the solution was cooled to −10° C. TBSOTf (1.5 mL, 0.65 mmol) was added, and the reaction was stirred overnight at 0° C. The reaction was diluted with $CH_2Cl_2$ (100 mL), quenched with aqueous $NaHCO_3$ (100 mL), and extracted with EtOAc (3.0×50 mL). The combined organic fractions were dried over $MgSO_4$ and concentrated under reduced pressure. Purification by silica gel flash chromatography (7:1 hexanes:EtOAc+1% $Et_3N$) yielded compound 13 (380 mg, 92%) as a clear oil. $^1H$ NMR (500 MHz; $CDCl_3$): δ 7.47 (m, 5H, $OCH_2Ph$), 5.62 (d, J=2.5 Hz, 1H, H-1), 4.80 (d, J=12 Hz, 1H, $OCH_2Ph$), 4.75 (d, J=12 Hz, 1H, $OCH_2Ph$), 4.51 (s, 1H, H-4), 4.21 (s, 1H, H-5), 4.20 (d, J=1 Hz, 1H, H-4), 3.98 (s, 1H, H-3), 3.89 (s, 3H, $CO_2CH_3$), 3.40 (s, 3H, $OCH_3$), 1.84 (s, 3H, $CH_3$), 0.94 (s, 9H, $SiC(CH_3)_3$), 0.08 (s, 3H, $SiCH_3$), 0.06 (s, 3H, $SiCH_3$); $^{13}C$ NMR (125 MHz; $CDCl_3$): δ 169.6, 137.0, 128.9, 128.6, 128.2, 124.6, 97.1, 76.3. 74.6, 72.8, 72.5, 67.9, 52.4, 49.5, 29.9, 25.7, 25.6, −4.4, −5.2; TOF HRMS ES m/z calcd for $C_{23}H_{36}O_8SiNa$ [M+Na]$^+$: 491.2077. found: 491.2070.

Methyl (dibutylphosphate-2-O-acetyl-3-O-benzyl-4-O-tert-butyldimethylsilyl-α-L-idopyra-nosid)uronate (6)

Compound 13 (140 mg, 0.29 mmol) was dissolved in $CH_2Cl_2$ (7.3 mL) at rt. Freshly activated 4 Å molecular sieves (290 mg) were added, and the solution was stirred for 15 min. Dibutylphosphate (0.54 mL, 2.9 mmol) was added slowly, and the reaction mixture was stirred overnight. After confirming that the reaction was complete by TLC, the reaction was quenched with triethylamine (2.0 mL) and concentrated under reduced pressure. Silica gel flash chromatography (5:1→3:1 hexanes:EtOAc+1% Et$_3$N) afforded the desired product (170 mg) in quantitative yield. $^1$H NMR (500 MHz; CDCl$_3$): δ 7.36-7.35 (m, 5H, OCH$_2$Ph), 5.82 (d, J=7.2 Hz, 1H, H-1), 4.97 (m, 1H, H-2), 4.86 (d, J=2.7 Hz, 1H, H-5), 4.78 (d, J=12 Hz, 1H, OCH$_2$Ph), 4.62 (d, J=12 Hz, 1H, OCH$_2$Ph), 4.09-3.99 (m, 5H, H-4, P(OCH$_2$CH$_2$CH$_3$)$_2$), 3.77 (s, 3H, CO$_2$CH$_3$), 3.62 (m, 1H, H-3), 2.04 (s, 3H, COCH$_3$), 1.64-1.60 (m, 4H, P(OCH$_2$CH$_2$CH$_3$)$_2$), 1.40-1.25 (m, 4H, P(OCH$_2$CH$_2$CH$_3$)$_2$), 0.96-0.88 (m, 6H, P(OCH$_2$CH$_2$CH$_3$)$_2$), 0.81 (s, 9H, SiC(CH$_3$)$_3$), 0.07 (s, 3H, SiCH$_3$), 0.17 (s, 3H, SiCH$_3$); $^{13}$C NMR (125 MHz; CDCl$_3$): δ 169.8, 169.2, 146.6, 137.3, 128.4, 128.0, 95.4, 73.8, 72.0, 68.0, 67.8, 67.0, 66.9, 52.1, 32.1, 25.4, 20.9, 18.6, 17.8, 13.5, −4.7, −5.7; ESI-TOF HRMS m/z calcd for C$_{30}$H$_{52}$O$_{11}$PSi [M+H]$^+$: 647.3017. found: 647.3001.

Methyl 2-O-acetyl-3-O-benzyl-4-O-tert-butyldimethylsilyl-α-L-idopyranosyluronate-(1→4)-tert-butyldimethylsilyl (2-azido-3-O-benzyl-6-O-levulinoyl-2-deoxy-β-D-glucopyranoside) (14)

Compound 6 (92 mg, 0.14 mmol) and 7 (77 mg, 0.17 mmol) were co-evaporated with toluene (3.0×1.0 mL) and placed under vacuum overnight. The mixture was dissolved in CH$_2$Cl$_2$ (4.2 mL), and freshly activated 4 Å molecular sieves (0.21 g) were added. After stirring at rt for 15 min, the temperature was lowered to −10° C. and the mixture stirred for an additional 15 min. TMSOTf (31 µL, 0.18 mmol) was added dropwise to the reaction mixture. The reaction was stirred at −30° C. for 30 min, quenched with Et$_3$N (1.0 mL), filtered through a silica pad, and concentrated under reduced pressure. Silica gel flash chromatography (5:1→4:1 hexanes:EtOAc) afforded the desired product (120 mg) in 93% yield. $^1$H NMR (600 MHz; CDCl$_3$): δ 7.37-7.24 (m, 10H, OCH$_2$Ph), 5.20 (d, J=4.2 Hz, 1H, H-1 of IdoA), 4.85 (t, J=4.1 Hz, 1H, H-2 of IdoA), 4.82 (d, J=10.6 Hz, 1H, OCH$_2$Ph), 4.74 (d, J=11.8 Hz, 1H, OCH$_2$Ph), 4.71 (d, J=10.8 Hz, 1H, OCH$_2$Ph), 4.69 (d, J=3.9 Hz, 1H, H-5 of IdoA), 4.64 (d, J=11.8 Hz, 1H, OCH$_2$Ph), 4.54 (dd, J=11.8, 2.1 Hz, 1H, H-1 of GlcN), 4.51-4.45 (m, 1H, H-6), 4.20-4.03 (m, 1H, H-6), 3.99 (t, J=4.3 Hz, 1H, H-4 of IdoA), 3.91-3.77 (m, 1H, H-4 of GlcN), 3.61 (t, J=4.3 Hz, 1H, H-3 of IdoA), 3.54 (s, 3H, CO$_2$CH$_3$), 3.48 (ddd, J=9.8, 5.9, 2.2 Hz, 1H, H-5 of GlcN), 3.37-3.24 (m, 2H, H-2 and H-3 of GlcN), 2.89-2.66 (m, 2H, COCH$_2$CH$_2$COCH$_3$), 2.61 (t, J=6.7 Hz, 2H, COCH$_2$CH$_2$COCH$_3$), 2.19 (s, 3H, COCH$_2$CH$_2$COCH$_3$), 2.00 (s, 3H, COCH$_3$), 0.92 (s, 9H, SiC(CH$_3$)$_3$), 0.81 (s, 9H, SiC(CH$_3$)$_3$), 0.13 (d, J=4.6 Hz, 6H, SiCH$_3$), −0.06 (s, 3H, SiCH$_3$), −0.12 (s, 3H, SiCH$_3$); $^{13}$C NMR (125 MHz; CDCl$_3$): δ 206.5, 172.2, 170.2, 169.9, 138.2, 137.7, 128.5, 128.1, 128.1, 127.9, 127.4, 97.6, 97.1, 80.6, 76.8, 76.5, 75.4, 74.8, 73.4, 72.7, 71.5, 69.9, 68.9, 68.5, 62.6, 51.7, 38.0, 29.9, 28.0, 25.6, 25.5, 20.9, 18.0, 17.8, −4.3, −4.7, −5.2, −5.5; ESI-TOF HRMS m/z calcd for C$_{46}$H$_{69}$N$_3$O$_{14}$Si$_2$ [M+Na]$^+$: 966.4216. found: 966.4211.

Methyl 2-O-acetyl-3-O-benzyl-4-O-tert-butyldimethylsilyl-α-L-idopyranosyluronate-(1→4)-2-azido-3-O-benzyl-1-O-(2-(2-((2S)-bicyclo[2.2.1]hept-5-en-2-yl-methoxy)ethoxy)ethyl)-6-O-levulinoyl-2-deoxy-α-D-glucopyranoside (5)

Compound 15 (37 mg, 60 µmol) and 8 (33 mg, 70 µmol) were co-evaporated with toluene (3.0×1.0 mL) and placed under vacuum overnight. The mixture was dissolved in CH$_2$Cl$_2$ (1.7 mL) and freshly activated 4 Å molecular sieves (80 mg) were added. After stirring at rt for 15 min, the temperature was lowered to −30° C. and the mixture stirred for an additional 15 min. TMSOTf (14 µL, 70 µmol) was added to dropwise to the reaction mixture. The reaction was stirred at −10° C. for 10 min, slowly raised to rt over 15 min, quenched with Et$_3$N (0.50 mL), filtered through a silica pad, and concentrated under reduced pressure. Silica gel flash chromatography (10:1→4:1→3:1 hexanes:EtOAc) afforded the desired product (35 mg) in 67% yield. $^1$H NMR (500 MHz; CDCl$_3$): δ 7.38-7.25 (m, 10H, OCH$_2$Ph), 6.07 (ddd, J=25.6, 5.7, 3.0 Hz, 2H, CH=CH of Nb), 5.19 (d, J=4.2 Hz, 1H, H-1 of IdoA), 4.89-4.79 (m, 2H, H-2 of IdoA, OCH$_2$Ph), 4.72-4.68 (m, 3H, H-5 of IdoA, OCH$_2$Ph), 4.64 (d, J=11.9 Hz, 1H, OCH$_2$Ph), 4.52 (dd, J=12.1, 2.2 Hz, 1H, H-6 of GlcN), 4.34 (d, J=7.9 Hz, 1H, H-1 of GlcN), 4.12 (dd, J=12.1, 2.2 Hz, 1H, H-6 of GlcN), 4.02-3.93 (m, 2H, H-4 of IdoA, OCH$_2$ of PEG linker), 3.87 (dd, J=9.8, 8.9 Hz, 1H, H-4 of GlcN), 3.82-3.55 (m, 5H, H-3 of IdoA, OCH$_2$ of PEG linker), 3.54 (s, 3H, CO$_2$CH$_3$), 3.53-3.29 (m, 5H, H-5 of GlcN, H-2 of GlcN, H-3 of GlcN, OCH$_2$ of PEG linker), 2.88-2.67 (m, 4H, CH—CH=CH of Nb, COCH$_2$CH$_2$COCH$_3$), 2.67-2.56 (m, 2H, COCH$_2$CH$_2$COCH$_3$), 2.19 (s, 3H, COCH$_2$CH$_2$COCH$_3$), 2.00 (s, 3H, OCOCH$_3$), 1.75-1.66 (m, 1H, CH of Nb), 1.39-1.15 (m, 4H, CH$_2$ of Nb), 0.81 (s, 9H, SiC(CH$_3$)), −0.06 (s, 3H, SiCH$_3$), −0.11 (s, 3H, SiCH$_3$); $^{13}$C NMR (125 MHz; CDCl$_3$): δ 136.6, 128.5, 128.2, 127.8, 102.2, 80.9, 76.8, 76.1, 75.0, 73.2, 72.9, 71.6, 70.7, 70.4, 66.0, 45.0, 43.6, 38.8, 38.0, 29.8, 28.1, 25.5; ESI-TOF HRMS m/z calcd for C$_{52}$H$_{73}$N$_3$O$_{16}$Si [M+Na]$^+$: 1046.4658. found: 1046.4670.

Methyl 2-O-acetyl-3-O-benzyl-4-O-tert-butyldimethylsilyl-α-L-idopyranosyluronate-(1→4)-2-azido-3-O-benzyl-6-O-levulinoyl-2-deoxy-β-D-glucopyranosyl trichloroacetimidate (15)

Compound 14 (840 mg, 0.89 mmol) was dissolved in THF (27 mL) and the solution was cooled to 0° C. 1M TBAF (1.2 mL, 1.2 mmol) and AcOH (60 µL, 1.1 mmol) were added simultaneously, and the reaction was stirred for 30 min at 0° C. The reaction was quenched with aqueous NaHCO$_3$ (10 mL), extracted with CH$_2$Cl$_2$ (2.0×10 mL), and subsequently washed with H$_2$O, 1M H$_2$SO$_4$, and then H$_2$O (10 mL for each wash). After concentrating under reduced pressure, the crude mixture (0.89 mmol) was dissolved in CH$_2$Cl$_2$ (27 mL) and cooled to 0° C. To the reaction mixture, trichloroacetonitrile (1.3 mL, 13 mmol) and DBU (26 µL, 0.18 mmol) were added. The reaction was stirred at 0° C. for 12 h, quenched with Et$_3$N (1.0 mL), and concentrated under reduced pressure. Silica gel flash chromatography (5:1→4:1→3:1 hexanes:EtOAc+1% Et$_3$N) afforded the desired product (770 mg) in 89% yield over two steps. $^1$H NMR (600 MHz; CDCl$_3$): δ 8.72 (s, 1H, OCNHCCl$_3$), 7.47-7.28 (m, 10H, OCH$_2$Ph), 6.37 (d, J=3.6 Hz, 1H, H-1 of IdoA), 5.24 (d, J=4.7 Hz, 1H, H-1 of GlcN), 4.96 (d, J=10.5 Hz, 1H, OCH$_2$Ph), 4.90 (t, J=4.4 Hz, 1H, H-2 of GlcN), 4.75 (d, J=11.7 Hz, 1H, OCH$_2$Ph), 4.71 (d, J=10.5 Hz, 1H, OCH$_2$Ph), 4.66 (d, J=11.8 Hz, 1H, OCH$_2$Ph), 4.63 (d, J=4.2 Hz, 1H, H-5 of GlcN), 4.52 (dd, J=12.3, 1.8 Hz, 1H, H-6 of GlcN), 4.13 (dd, J=12.3, 4.3 Hz, 1H, H-6 of GlcN), 4.08-3.98 (m, 3H, H-4 and H-5 of IdoA, H-4 of GlcN), 3.91 (dd, J=10.2, 8.5 Hz, 1H, H-3 of IdoA), 3.69 (dd, J=10.2, 3.6 Hz, 1H, H-2 of IdoA), 3.66-3.61 (m, 1H, H-3 of GlcN), 3.57 (s, 3H, CO$_2$CH$_3$), 2.89-2.69 (m, 2H, COCH$_2$CH$_2$COCH$_3$), 2.67-2.54 (m, 2H, COCH$_2$CH$_2$COCH$_3$), 2.18 (s, 3H, COCH$_2$CH$_2$COCH$_3$), 2.01 (s, 3H, COCH$_3$), 0.82 (d, J=2.5 Hz, 9H, SiC(CH$_3$)$_3$), −0.05 (s, 3H, SiCH$_3$), −0.09 (s, 3H, SiCH$_3$); $^{13}$C NMR (125 MHz; CDCl$_3$): δ 206.5, 172.1, 170.2, 170.0, 160.7, 137.7, 137.6, 128.7, 128.2, 128.1, 128.0, 127.9, 127.6, 97.7, 94.4, 78.2, 77.2, 76.7, 75.1, 75.0, 73.0, 72.0, 71.9, 70.2, 69.0, 62.8, 61.9, 51.7, 38.0, 29.9, 28.0, 25.5, 20.1, 17.8, 4.7, 5.4; ESI-TOF HRMS m/z calcd for C$_{42}$H$_{55}$N$_3$O$_{15}$SiCl$_3$ [M+Na]$^+$: 997.2366. found: 997.2415.

Example 2: Synthesis of Glycopolymers 1-4

Figure 3:
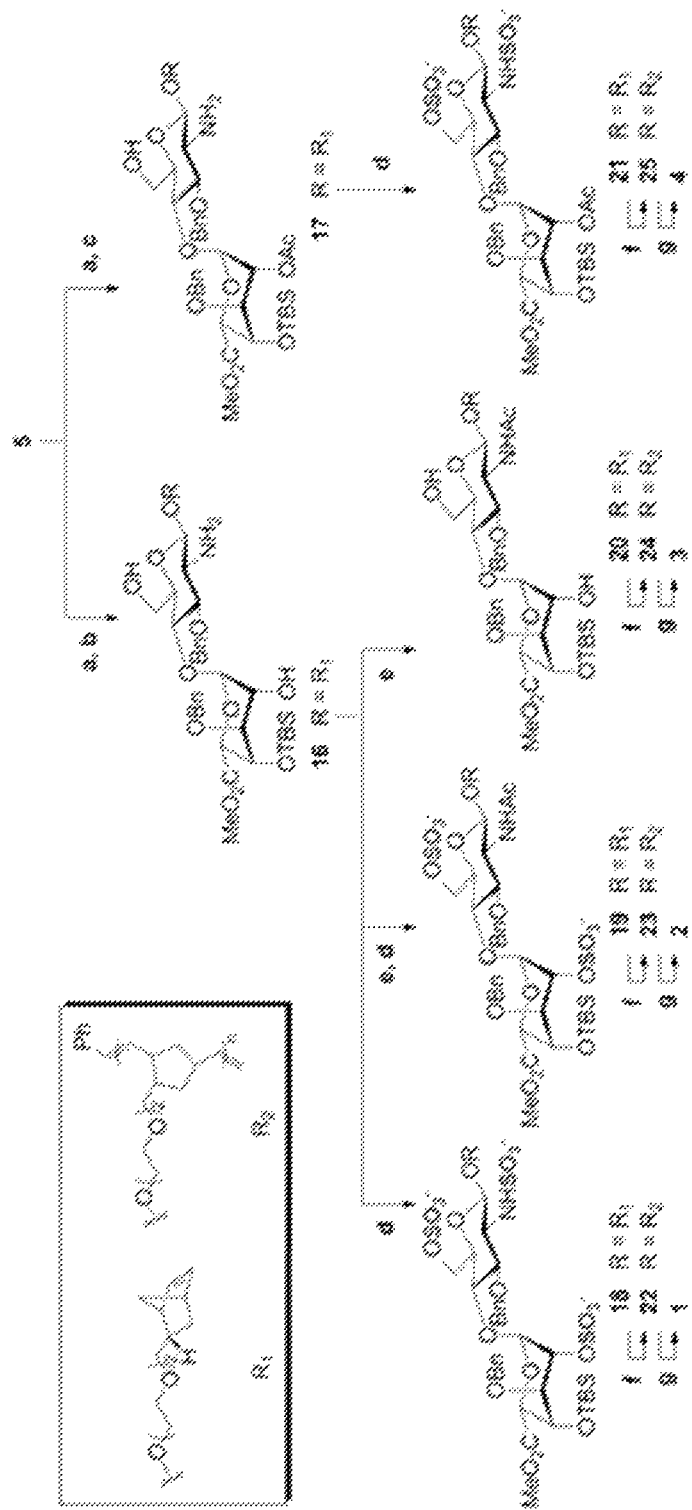
FIG. 3 provides a schematic illustration of an exemplary method for the synthesis of glycopolymers.

An exemplary method of synthesizing glycopolymers (1-4) from compound 5 is schematically illustrated in FIG. 3.

Methyl 3-O-benzyl-4-O-tert-butyldimethylsilyl-α-L-idopyranosyluronate-(1→4)-2-amino-3-O-benzyl-1-O-(2-(2-((2S)-bicyclo[2.2.1]hept-5-en-2-ylmethoxy)ethoxy)ethyl)-2-deoxy-α-D-glu-copyranoside (16)

Compound 5 (17 mg, 20 μmol) was dissolved in anhydrous MeOH (0.80 mL), and 1,3-propanedithiol (0.14 mL, 60 μmol) and DIPEA (0.12 mL, 60 μmol) were added dropwise. Upon confirmation of partial disappearance of 5 by TLC, flame-dried K$_2$CO$_3$ (2.4 mg, 20 μmol) was added and the reaction mixture was stirred for 24 h at rt. The reaction was quenched with Dowex 5W-X8 (H$^+$ form), filtered through a pad of Celite, and concentrated under reduced pressure. Silica gel flash chromatography (1:1 hexanes:EtOAc) afforded the desired product (14 mg) in 93% yield. $^1$H NMR (500 MHz; CDCl$_3$): δ 7.48-7.20 (m, 10H, OCH$_2$Ph), 6.17-5.88 (m, 2H, CH═CH of Nb), 5.25 (d, J=4.5 Hz, 1H, H-1 of IdoA), 4.96 (d, J=11.4 Hz, 1H, OCH$_2$Ph), 4.83 (d, J=11.4 Hz, 1H, OCH$_2$Ph), 4.68-4.51 (m, 3H, OCH$_2$Ph, H-5 of IdoA), 4.32 (d, J=8.0 Hz, 1H, H-1 of GlcN), 4.09-3.76 (m, 5H, H-6 of IdoA, H-4 of IdoA, H-2 of IdoA, OCH$_2$ of PEG linker), 3.76-3.53 (m, 10H, H-2 of IdoA, H-6 of IdoA, OCH$_2$ of PEG linker, CO$_2$CH$_3$), 3.47-3.32 (m, 4H, H-4 of GlcN, OCH$_2$ of PEG linker, H-5 of GlcN, H-3 of GlcN), 2.84-2.68 (m, 3H, H-2 of GlcN, CH—CH═CH of Nb), 1.69-1.63 (m, 1H, CH of Nb), 1.40-1.03 (m, 4H, CH$_2$ of Nb), 0.82 (s, 9H, SiC(CH$_3$)), −0.03 (d, J=7.3 Hz, 7H, SiCH$_3$); $^{13}$C NMR (125 MHz; CD$_3$OD): δ 171.7, 140.1, 139.7, 137.7, 137.5, 129.2, 128.8, 128.4, 104.5, 102.3, 84.1, 79.5, 77.7, 77.0, 75.2, 74.4, 72.8, 71.5, 71.4, 61.8, 57.8, 52.4, 45.8, 44.9, 42.8, 40.1, 30.6, 26.1, 18.7, −4.5, −5.1; ESI-TOF HRMS: m/z calcd for C$_{45}$H$_{66}$NO$_{13}$Si [M−H]$^-$ 856.4303. found: 856.4326.

Methyl 2-O-acetyl-3-O-benzyl-4-O-tert-butyldimethylsilyl-α-L-idopyranosyluronate-(1→4)-2-acetylamido-3-O-benzyl-1-O-(2-(2-((2S)-bicyclo[2.2.1]hept-5-en-2-ylmethoxy)ethoxy)eth-yl)-2-deoxy-α-D-glucopyranoside (17)

Compound 5 (190 mg, 0.18 mmol) was dissolved in anhydrous MeOH (11 mL). 1,3-propanedithiol (1.1 mL, 5.4 mmol) and DIPEA (1.1 mL, 6.3 mmol) were added dropwise, and the reaction mixture was stirred for 24 h at rt. The reaction was quenched with Dowex 5W-X8 (H$^+$ form), filtered through a pad of Celite, and concentrated under reduced pressure. Silica gel flash chromatography (30:2:1→20:2:1 EtOAc:MeOH:H$_2$O) afforded the desired product (150 mg) and the resulting intermediate was dissolved in pyridine (2.8 mL). To this mixture, a solution of hydrazine monohydrate (1.2 mmol) and AcOH (9.9 mmol) in pyridine (17 mL) was added at rt. The reaction was diluted with CH$_2$Cl$_2$ (10 mL), washed with cold water (15 mL), saturated NaHCO$_3$ (15 mL), water (15 mL), and saturated brine (15 mL). The combined organic fractions were dried over MgSO$_4$ and concentrated under reduced pressure. Silica gel flash chromatography (20:2:1 EtOAc:MeOH:H$_2$O) afforded the desired product (140 mg) in 87% yield over two steps. $^1$H NMR (500 MHz; CDCl$_3$): δ 7.46-7.27 (m, 10H, OCH$_2$Ph), 6.14-5.98 (m, 2H, CH═CH of Nb), 5.31 (d, J=4.4 Hz, 1H, H-1 of IdoA), 4.99 (d, J=11.2 Hz, 1H, OCH$_2$Ph), 4.88 (q, J=3.6 Hz, 1H, H-2 of IdoA), 4.80-4.68 (m, 2H, OCH$_2$Ph, H-5 of IdoA), 4.67-4.55 (m, 2H, OCH$_2$Ph), 4.36 (dt, J=8.0, 4.1 Hz, 1H, H-1 of GlcN), 4.05-3.85 (m, 4H, H-4 of IdoA, H-6 of GlcN, H-5 of GlcN, OCH$_2$ of PEG linker), 3.85-3.34 (m, 15H, OCH$_2$ of PEG linker, H-6 of GlcN, H-3 of IdoA, CO$_2$CH$_3$, H-3 of GlcN, H-4 of GlcN), 2.89 (dd, J=10.0, 7.8 Hz, 1H, H-2 of GlcN), 2.81-2.67 (m, 2H, CH—CH═CH of Nb), 2.01 (s, 3H, OCOCH$_3$), 1.42-1.14 (m, 5H, CH and CH$_2$ of Nb), 0.82 (s, 9H, SiC(CH$_3$)), −0.08 (d, J=7.3 Hz, 6H, SiCH$_3$); $^{13}$C NMR (125 MHz; CDCl$_3$): δ 170.2, 138.7, 137.8, 136.7, 128.5, 128.1, 127.9, 127.6, 97.8, 76.8, 76.2, 75.7, 75.5, 74.2, 72.7, 72.0, 70.7, 70.4, 69.3, 69.0, 61.7, 56.6, 51.9, 45.1, 43.8, 41.7, 38.9, 38.6, 29.9, 25.7, 21.1, 17.9, −4.5, −5.4; ESI-TOF HRMS: m/z calcd for C$_{47}$H$_{70}$NO$_{14}$Si [M−H]$^-$ 900.4565. found: 900.4568.

Methyl 3-O-benzyl-2-O-sulfonato-4-O-tert-butyldimethylsilyl-α-L-idopyranosyluronate-(1→4)-3-O-benzyl-1-O-(2-(2-((2S)-bicyclo[2.2.1]hept-5-en-2-ylmethoxy)ethoxy)ethyl)-2-deoxy-2-sulfonatamido-6-O-sulfonato-α-D-glucopyranoside (18)

Compound 16 (9.2 mg, 10 μmol) was dissolved in freshly distilled pyridine (1.0 mL) and to this SO$_3$.Py (50 mg, 0.32 mmol) and Et$_3$N (0.20 mL) were added. The reaction mixture was stirred at rt for 24 h, refluxed at 50° C. for 24 h, quenched with MeOH (1.0 mL), and concentrated to afford a golden syrup. Purification by Sephadex LH-20 gel filtration (1:1 CH$_2$Cl$_2$:MeOH), followed by silica gel flash chromatography (15:2:1→10:2:1→8:2:1 EtOAc:MeOH:H$_2$O) gave the desired product (8.7 mg) in 78% yield. $^1$H NMR (500 MHz; CD$_3$OD): δ 7.51-7.50 (m, 2H, OCH$_2$Ph), 7.43-7.41 (m, 2H, OCH$_2$Ph), 7.37-7.34 (m, 2H, OCH$_2$Ph), 7.30-7.26 (m, 3H, OCH$_2$Ph), 7.23-7.22 (m, 1H, OCH$_2$Ph), 6.11-6.04 (m, 2H, CH═CH of Nb), 5.30 (s, H-1 of IdoA), 4.98 (d, J=12.5 Hz, 1H, OCH$_2$Ph), 4.87 (d, J=11.5 Hz, 1H, OCH$_2$Ph), 4.78 (d, J=6 Hz, 1H, H-1 of GlcN), 4.67 (d, J=11.5 Hz, 1H, OCH$_2$Ph), 4.59 (d, J=12.5 Hz, 1H, OCH$_2$Ph), 4.43 (s, 1H, H-2 of IdoA), 4.37-4.28 (m, 2H, H-6, H-6 of GlcN), 4.13-4.12 (m, 1H, H-4 of GlcN), 4.05-4.03 (m, 1H, H-5 of GlcN), 3.96-3.93 (m, 1H, H-4 of IdoA), 3.81-3.78 (m, 2H, H-3 of IdoA, OCH$_2$ of PEG linker), 3.73-3.71 (m, 2H, OCH$_2$ of PEG linker), 3.69-3.56 (m, 5H, OCH$_2$ of PEG linker), 3.54-3.51 (m, 1H, H-2 of GlcN), 3.45-3.35 (m, 2H, OCH$_2$ of PEG linker), 3.15 (s, 3H, CO$_2$CH$_3$), 2.77 (s, 1H, CH—CH═CH of Nb), 2.72 (s, 1H, CH—CH═CH of Nb), 2.11 (s, 3H, OCOCH$_3$), 1.98 (s, 3H, OCOCH$_3$), 1.72-1.68 (m, 1H, CH of Nb), 1.38-1.21 (m, 3H, CH$_2$ of Nb), 1.15-1.12 (m, 1H, CH$_2$ of Nb), 0.76 (s, 9H, SiC(CH$_3$)), −0.17 (s, 3H, SiCH$_3$), −0.24 (s, 3H, SiCH$_3$); $^{13}$C NMR (125 MHz; CD$_3$OD): δ 172.8, 141.1, 140.4, 138.7, 131.6, 131.0, 130.6, 130.4, 130.3, 130.2, 130.0, 129.4, 104.3, 100.1, 80.9, 78.0, 77.0, 72.7, 72.4, 71.0, 70.7, 56.2, 53.5, 46.9, 46.0, 43.8, 41.1, 31.7, 27.4, 19.9, −3.0, −4.4;

ESI-TOF HRMS: m/z calcd for $C_{45}H_{66}NO_{22}S_3Si$ [M−H]⁻ 1016.2597. found: 1016.2583.

Methyl 2-O-sulfonato-3-O-benzyl-4-O-tert-butyldimethylsilyl-α-L-idopyranosyluronate-(1→4)-2-acetylamido-3-O-benzyl-1-O-(2-(2-((2S)-bicyclo[2.2.1]hept-5-en-2-ylmethoxy)ethoxy)ethyl)-2-deoxy-6-O-sulfonato-α-D-glucopyranoside (19)

To a solution of compound 16 (130 mg, 0.15 mmol) in anhydrous MeOH (8.4 mL) at ambient temperature were added Ac₂O (0.30 mL, 3.0 mmol) and Et₃N (0.50 mL). Additional amounts of Ac₂O (0.30 mL, 3.0 mmol) were added every hour until complete conversion to the desire product was observed by TLC (at least 4 h). The reaction mixture was directly loaded onto a Sephadex LH-20 gel filtration column and eluted with 1:1 $CH_2Cl_2$:MeOH. The N-acetylated intermediate was dissolved in freshly distilled pyridine (8.1 mL), and SO₃.Py (450 mg, 3.3 mmol) and Et₃N (1.6 mL) were added. The reaction mixture was stirred at rt for 24 h, refluxed at 50° C. for 24 h, quenched with MeOH (5.0 mL), and concentrated to afford a golden syrup. Purification by Sephadex LH-20 gel filtration (1:1 $CH_2Cl_2$:MeOH), followed by silica gel flash chromatography (10:2:1 EtOAc:MeOH:H₂O) gave the desired product (130 mg) in 85% yield over two steps. ¹H NMR (500 MHz; CD₃OD): δ 7.53-7.10 (m, 10H, OCH₂Ph), 6.12-5.95 (m, 2H, CH=CH of Nb), 5.35 (s, 1H, H-1 of IdoA), 4.84 (m, 2H, H-5 of IdoA, OCH₂Ph), 4.73 (d, J=11.2 Hz, 1H, OCH₂Ph), 4.60 (d, J=11.6 Hz, 1H, OCH₂Ph), 4.55 (d, J=8.3 Hz, 1H, H-1 of GlcN), 4.52 (dd, J=2.1, 1.1 Hz, 1H, H-2 of IdoA), 4.47 (d, J=11.2 Hz, 1H, OCH₂Ph), 4.41 (dd, J=11.3, 2.2 Hz, 1H, OCH₂ of PEG linker), 4.29 (dd, J=11.2, 5.0 Hz, 1H, OCH₂ of PEG linker), 4.00-3.87 (m, 4H, H-4 of IdoA, H-2 of GlcN, H-3 of GlcN, H-6 of GlcN), 3.86 (t, J=1.8 Hz, 1H, H-3 of IdoA), 3.79-3.48 (m, 11H, H-6 of GlcN, OCH₂ of PEG linker, H-4 of GlcN, H-5 of GlcN), 3.46-3.36 (m, 1H, OCH₂ of PEG linker), 3.33 (s, 3H, CO₂CH₃), 2.74 (d, J=31.6 Hz, 2H, CH—CH=CH of Nb), 1.85 (d, J=1.2 Hz, 3H, NHCOCH₃), 1.67 (d, J=4.5 Hz, 1H, CH of Nb), 1.39-1.04 (m, 4H, CH₂ of Nb), 0.78 (d, J=1.2 Hz, 9H, SiC(CH₃)), −0.11 (dd, J=47.6, 1.1 Hz, 6H, SiCH₃); ¹³C NMR (125 MHz; CD₃OD): δ 173.3, 172.1, 139.7, 139.2, 137.7, 137.5, 129.9, 129.5, 129.1, 128.6, 102.6, 99.2, 82.3, 77.1, 76.2, 75.7, 75.3, 74.1, 72.8, 71.5, 71.4, 70.1, 69.7, 67.8, 56.5, 52.4, 45.9, 44.9, 42.8, 40.0, 30.7, 26.2, 23.0, 18.9, −4.2, −5.4; ESI-TOF HRMS: m/z calcd for $C_{47}H_{67}NO_{20}NaSiS_2$ [M+Na]⁺ 1080.3365. found: 1080.3392.

Methyl 3-O-benzyl-4-O-tert-butyldimethylsilyl-α-L-idopyranosyluronate-(1→4)-2-acetyl-amido-3-O-benzyl-1-O-(2-(2-((2S)-bicyclo[2.2.1]hept-5-en-2-ylmethoxy)ethoxy)ethyl)-2-de-oxy-α-D-glucopyranoside (20)

To a solution of compound 16 (130 mg, 0.15 mmol) in anhydrous MeOH (8.4 mL) at ambient temperature were added Ac₂O (0.30 mL, 3.0 mmol) and Et₃N (0.50 mL). Additional amounts of Ac₂O (0.30 mL, 3.0 mmol) were added every hour until complete conversion to the desired product was observed by TLC (at least 4 h). Purification by Sephadex LH-20 gel filtration (1:1 $CH_2Cl_2$:MeOH), followed by silica gel flash chromatography (20:2:1 EtOAc:MeOH:H₂O) gave the desired product (140 mg) in quantitative yield. ¹H NMR (600 MHz; CDCl₃): δ 7.36-7.09 (m, 10H, OCH₂Ph), 6.12-5.87 (m, 2H, CH=CH of Nb), 5.11 (s, 1H, H-1 of IdoA), 4.76-4.72 (m, 1H, H-1 of GlcN), 4.70 (t, J=2.7 Hz, 1H, H-4 of IdoA), 4.68-4.56 (m, 2H, OCH₂Ph), 4.51-4.43 (m, 2H, OCH₂Ph), 4.00-3.92 (m, 1H, H-3 of IdoA), 3.91-3.80 (m, 2H, OCH₂ of PEG linker, H-6 of GlcN), 3.80-3.17 (m, 19H, H-6 of GlcN, H-2 of GlcN, H-3 of GlcN, H-4 of GlcN, H-5 of GlcN, H-2 of IdoA, H-5 of IdoA, OCH₂ of PEG linker, CO₂CH₃), 2.75-2.46 (m, 2H, CH—CH=CH of Nb), 1.67 (d, J=4.2 Hz, 3H, NHCOCH₃), 1.64-1.53 (m, 1H, CH of Nb), 1.30-1.13 (m, 4H, CH₂ of Nb), 0.71 (s, 9H, SiC(CH₃)), −0.15 (d, J=9.3 Hz, 6H, SiCH₃); ¹³C NMR (125 MHz; CDCl₃): δ 170.4, 169.7, 138.6, 137.5, 136.8, 136.6, 128.8, 128.4, 128.2, 127.4, 107.3, 101.6, 100.9, 78.7, 77.0, 76.4, 75.7, 75.5, 72.6, 72.5, 71.0, 70.7, 70.4, 69.8, 69.1, 68.8, 67.2, 62.7, 52.1, 45.2, 43.8, 41.7, 38.8, 30.0, 29.9, 25.6, 23.3, 17.9, −4.7, −5.4; ESI-TOF HRMS: m/z calcd for $C_{47}H_{69}NaNO_{14}Si$ [M+Na]⁺ 922.4380. found: 922.4385.

Methyl 2-O-acetyl-3-O-benzyl-4-O-tert-butyldimethylsilyl-α-L-idopyranosyluronate-(1→4)-3-O-benzyl-1-O-(2-(2-((2S)-bicyclo[2.2.1]hept-5-en-2-ylmethoxy)ethoxy)ethyl)-2-deoxy-2-sulfonatamido-6-O-sulfonato-α-D-glucopyranoside (21)

To a solution of compound 17 (22 mg, 0.020 mmol) in freshly distilled pyridine (2.3 mL) were added SO₃.Py (110 mg, 0.60 mmol) and Et₃N (0.5 mL). The reaction mixture was stirred at rt for 24 h and refluxed at 50° C. for 24 h, quenched with MeOH (1.0 mL), and concentrated to afford a golden syrup. Purification by Sephadex LH-20 gel filtration (1:1 $CH_2Cl_2$:MeOH), followed by silica gel flash chromatography (15:2:1→10:2:1 EtOAc:MeOH:H₂O) gave the desired product (26 mg) in 78% yield. ¹H NMR (600 MHz; CD₃OD): δ 7.79-7.03 (m, 10H, OCH₂Ph), 6.25-5.94 (m, 2H, CH=CH of Nb), 5.31 (d, J=4.4 Hz, 1H, H-1 of IdoA), 5.05-4.76 (m, 4H, H-2 of IdoA, H-5 of IdoA, OCH₂Ph), 4.75-4.64 (m, 1H, OCH₂Ph), 4.65-4.47 (m, 2H, OCH₂Ph, H-1 of GlcN), 4.38 (m, 1H, H-6 of GlcN), 4.20 (m, 1H, H-6 of GlcN), 4.07-3.85 (m, 4H, H-2 of IdoA, H-2 of GlcN, H-2 of GlcN, OCH₂ of PEG linker), 3.86-3.71 (m, 1H, OCH₂ of PEG linker), 3.71-3.45 (m, H, ¹H, H-3 of IdoA, H-3 of GlcN, H-5 of GlcN, OCH₂ of PEG linker), 3.40 (s, 3H, CO₂CH₃), 2.81-2.74 (m, 2H, CH—CH=CH of Nb), 2.07 (s, 3H, OCOCH₃), 1.52-1.10 (m, 5H, CH and CH₂ of Nb), 0.83 (s, 9H, SiC(CH₃)), −0.09 (s, 3H, SiCH₃), −0.13 (s, 3H, SiCH₃); ¹³C NMR (125 MHz; CDCl₃): δ 173.3, 172.0, 171.8, 139.8, 139.1, 137.7, 137.5, 102.8, 99.2, 82.1, 79.8, 77.1, 76.6, 76.2, 75.9, 75.3, 75.2, 73.2, 71.5, 71.4, 71.3, 71.0, 70.1, 69.8, 69.4, 67.3, 56.3, 52.4, 45.9, 44.9, 42.8, 40.0, 37.4, 36.0, 30.7, 23.0, 21.2, 18.7, −4.3, −5.4; ESI-TOF HRMS: m/z calcd for $C_{47}H_{67}NO_{20}NaSiS_2$ [M+Na]⁺ 1080.3365. found: 1080.3392.

Protected HS Glycopolymers (22-25)

Monomers 18-21 were converted into polymers 22-25, which contain the following functional groups: $R_1=SO_3^-$, $R_2=SO_3^-$, $R_3=SO_3^-$ (1); $R_1=SO_3^-$, $R_2=SO_3^-$, $R_3=AC$ (2); $R_1=H$, $R_2=H$, $R_3=Ac$ (3); $R_1=H$, $R_2=SO_3^-$, $R_3=SO_3^-$ (4). In a typical polymerization, a small vial was charged with monomer (18-21; 6.0 mg, 5.0 μmol) and a small stir bar under the flow of argon. To this was added degassed dichloroethane (DCE)/MeOH (10:1, 0.025 M) and bis-pyridine Grubbs catalyst (($H_2$IMes)(Py)₂(Cl)₂Ru=CHPh)⁴ in DCE (5 mg/mL stock solution, 24 μL, 0.11 μmol) by syringe at rt. The reaction mixture was stirred at rt for 1 h, quenched with ethyl vinyl ether (0.10 mL), and diluted with diethyl ether (1.0 mL) and hexanes (0.50 mL)

to obtain a white precipitate. The mixture was centrifuged to remove the organic layer, and the resulting white solid (83-98% conversion) was dried in vacuo. $^1$H NMR confirmed disappearance of the norbornene olefinic peaks at 6.04-6.11 ppm. The protected polymers were characterized by size exclusion chromatography multi-angle light scattering (SEC-MALS) using a system equipped with an MZ-Gel SDplus organic column (10E5 Å, MZ Analysentechnik), a light scattering detector (miniDAWN, Wyatt Technology), and a refractive index detector (TREOS, Wyatt Technology), and 0.2 M LiBr in DMF as the mobile phase. $^1$H NMR (500 MHz; D$_2$O): δ 7.49-7.15 (m, 10H), 5.42 (br, 1H), 5.18 (br, 1H), 4.75 (br, 1H), 4.65-4.51 (m, 2H), 4.38 (br, 1H), 4.05-3.84 (m, 4H), 3.86 (br, 1H), 3.79-3.50 (m, 13H), 3.46 (br, 1H), 3.31 (br, 3H) 3.30-3.25 (m, 2H), 2.49 (br, 2H), 1.94 (br, 3H), 1.79-1.07 (m, 5H), 0.77 (br, 9H), −0.07 (br, 3H), −0.17 (br, 3H).

2-O-sulfonato-α-L-idopyranosyluronate-(1→4)-1-O-(2-(2-((2S)bicyclo[2.2.1]hept-5-en-2-ylmethoxy)ethoxy)ethyl)-2-deoxy-2-sulfonatamido-6-O-sulfonato-α-D-glucopyranoside (26)

Compound 18 (14 mg, 0.013 mmol) was dissolved in THF (1.3 mL), and TMSOK (33 mg, 0.26 mmol) was added to the reaction mixture. The reaction was stirred for 24 h at rt and quenched with MeOH (1.0 mL). The crude reaction mixture was loaded directly onto a Sephadex G-25 gel filtration column and eluted with 100% H$_2$O, and fractions were combined, lyophilized, and subjected to hydrogenation. The intermediate was dissolved in a 3:2 mixture of 80 mM phosphate buffered saline (2.4 mL, pH=7.0) and MeOH (0.80 mL). To this, Pd(OH)$_2$/charcoal (80 mg, 8× by weight of starting material) was added, and the reaction was carried out under 1 atm H$_2$ gas for 3 d. The reaction mixture was filtered using a vacuum filtration system (0.45 μm PES membrane, VWR) and desalted on a Sephadex G-25 column in 100% H$_2$O to obtain the desired product 60% yield after lyophilization. $^1$H NMR (500 MHz, D$_2$O) δ 5.24 (s, 1H, H-1 of IdoA), 4.83 (d, J=2.7 Hz, 1H, H-5 of IdoA), 4.73 (d, J=8.2 Hz, 1H, H-1 of GlcN), 4.44 (m, 1H, H-6 of GlcN), 4.34 (m, 2H, H-6 of GlcN, H-2 of IdoA), 4.10 (m, 2H, H-3 of IdoA, H-4 of IdoA), 4.01-3.71 (m, 11H, OCH$_2$ of PEG linker, H-3 of GlcN, H-4 of GlcN, H-5 of GlcN), 3.44-3.31 (m, 2H, OCH$_2$ of PEG linker, H-2 of GlcN), 2.28-2.20 (m, 2H, bridgehead CH$_2$ of Nb), 1.82 (s, 2H, CH$_2$ of Nb), 1.59 (s, 2H, CH$_2$ of Nb), 1.48-1.36 (m, 2H, CH of Nb), 1.27-1.19 (m, 2H, CH$_2$ of Nb), 1.08 (s, 1H, CH of Nb).

Deprotected HS Glycopolymers (1-4)

Polymers 22-25 were deprotected to obtain final polymers 1-4, which contain the following functional groups: R$_1$=SO$_3^-$, R$_2$=SO$_3^-$, R$_3$=SO$_3^-$ (1); R$_1$=SO$_3^-$, R$_2$=SO$_3^-$, R$_3$=Ac$^-$ (2); R$_1$=H, R$_2$=H, R$_3$=Ac (3); R$_1$=H, R$_2$=SO$_3^-$, R$_3$=SO$_3^-$ (4). In a typical reaction, polymer (11 mg, 10 μmol per unit) was dissolved in THF (1.0 mL), and TBAI (7.0 mg, 20 μmol) and TMSOK (25 mg, 0.20 mmol) were added. The reaction was stirred for 24 h at rt and quenched with MeOH (1.0 mL). The crude reaction mixture was loaded directly onto a Sephadex G-25 gel filtration column and eluted with 100% H$_2$O. The polymer-containing fractions were combined, lyophilized, and subjected to hydrogenation. In a typical hydrogenation reaction, the polymer from the previous reaction was dissolved in a 3:2 mixture of 80 mM phosphate buffered saline (0.9 mL, pH=7.0) and MeOH (0.60 mL). To this, Pd(OH)$_2$/charcoal (84 mg, 8× weight of polymer) was added, and the reaction was carried out under 1 atm H$_2$ gas for 3 d. Samples were filtered using a vacuum filtration system (0.45 μm PES membrane, VWR) and desalted on a Sephadex G-25 column in 100% H$_2$O to obtain the desired polymers in 35-55% yield after lyophilization. $^1$H NMR showed disappearance of the benzyl and methyl ester peaks at 7.79-7.03 ppm and 3.40 ppm, respectively. Deprotected polymers were characterized by SEC-MALS using a system equipped with an OHpak water column (SB-804 HQ, Shodex), a light scattering detector (miniDAWN, Wyatt Technology), and a refractive index detector (TREOS, Wyatt Technology), and 3 mM NaN$_3$ and 6 mM NaNO$_3$ in H$_2$O as the mobile phase. $^1$H NMR (500 MHz; D$_2$O): δ 5.03 (br, 1H), 4.44 (br, 1H), 4.25-4.20 (m, 1H), 4.18-4.11 (m, 2H), 3.92 (br, 1H), 3.84 (br, 2H), 3.75-3.40 (m, 12H), 3.34 (br, 1H), 3.19 (br, 1H), 1.91 (br, 3H), 1.72 (br, 1H), 1.48-0.88 (m, 6H).

Properties of synthesized glycopolymers (1-4) are listed in Table 2: wherein the number average molecular weight ($M_n$) and polydispersity index (PDI) were determined by size exclusion chromatography multi-angle light scattering (SEC-MALS).

TABLE 2

Properties of Glycopolymers

| Polymer | Monomer | mol % Catalyst | $M_n$ (g/mol) | PDI | n (DP) |
|---|---|---|---|---|---|
| 1 | 22 | 5 | 27,870 | 1.22 | 35 |
| 2 | 23 | 5 | 36,490 | 1.02 | 48 |
| 3 | 24 | 5 | 53,580 | 1.16 | 90 |
| 4 | 25 | 5 | 32,880 | 1.03 | 46 |

Example 3: Direct and Competitive Enzyme-Linked Immunosorbent Assay (ELISA)

A 96-well heparin-binding plate (BD Biosciences) was coated with 25 μg/mL of heparin (Neoparin) for 12 h at room temperature. Wells were rinsed with phosphate-buffered saline (PBS) and blocked with 10% fetal bovine serum (FBS) in PBS for 1 h at 37° C. For the direct ELISA, various concentrations of RANTES (0.50-1024 nM; R&D Systems) were serially diluted in 1% BSA in PBS and incubated in each well for 1.5 h at 37° C. For the competitive ELISA, RANTES (at 12 nM, the pre-determined EC50) was pre-incubated (3 h, 37° C.) with various concentrations of heparin (0.010-40 μg/mL) or glycopolymers 1-4 (0.10-180 μg/mL), and the co-mixture was added to the 96-well plate for 1.5 h at 37° C. Wells were washed three times with PBST (PBS+0.1% Tween-20), incubated with a mouse anti-RANTES antibody (R&D Systems) for 1 h at 37° C., washed three times with PBST, and incubated with a horseradish peroxidase (HRP)-conjugated anti-mouse IgG antibody (GE Healthcare Life Sciences) for 1 h at 37° C. After three washes with PBST, RANTES binding was detected using a 3,3',5,5'-tetramethylbenzidine (TMB) substrate kit (Thermo Scientific) according to the manufacturer's instructions. Fluorescence was measured at 450 nm using a Victor 3 plate reader (PerkinElmer). The half-maximal effective concentration (EC50) and half maximal inhibitory concentration (IC50) were calculated using KaleidaGraph software (Synergy). IC50 values reported in the paper are for both the mass and molar concentrations of antagonist. IC50 values were also corrected for ligand valence (Table 3) by calculating the mass percentage of the disaccharide epitope contributing to each disaccharide-norbornyl linker unit, and then dividing by the molecular weight of the disaccharide epitope.

TABLE 3

Half Maximal Inhibitory Concentration (IC50) for Antagonists of RANTES

| Antagonist | IC50 (μg/mL) | IC50 (nM) | IC50 (μg/mL of disac) | IC50 (μM of disac) |
|---|---|---|---|---|
| 1 | 9.3 ± 1.1 | 334 ± 39 | 6.8 ± 0.80 | 11.7 ± 1.4 |
| 2 | 31.1 ± 6.2 | 852 ± 170 | 21.8 ± 4.4 | 40.3 ± 8.0 |
| 4 | 58.0 ± 5.7 | 1760 ± 170 | 40.6 ± 4.0 | 81.3 ± 8.0 |
| Heparin | 0.90 ± 0.03 | 45.0 ± 1.5 | 0.90 ± 0.03 | 1.50 ± 0.05 |

Example 4: Chromogenic Assay for the Measurement of Antithrombin Activity

Factor Xa Activity

The BIOPHEN Heparin Anti-Xa (2 stages) USP/EP kit (Aniara) was used to determine factor Xa activity. This chromogenic anti-Xa method for measuring homogeneous heparin in purified systems is in compliance with Pharmacopoeias (USP, EP) and FDA guidelines. All reagents were prepared according to manufacturer's instructions and incubated at 37° C. for 15 min. Varying concentrations of heparin (Neoparin) or glycopolymers 1-4 (40 μL) and antithrombin (40 μL) were added to a microcentrifuge tube, mixed, and incubated at 37° C. for 2 min. Factor Xa (40 μL) was added to the solution, incubated at 37° C. for exactly 2 min, and then the factor Xa chromogenic substrate (40 μL) was added. After 2 min, the reaction was quenched with citric acid (20 g/L, 240 μL), and the absorbance was measured at 405 nm. The sample blank was obtained by mixing the reagents in reverse order, and the resulting value was deducted from the absorbance values measured in the assay.

Thrombin (Factor IIa) Activity

The BIOPHEN Heparin Anti-IIa (2 stages) USP/EP kit (Aniara) was used to determine factor IIa activity. This chromogenic anti-IIa method was conducted according to the same procedure used for factor Xa.

Figure 4A:
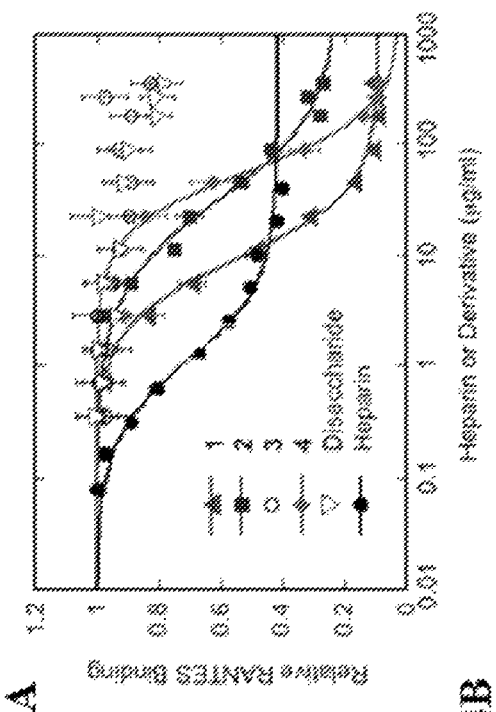
FIGS. 4A and 4B show the RANTES binding abilities and relative FXa activity of disaccharide, heparin and glycopolymers.
Figure 4B:
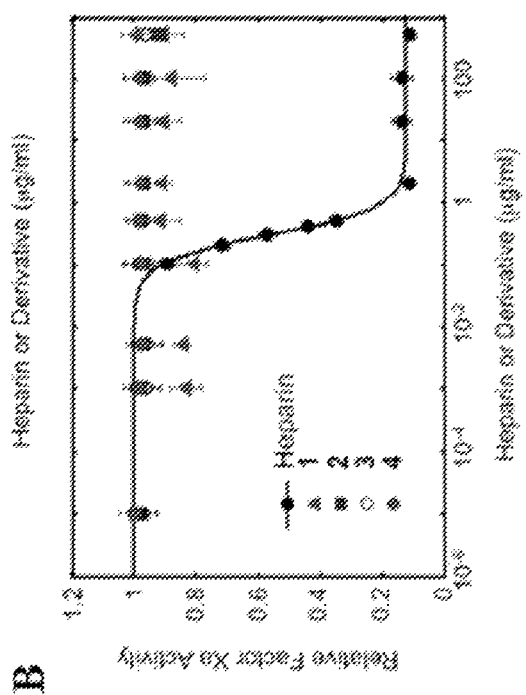

The relative ability of each glycopolymer to block RANTES binding to heparin (EC50=12.2 nM) was tested by a competitive enzyme-linked immunosorbent assay. As shown in FIGS. 4A and 4B and Table 3, trisulfated glycopolymer 1 bound strongly to RANTES (IC50=9.3±1.1 μg/mL (334±39 nM)), albeit with reduced affinity compared to heparin of similar chain length (IC50=0.90±0.03 μg/mL (45.0±1.5 nM). However, the glycopolymer competed more effectively for RANTES binding compared to heparin at its maximum inhibitory concentration. Whereas heparin exhibited a maximum inhibition of 58.4%, glycopolymer 1 inhibited RANTES binding by up to 90.8% under the same assay conditions.

The effects of site-defined modifications to the sulfation pattern of glycopolymer 1 on its affinity for RANTES was tested. Removal of either the N-sulfate group of GlcN (glycopolymer 2) or the 2-O-sulfate group of IdoA (glycopolymer 4) decreased binding to RANTES (IC50=31.1±6.2 μg/mL (852±170 nM) and 58.0±5.7 μg/mL (1760±170 nM), respectively), and unsulfated glycopolymer 3 had no appreciable activity (FIG. 4A). The observation suggests that both of the sulfation pattern and sulfation degree are important for determining the affinity of the glycopolymers for RANTES. Importantly, none of the glycopolymers possessed anti-coagulant activity, as demonstrated by their inability to potentiate the inhibition of factor Xa and thrombin substrates by antithrombin III (FIG. 4B). Thus, controlling the positioning of sulfate groups within the glycopolymer enables the anti-inflammatory function of HS/heparin to be dissected from its anti-coagulant function. Furthermore, modifications to the sulfation pattern can be exploited to adjust the affinity of the glycopolymers for different HS-binding proteins and may facilitate the development of glycosaminoglycan-based therapeutic agents with fewer off-target side effects.

Example 5: Cell Migration Assay

L1.2 cells (mouse pre-B lymphocytes) stably transfected with CCR3, CCR5, or vector only, were kindly provided by Dr. Osamu Yoshie (Kinki University, School of Medicine, Japan). Cells were maintained in RPMI 1640 (Invitrogen) supplemented with 10% FBS, 100 μg/mL penicillin/streptomycin (Invitrogen), and 50 μM 2-mercaptoethanol (Sigma Aldrich). Cells were routinely analyzed by flow cytometry (FACSCalibur, Beckman Dickenson) to verify that cultures expressed adequate levels of chemokine receptor (>90%) for migration and cell binding assays.

Experiments were performed using ChemoTx chambers (Neuroprobe). L1.2 cells (wild-type or stably-transfected with CCR3 or CCR5) were harvested and washed twice in flow cytometry buffer (Hank's Balanced Salt Solution (HBSS) with 2.5 mg/mL bovine serum albumin (BSA) and 10 mM HEPES). Human RANTES (R&D Systems) was serially diluted in flow cytometry buffer (0.5-1024 nM), and 30 μL of each dilution was added to the bottom wells of the ChemoTx chamber. Alternatively, in competitive migration assays, 1 or 10 nM of RANTES was pre-incubated with various concentrations of heparin or glycopolymer 1 (0.020-4.0 μg/mL) for 30 min at rt, and the same volume of each solution was added to the bottom wells. The sample plate was fitted with a 5-μm pore filter, and 106 cells (50 μL) were placed on top of each well. Cells were allowed to migrate through the filter for 4 h at 37° C. and 5% CO2. Subsequently, non-migrating cells were removed from the top of the filter by manual scraping; cells adhering to the filter were dislodged using 20 μL of 2.5 mM EDTA for 30 min at rt. Migrated cells were transferred (500×g, 5 min) to a 96-well black-walled clear-bottomed plate (Corning) using a funnel plate (Neuroprobe). Cells were lysed at −80° C. and stained with CyQUANT dye (Invitrogen) as described in the product literature. Fluorescence was measured at 535 nm using a Victor 3 plate reader (PerkinElmer).

Example 6: Chemokine Cell Binding Assay $3 \times 10^6$ L1.2 cells (wild-type or stably-transfected with CCR3) were washed twice with flow cytometry buffer and incubated with RANTES (100 nM in flow cytometry buffer) for 45 min at rt. Alternatively, cells were incubated with RANTES (100 nM in flow cytometry buffer) previously treated with various concentrations of heparin or glycopolymer 1 (0.02-2 μg/mL) for 30 min at rt. Cells were spun twice (500×g, 5 min) through 100% FBS (1.0 mL) to remove excess reagent and stained with phycoerythrin (PE)-conjugated anti-RANTES (1 test) in FACS buffer (100 μL) for 1 h at 4° C. Cells were again spun twice through 100% FBS (1.0 mL) and resuspended in flow cytometry buffer (500 μL)

for flow cytometry analysis. Immediately before analysis, 7-amino-actinomycin-D (7-AAD, 5 μL, eBioscience) was added to evaluate cell viability. Cells were analyzed for PE intensity on a FACSCalibur flow cytometer (Beckman Dickenson, Caltech Flow Cytometry Facility) with 10,000 cell events per sample. Data analysis was performed using FlowJo (Tree Star Inc.).

Figure 5A:
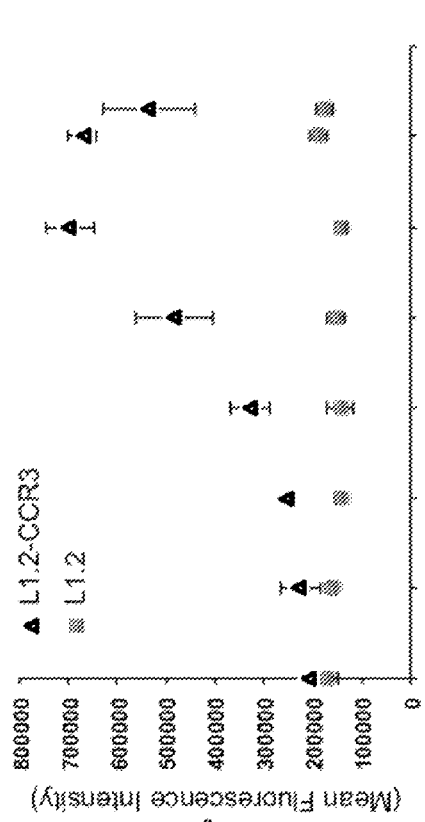
FIGS. 5A and 5B show the RANTES-induced migration of CCR3- and CCR5-expressing cells.
Figure 5B:
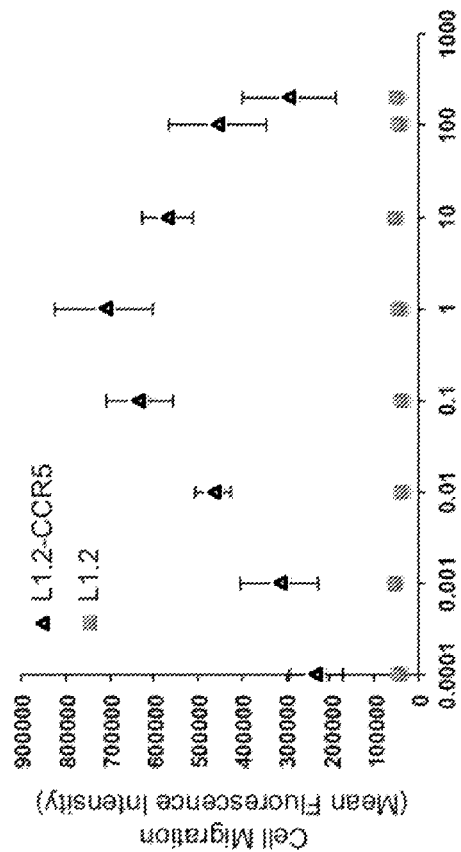
Figure 6:
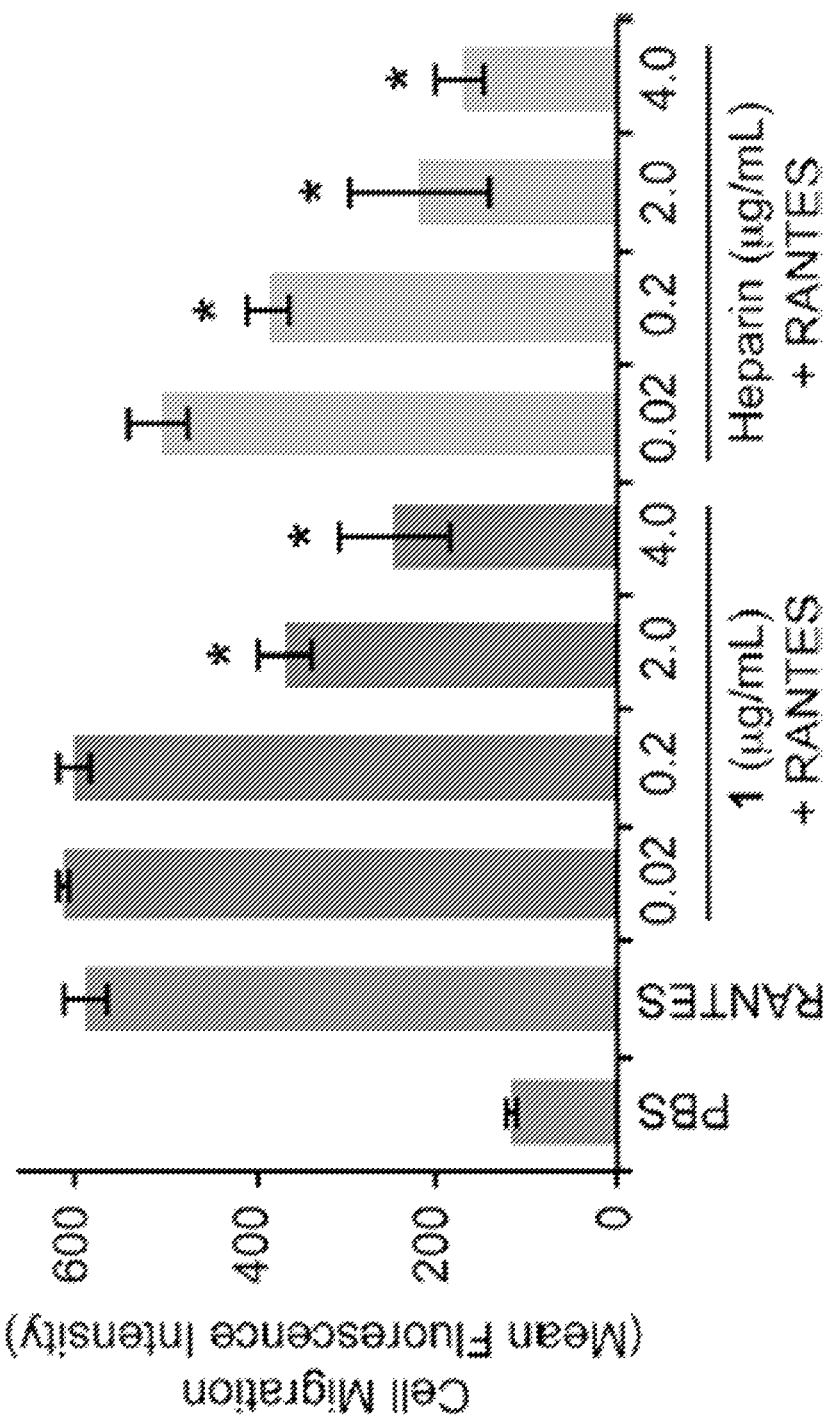
FIG. 6 shows the RANTES-induced migration of CCR3-expressing cells.
Figure 7:
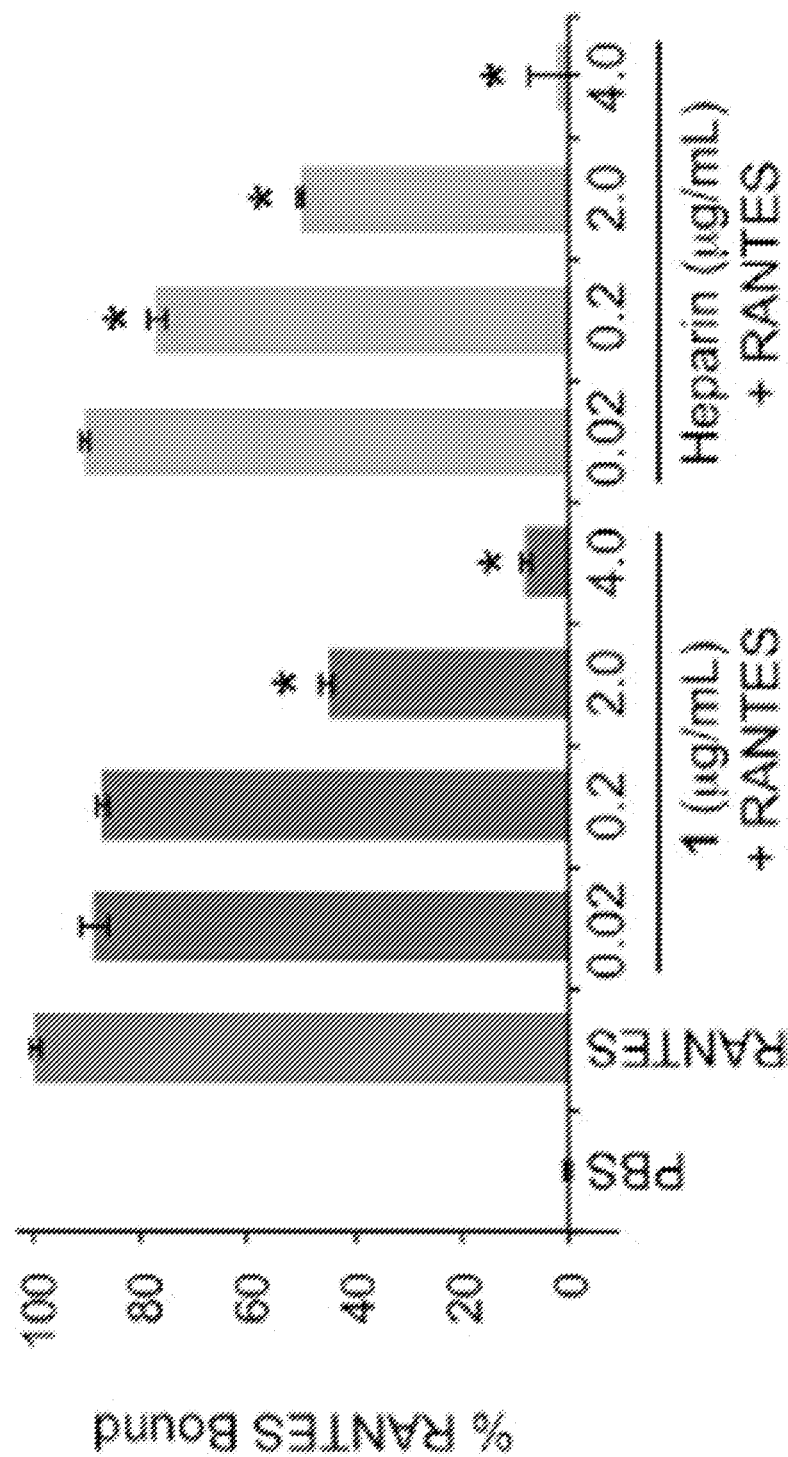
FIG. 7 shows the RANTES binding to CCR3-expressing cells.
Figure 8:
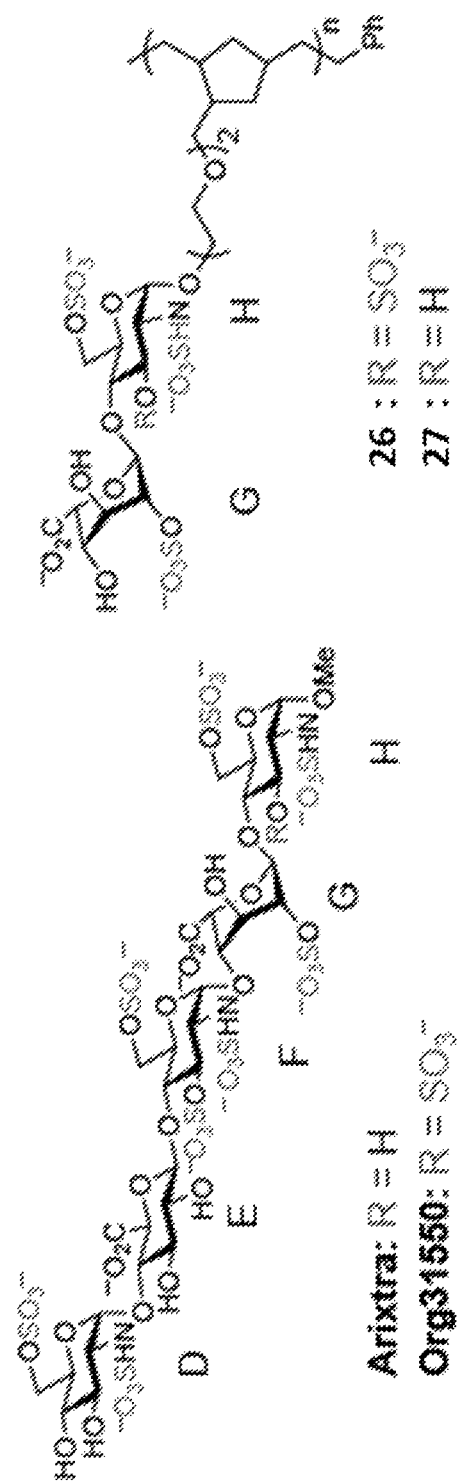
FIG. 8 depicts the chemical structure of Arixtra, Org31550, and synthetic glycopolymers 26 and 27.
Figure 9:
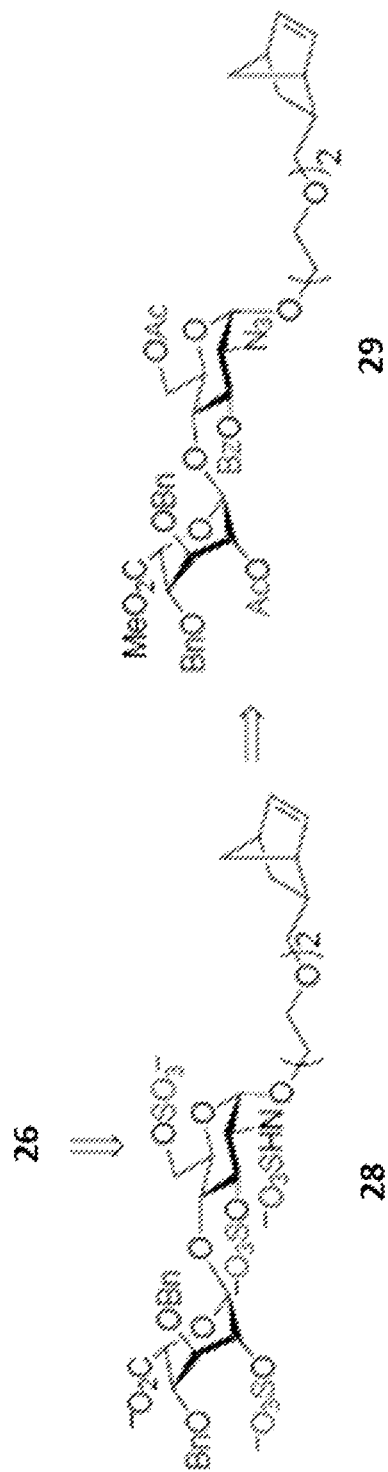
FIG. 9 shows an exemplary method for retrosynthesizing glycopolymer 26 from a disaccharide.

The chemotactic activity of RANTES, which is essential to the pathogenesis of allergic inflammatory responses such as asthma, is mediated in part by the G-protein coupled receptor CCR3. To test whether glycopolymer 1 can interfere with RANTES-induced chemotaxis via CCR3, we probed the migration of murine L1.2 pre-B cells that were stably transfected with the CCR3 receptor. Using a modified Boyden chamber, we observed that the directional migration of L1.2-CCR3 cells (but not wild-type L1.2 cells lacking CCR3) was dependent on the RANTES concentration and elicited a maximal response at 10 nM (FIGS. 5A and 5B). Pre-incubation of RANTES (10 nM) with either glycopolymer 1 or heparin diminished the chemotactic activity of RANTES in a dose-dependent manner (FIG. 6). Further corroborating these results, lower levels of RANTES were detected on the surface of CCR3-expressing cells after the chemokine (100 nM) was pretreated with glycopolymer 1 or heparin, as determined by flow cytometry analysis (FIG. 7).

Example 7: Synthesis and Characterization of Compound 31 and Intermediates Thereof Compounds to be used in the further preparing procedures may be synthesized by a method shown in FIGS. 10A and 10B.

tert-Butyldimethylsilyl 6-O-acetyl-2-azido-3-O-benzyl-4-tert-butyldimethylsilyl-2-deoxy-β-D-glucopyranoside (S2)

Compound S2 was prepared from 6-O-acetyl-2-azido-3-β-benzyl-4-tert-butyldimethylsilyl-2-deoxy-β-D-glucopyranoside (S1) using a number of procedures. (See e.g., Orgueira H. A. et al., Chem. Eur. J. 2003, 9, 140-169.) The analytical data were in agreement with the reported spectra.

tert-Butyldimethylsilyl 6-O-acetyl-2-azido-3-O-benzoyl-4-tert-butyldimethylsilyl-2-deoxy-β-D-glucopyranoside (S3)

Oxidation conditions were adapted from previously published procedures.[2] Compound S2 (200 mg, 0.353 mmol) was added to a mixture of 1.00 mL of carbon tetrachloride, 1.00 mL of acetonitrile, and 1.50 mL of $H_2O$. To this, sodium metaperiodate (755 mg, 10 eq) and ruthenium dioxide (47.0 mg, 1 eq) were added sequentially, and the reaction was stirred for 18 h at rt in the dark. The resulting slurry as diluted with $CH_2Cl_2$, and the aqueous layer was extracted with $CH_2Cl_2$ (3×). The organic layers were combined, filtered through a pad of Celite, and concentrated in vacuo. The residue was purified by silica gel flash chromatography (20:1 hexanes:EtOAc) to deliver 164 mg (80%) of S3 as a colorless oil. $^1$H NMR (300 MHz; CDCl$_3$): δ 8.07 (d, J=7.2 Hz, 2H), 7.59 (t, J=7.5 Hz, 1H), 7.47 (t, J=7.5 Hz, 2H), 5.16 (dd, J=10.2, 9.0 Hz, 1H), 4.72 (d, J=7.5 Hz, 1H), 4.43 (dd, J=11.7, 1.8 Hz, 1H), 4.12 (dd, J=12.0, 6.3 Hz, 1H), 3.85 (t, J=9.0 Hz, 1H), 3.61-3.56 (m, 1H), 3.44 (dd, J=10.5, 7.8 Hz, 1H), 2.10 (s, 3H), 0.93 (s, 9H), 0.75 (s, 9H), 0.16 (s, 6H), 0.02 (s, 3H), −0.20 (s, 3H); $^{13}$C NMR (75 MHz; CDCl$_3$: δ 170.6, 165.4, 133.3, 129.9, 128.5, 97.1, 74.9, 74.4, 69.6, 66.8, 63.0, 25.5, 22.2, 20.8, 17.9, 17.8, −4.1, −4.5, −4.9, −5.3; HRMS (ESI-TOF) m/z calcd for $C_{27}H_{44}N_3O_7Si_2$ [M−H]$^-$ 578.2718. obsd 578.2718.

6-O-Acetyl-2-azido-3-O-benzoyl-4-tert-butyldimethylsilyl-2-deoxy-β-D-glucopyranoside trichloroacetimidate (S4)

To a solution of S3 (5.01 g, 8.63 mmol) in 60.0 mL THF at 0° C. was added glacial AcOH (0.670 mL) and TBAF (1 M in THF, 10.4 mL). The reaction mixture was stirred at 0° C. for 2 h, then diluted with 200 mL $Et_2O$, and washed with brine (3×). The organic layer was dried over MgSO$_4$, filtered through Celite, and concentrated in vacuo. The crude residue was dissolved in $CH_2Cl_2$ (215 mL) and cooled to 0° C. Trichloroacetonitrile (13.0 mL, 130 mmol) and DBU (130 μL, 0.871 mmol) were added, and the solution was stirred for 2 h at 0° C. The reaction mixture was concentrated in vacuo and purified by silica gel flash chromatography (10:1 hexanes:EtOAc) to afford a 10:1 mixture of α:β anomers (3.80 g, 92%) as a light yellow foam. $^1$H NMR (500 MHz; CDCl$_3$): δ 8.34 (s, 1H), 8.08 (d, J=7.0 Hz, 2H), 7.61 (t, J=7.5 Hz, 1H), 7.48 (t, J=7.5 Hz, 2H), 6.52 (d, J=3.6 Hz, 1H), 5.73 (dd, J=10.5, 8.4 Hz, 1H), 4.42 (d, J=10.5 Hz, 1H), 4.18-4.10 (m, 2H), 4.05 (t, J=9.0 Hz, 1H), 3.64 (dd, J=10.5, 3.5 Hz, 1H), 2.09 (s, 3H), 0.77 (s, 9H), 0.03 (s, 3H), −0.14 (s, 3H); $^{13}$C NMR (126 MHz; CDCl$_3$): δ 170.58, 165.50, 160.96, 133.61, 130.04, 129.67, 128.65, 94.91, 90.78, 73.20, 72.85, 69.26, 62.51, 61.63, 29.83, 25.71, 25.71, 25.69, 25.67, 20.92, 18.04, −3.90, −4.79; HRMS (ESI-TOF): m/z calcd for $C_{23}H_{31}Cl_3N_4O_7SiNa$ [M+Na]$^+$ 631.0925. obsd 631.0925.

2-(2-((2S)-Bicyclo[2.2.1]hept-5-en-2-ylmethoxy)ethoxy)ethanol (S5)

Exo-5-norbornene-2-methanol (4.09 g, 33.0 mmol) was dissolved in THF (60.0 mL) with 4 Å molecular sieves (MS) and stirred at room temperature (rt) for 30 min. The solution was cooled to 0° C., and 95% NaH in mineral oil (1.06 g, 41.2 mmol) was added in portions at 0° C. over 30 min. A solution of 2-[2-[[(1,1-dimethylethyl)dimethylsilyl]oxy]ethoxy]ethyl-1-methanesulfonate (8.20 g, 27.5 mmol) and 18-crown-6 (1.45 g, 5.49 mmol) in THF (15.0 mL) was added dropwise to this solution, stirred for 2 h at rt, and quenched with $H_2O$ until there was no gas formation. The resulting solution was diluted with $CH_2Cl_2$, washed with saturated NaHCO$_3$, dried over MgSO$_4$, and concentrated in vacuo. Purification by silica gel flash chromatography (20:1→5:1 hexanes:EtOAc) afforded the desired tert-butyldimethylsilyl-protected intermediate (7.21 g) in 67% yield. $^1$H NMR (500 MHz; CDCl$_3$): δ 6.00 (d, J=25 Hz, 2H), 3.71 (t, J=5.5 Hz, 2H), 3.60-3.28 (m, 8H), 2.72 (s, 1H), 2.69 (s, 1H), 1.65-1.62 (m, 1H), 1.26-1.21 (m, 2H), 1.19-1.14 (m, 1H), 1.05-1.01 (m, 1H), 0.83 (s, 9H), 0.00 (s, 6H); $^{13}$C NMR (125 MHz; CDCl$_3$): δ 147.1, 86.4, 83.0, 81.1, 80.7, 73.1, 55.3, 54.0, 51.9, 49.1, 40.0, 36.3, 28.7, 5.1; HRMS (ESI-TOF): m/z calcd for C18H35O3Si [M+H]+ 327.2356, obsd 327.2356. The intermediate from the previous step (7.21 g, 22.1 mmol) was dissolved in THF (100 mL) and cooled to 0° C. A solution of 1 M TBAF in THF (44.2 mL, 44.2 mmol) was added to the reaction mixture dropwise, and the reaction was stirred for 2 h at 0° C. The reaction was quenched with $H_2O$ and extracted with EtOAc (3×15.0 mL). The organic layers were combined, dried over MgSO$_4$, and concentrated in vacuo. Purification by silica gel flash chromatography (5:1→1:1 hexanes:EtOAc) afforded the desired product (4.55 g) in 97% yield. $^1$H NMR (500 MHz; CDCl$_3$): δ

6.11-6.04 (m, 2H), 3.72-3.37 (m, 10H), 2.80 (s, 1H), 2.74 (s, 1H), 2.48 (m, 1H), 1.71 (m, 1H), 1.34-1.23 (m, 3H), 1.13-1.09 (m, 1H); $^{13}$C NMR (125 MHz; CDCl$_3$): δ 136.9, 136.8, 76.4, 72.2, 70.7, 70.6, 62.1, 45.2, 43.9, 41.8, 39, 30; HRMS (ESI-TOF): m/z calcd for C$_{12}$H$_{21}$O$_3$ [M+H]$^+$ 213.1491. obsd 213.1483.

6-O-Acetyl-2-azido-3-O-benzoyl-4-O-tert-butyldimethylsilyl-1-O-(2-(2-((2S)-bicyclo[2.2.1]hept-5-en-2-ylmethoxy)ethoxy)ethyl)-2-deoxy-β-D-glucopyranoside (S6)

Compounds S4 (444 mg, 0.728 mmol) and S5 (230 mg, 1.08 mmol) were azeotroped (3×) with toluene (5.00 mL) and dried for 1 h under high vacuum. The starting materials were dissolved in CH$_2$Cl$_2$ (5.00 mL) and mixed with activated 4 Å MS for 20 min at rt. The solution was then cooled to −20° C., and BF$_3$.OEt$_2$ (0.720 mL of 0.5 M solution in CH$_2$Cl$_2$, 0.36 mmol) was added dropwise. After stirring at −20° C. for 30 min, the reaction mixture was warmed to 0° C., quenched with Et$_3$N, and filtered through a pad of Celite. After removal of organic solvents in vacuo, the residue was purified by silica gel flash chromatography (3:1 hexanes:EtOAc) to afford 30 (370 mg) in 84% yield as a white solid. $^1$H NMR (500 MHz; CDCl$_3$): δ 8.04 (dt, J=7.1, 1.4 Hz, 2H), 7.56 (t, 1H), 7.44 (t, 2H), 6.04 (ddd, J=26.4, 5.7, 2.9 Hz, 2H), 5.15 (dd, J=10.4, 8.9 Hz, 1H), 4.58 (dd, J=8.1, 1.2 Hz, 1H), 4.43 (dd, J=12.0, 2.2 Hz, 1H), 4.12-4.10 (m, 1H), 4.00 (dt, J=11.2, 4.4 Hz, 1H), 3.92-3.76 (m, 2H), 3.75-3.65 (m, 2H), 3.65-3.44 (m, 7H), 3.34 (td, J=9.3, 4.3 Hz, 1H), 2.79-2.69 (m, 2H), 2.01 (s, 3H), 1.29-1.26 (m, 1H), 1.07 (dt, J=11.6, 3.9 Hz, 1H), 0.72 (s, 7H), −0.02 (s, 3H), −0.22 (s, 3H); $^{13}$C NMR (126 MHz; CDCl$_3$): δ 170.76, 165.51, 136.68, 136.61, 133.41, 129.93, 128.53, 102.22, 77.41, 77.16, 76.90, 76.11, 75.21, 74.37, 70.71, 70.45, 70.30, 69.36, 69.29, 64.51, 62.81, 60.46, 45.05, 43.68, 41.57, 38.77, 29.77, 25.61, 21.09, 20.96, 17.87, 14.24, −4.02, −4.88; HRMS (ESI-TOF): m/z calcd for C$_{33}$H$_{50}$N$_3$O$_9$Si [M+H]$^+$ 660.3311. obsd 660.3297.

6-O-Acetyl-2-azido-3-O-benzoyl-1-O-(2-(2-((2S)-bicyclo[2.2.1]hept-5-en-2-ylmethoxy)ethoxy)ethyl)-2-deoxy-β-D-glucopyranoside (30)

To a solution of S4 (370 mg, 0.607 mmol) in THF (6.00 mL) and pyridine (6.00 mL) at 0° C. was added HF.pyridine (3.50 mL) dropwise. The reaction mixture was allowed to warm up to rt and stirred overnight. The reaction was quenched with a saturated NaHCO$_3$ solution and diluted with EtOAc. The reaction mixture was extracted with EtOAc and then washed with saturated NaHCO$_3$, brine, and 10% CuSO$_4$, dried over MgSO$_4$, and concentrated in vacuo. The resulting residue was purified by silica gel flash chromatography (1:1:2 CH$_2$Cl$_2$:hexanes:EtOAc) to furnish compound 30 (250 mg) in 83% yield as a white solid. $^1$H NMR (500 MHz; CDCl$_3$): δ 8.06 (dt, J=6.8, 1.4 Hz, 2H), 7.64-7.54 (m, 1H), 7.49-7.42 (m, 2H), 6.06 (ddd, J=24.1, 5.6, 2.9 Hz, 2H), 5.06 (dd, J=10.3, 9.1 Hz, 1H), 4.57 (d, J=8.0 Hz, 1H), 4.44-4.33 (m, 2H), 4.08-4.00 (m, 1H), 3.84 (ddd, J=10.9, 6.1, 4.2 Hz, 1H), 3.75-3.71 (m, 2H), 3.68-3.65 (m, 2H), 3.62-3.55 (m, 3H), 3.51 (ddd, J=9.5, 6.2, 3.2 Hz, 1H), 3.36 (td, J=9.2, 4.8 Hz, 1H), 2.81-2.69 (m, 2H), 2.09 (s, 3H), 1.69 (tt, J=9.4, 5.6 Hz, 1H), 1.34-1.26 (m, 2H), 1.08 (dt, J=11.7, 4.3, 3.3 Hz, 1H); $^{13}$C NMR (125 MHz; CDCl$_3$): δ 171.61, 167.00, 149.51, 136.76, 136.64, 133.76, 130.09, 129.17, 128.62, 102.36, 76.16, 76.06, 74.17, 70.77, 70.46, 70.33, 69.53, 69.29, 63.90, 63.11, 45.09, 43.73, 41.62, 38.82, 29.82, 20.98; HRMS (ESI-TOF): m/z calcd for C$_{27}$H$_{36}$N$_3$O$_9$ [M+H]$^+$ 546.2446. obsd 546.2453

Methyl 3,4-di-O-benzyl-1,2-methylorthoaceto-α-L-idopyranosiduronate (S8)

Methyl 3-O-benzyl-β-L-idopyranuronate 1,2-(methyl-orthoacetate) (S7, 1.60 g, 4.52 mmol) was dissolved in neat benzyl bromide (20.0 mL, 5.00 mL/mmol, filtered through a pad of activated basic alumina immediately before use) along with activated 4 Å MS (500 mg/mmol). To this was added TBAI (1.34 g, 3.62 mmol), and the resulting mixture was stirred at rt for 15 min. Freshly prepared Ag$_2$O (4.19 g, 18.1 mmol) was added to the mixture and stirred at rt for 8 h the absence of light. The reaction mixture was diluted with Et$_2$O, filtered through Celite, and concentrated in vacuo. Purification by silica gel flash chromatography (6:1→2:1, hexanes:EtOAc+0.5% Et$_3$N) afforded the desired product (1.51 g) in 75% yield. $^1$H NMR (500 MHz; CDCl$_3$): δ 7.38-7.19 (m, 10H), 5.50 (d, J=2.9 Hz, 1H), 4.58-4.52 (m, 3H), 4.44-4.37 (m, 2H), 4.13-4.08 (m, 1H), 4.08-4.04 (m, 1H), 3.85-3.80 (m, 1H), 3.71 (s, 3H), 3.25 (s, 3H), 1.67 (s, 3H); $^{13}$C NMR (125 MHz; CDCl$_3$): δ 169.31, 137.72, 137.07, 128.74, 128.39, 128.36, 127.99, 127.83, 127.81, 124.50, 96.85, 77.41, 77.16, 76.91, 76.31, 72.82, 72.77, 72.00, 71.40, 71.19, 52.43, 49.25, 25.08; HRMS (ESI-TOF): m/z calcd for C$_{24}$H$_{28}$O$_8$ [M+Na]$^+$ 467.1687. obsd 467.1675.

Methyl dibutylphosphate-2-O-acetyl-3,4-di-O-benzyl-α-L-idopyranosiduronate (31)

Compound S8 (688 mg, 1.55 mmol) was azeotroped with toluene (3×10.0 mL) and dried for 1 h under vacuum. Activated 4 Å MS (500 mg/mmol) under flux of argon were added, and the starting material was dissolved in CH$_2$Cl$_2$ (1.00 mL/0.100 mmol). After stirring for 10 min at rt, the mixture was added dropwise via cannula (within 30 min) to a 3 M solution of HOPO(OBu)$_2$ in CH$_2$Cl$_2$ (977 µL, 4.65 mmol) in the presence of 4 Å MS (500 mg/mmol HOPO (OBu)$_2$). After 5 h at rt, the reaction was cooled to 0° C. and Et$_3$N (865 µL, 6.20 mmol) was added. The solution was warmed to rt and filtered through a pad of deactivated silica gel. The resulting mixture was concentrated in vacuo, and purified by silica gel flash chromatography (4:1→2:1 hexanes:EtOAc+0.5% Et$_3$N) to afford the desired product (888 mg) in 92% yield. $^1$H NMR (500 MHz; CDCl$_3$): δ 7.45-7.16 (m, 10H), 5.86 (d, J=6.9, 1.3 Hz, 1H), 5.03 (dt, J=2.8, 1.2 Hz, 1H), 4.95 (d, J=2.5 Hz, 1H), 4.83-4.57 (dd, 2H), 4.55-4.40 (dd, 2H), 4.15-3.98 (m, 4H), 3.95-3.82 (m, 2H), 3.74 (s, 3H), 2.04 (s, 3H), 1.69-1.59 (m, 4H), 1.46-1.32 (m, 4H), 0.99-0.87 (m, 6H); $^{13}$C NMR (126 MHz; CDCl$_3$): δ 169.65, 168.74, 137.21, 137.05, 128.30, 128.22, 127.86, 127.82, 127.80, 127.66, 95.33, 95.29, 77.42, 77.16, 76.90, 73.49, 72.32, 72.08, 70.62, 68.89, 67.82, 67.77, 67.75, 67.71, 66.83, 66.76, 52.04, 32.06, 32.00, 31.95, 20.71, 18.44, 13.42, 13.41; HRMS (ESI-TOF): m/z calcd for C$_{31}$H$_{44}$O$_{11}$P [M+H]$^+$ 623.2616. obsd 623.2624.

Example 8: Synthesis of Glycopolymers 26

Figure 11:
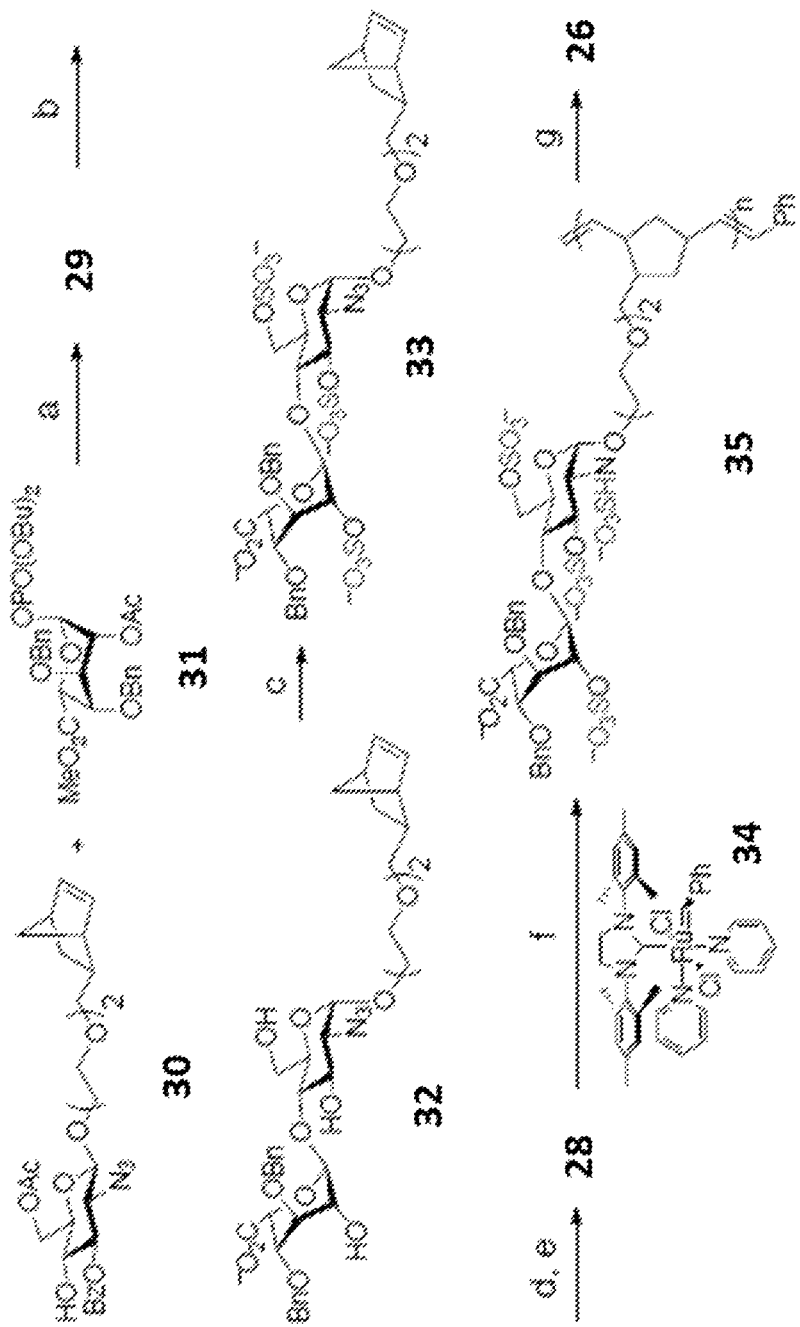
FIG. 11 provides an exemplary synthetic route for glycopolymer 26.

An exemplary synthetic route for glycopolymers is shown in FIG. 11.

Methyl 2-O-acetyl-3,4-di-O-benzyl-α-L-idopyranosiduronate-(1→4)-6-O-acetyl-2-azido-3-O-benzoyl-1-O-(2-(2-((2S)bicyclo[2.2.1]hept-5-en-2-ylmethoxy)ethoxy)ethyl)-2-deoxy-β-D-glucopyranoside (29)

Donor 31 (51.6 mg, 0.0829 mmol) and acceptor 30 (29.7 mg, 0.0592 mmol) were azeotroped with toluene (3×5.00 mL) and dried for 2 h under high vacuum. The mixture was dissolved in $CH_2Cl_2$ (2 mL/0.100 mmol of 5), cooled to −30° C. for 2 min, and TMSOTf (22.0 μL, 0.0960 mmol) was added dropwise. After stirring at −30° C. for 1 h, the reaction mixture was quenched with $Et_3N$ (2 eq) and filtered through a pad of Celite. After removal of organic solvents in vacuo, the residue was purified by silica gel flash chromatography (3:1 hexanes:EtOAc) to afford compound 29 (47.5 mg) in 85% as a colorless oil. $^1$H NMR (500 MHz; $CDCl_3$): δ 8.07-8.02 (m, 2H), 7.59-7.52 (m, 1H), 7.42 (dd, J=8.3, 7.2 Hz, 2H), 7.36-7.19 (m, 8H), 7.12-7.07 (m, 2H), 6.07 (ddd, J=25.9, 5.7, 3.0 Hz, 2H), 5.25 (dd, J=10.3, 9.2 Hz, 1H), 5.09 (d, J=4.7 Hz, 1H), 4.77-4.72 (m, 1H), 4.63 (d, J=12.1 Hz, 1H), 4.57-4.52 (m, 2H), 4.41 (dd, J=12.2, 2.0 Hz, 1H), 4.32 (dd, 2H), 4.22-4.15 (m, 2H), 4.08-3.98 (m, 2H), 3.88-3.77 (m, 1H), 3.72 (dd, J=5.7, 3.6 Hz, 2H), 3.68-3.50 (m, 6H), 3.41 (s, 3H), 3.39-3.32 (m, 1H), 2.82-2.72 (m, 2H), 2.04 (s, 3H), 1.96 (s, 3H), 1.78-1.61 (m, 1H), 1.33-1.19 (m, 2H), 1.13-1.06 (m, 1H); $^{13}$C NMR (125 MHz; $CDCl_3$): δ 170.73, 170.01, 169.66, 165.46, 137.91, 137.31, 136.75, 136.72, 133.09, 130.12, 129.90, 128.50, 128.43, 128.32, 128.04, 127.91, 127.81, 127.65, 102.39, 99.00, 77.41, 77.16, 76.91, 76.20, 76.09, 75.09, 74.16, 73.03, 73.01, 72.77, 72.60, 70.87, 70.74, 70.55, 70.43, 70.41, 70.25, 69.55, 64.45, 62.28, 60.52, 51.79, 45.12, 43.75, 41.66, 38.86, 29.84, 21.19, 20.97, 20.90, 14.33; HRMS (ESI-TOF): m/z calcd for $C_{50}H_{59}N_3O_{16}Na$ [M+Na]$^+$ 980.3788. obsd 980.3783.

3,4-Di-O-benzyl-α-L-idopyranosiduronate-(1→4)-2-azido-1-O-(2-(2-((2S)bicyclo[2.2.1]hept-5-en-2-ylmethoxy)ethoxy)ethyl)-2-deoxy-β-D-glucopyranoside (32)

To a solution of 29 (60.0 mg, 0.0636 mmol) in THF (5.00 mL) at −10° C. were added LiOH (1 M solution, 0.636 mL) and $H_2O_2$ (30% solution, 0.365 mL) simultaneously. After stirring for 12 h at rt, the mixture was cooled to −10° C., and MeOH (5.00 mL) and NaOH (4 M solution, 0.790 mL) were added. This reaction mixture was stirred at rt for 12 h, neutralized with Amberlite® IR120 Hydrogen form resin, filtered, and concentrated in vacuo. The residue was first purified by Sephadex® LH-20 chromatography (1:1 $CH_2Cl_2$:MeOH), followed by silica gel flash chromatography (40:2:1 EtOAc:MeOH:$H_2O$) to furnish compound 32 (40.2 mg) in 82% as a colorless oil. $^1$H NMR (500 MHz; $CD_3OD$): δ 7.39-7.20 (m, 10H), 6.06 (ddd, J=20.5, 5.7, 3.0 Hz, 2H), 4.99 (d, J=3.6 Hz, 1H), 4.69 (d, J=11.3 Hz, 1H), 3.71-3.67 (m, 3H), 4.65 (d, J=2.6 Hz, 1H), 4.62-4.54 (m, 3H), 4.40 (d, J=8.1 Hz, 1H), 4.09 (ddd, J=3.6, 2.7, 0.8 Hz, 1H), 3.99 (dt, J=11.2, 4.3 Hz, 1H), 3.83 (d, J=12.1, 2.3 Hz, 1H), 3.81-3.69 (m, 2H), 3.68-3.56 (m, 6H), 3.52 (dd, J=9.5, 6.3 Hz, 1H), 3.46-3.36 (m, 2H), 3.17 (dd, J=9.8, 8.2 Hz, 1H), 2.74 (d, J=27.8 Hz, 2H), 1.65 (dddd, J=14.7, 8.4, 4.4, 1.4 Hz, 1H), 1.36-1.26 (m, 3H), 1.21 (dddd, J=11.5, 8.4, 2.4, 0.8 Hz, 1H), 1.16-1.09 (m, 1H); $^{13}$C NMR (126 MHz; $CD_3OD$): δ 176.22, 139.73, 139.44, 137.69, 137.55, 129.45, 129.29, 128.85, 128.77, 128.60, 103.76, 103.04, 79.61, 78.74, 78.61, 77.02, 76.78, 75.10, 74.39, 73.31, 72.06, 71.62, 71.56, 71.40, 70.79, 69.99, 68.38, 61.87, 45.85, 44.89, 42.76, 40.08, 30.63; HRMS (ESI-TOF): m/z calcd for $C_{38}H_{49}N_3O_{13}Na$ [M+Na]$^+$ 778.3158. obsd 778.3160.

3,4-Di-O-benzyl-2-O-sulfonato-α-L-idopyranosiduronate-(1→4)-2-azido-3,6-di-O-sulfonato-1-O-(2-(2-((2S)bicyclo[2.2.1]hept-5-en-2-ylmethoxy)ethoxy)ethyl)-2-deoxy-β-D-glucopyranoside (33)

To a solution of 32 (42.8 mg, 0.0567 mmol) in anhydrous DMF (3.50 mL) at rt was added $SO_3.NMe_3$ (237 mg, 1.70 mmol). The reaction mixture was stirred at 55° C. for 2 d and then quenched with $Et_3N$ (1.00 mL) and MeOH (3.00 mL). After concentration in vacuo, the residue was purified by Sephadex® LH-20 (1:1 $CH_2Cl_2$:MeOH) to obtain compound 33 (39.7 mg) in 71% yield as a white solid. $^1$H NMR (500 MHz; $CD_3OD$): δ 7.53-7.45 (m, 2H), 7.42-7.20 (m, 8H), 6.08 (ddd, J=23.8, 5.7, 3.0 Hz, 2H), 4.67 (d, J=12.1 Hz, 2H), 4.48 (t, J=9.4 Hz, 2H), 4.36 (t, J=9.0 Hz, 1H), 4.31-4.18 (m, 4H), 4.00 (dt, J=11.3, 4.4 Hz, 1H), 3.92 (s, 1H), 3.81 (dt, J=10.7, 4.9 Hz, 2H), 3.75-3.57 (m, 9H), 3.53 (dt, J=9.5, 6.3 Hz, 1H), 3.41 (td, J=9.2, 5.8 Hz, 2H), 2.75 (d, J=30.2 Hz, 2H), 1.67 (dddd, J=9.4, 7.5, 5.3, 3.7 Hz, 1H), 1.40-1.32 (m, 3H), 1.23 (ddd, J=11.0, 8.3, 2.3 Hz, 1H), 1.14 (dt, J=11.7, 3.9 Hz, 1H); $^{13}$C NMR (126 MHz; $CD_3OD$): δ 179.50, 157.52, 153.60, 144.04, 137.60, 129.40, 128.68, 127.75, 112.94, 110.71, 106.19, 101.94, 79.98, 77.03, 71.56, 70.36, 67.22, 63.39, 56.82, 45.87, 44.90, 42.77, 40.04, 38.10, 35.00, 30.66, 30.65, 21.09, 20.04, 10.98; HRMS (ESI-TOF): m/z calcd for $C_{38}H_{48}N_3O_{22}S_3Na$ [M+Na]$^-$ 1017.1795. obsd 1017.9629.

3,4-Di-O-benzyl-2-O-sulfonato-α-L-idopyranosiduronate-(1→4)-2-sulfonatamido-3,6-di-O-sulfonato-1-O-(2-(2-((2S)bicyclo[2.2.1]hept-5-en-2-ylmethoxy)ethoxy)ethyl)-2-deoxy-β-D-glucopyranoside (28)

To a solution of 33 (78.0 mg, 0.079 mol) in THF (10.0 mL) and NaOH (0.1 M solution, 4.70 mL) at rt was added $PMe_3$ (1 M in THF, 0.630 mL). The reaction mixture was stirred overnight and then neutralized with a 0.1 M solution of HCl. After concentration in vacuo, the residue was purified by Sephadex® LH-20 (MeOH), and the crude product was used for the next reaction. $^1$H NMR (500 MHz; $CD_3OD$): δ 7.47 (d, J=7.8 Hz, 2H), 7.43-7.20 (m, 6H), 6.09 (ddd, J=22.5, 5.7, 2.9 Hz, 2H), 4.65 (d, J=11.8 Hz, 2H), 4.56 (d, J=10.3 Hz, 2H), 4.33 (q, J=8.2 Hz, 3H), 4.25 (s, 1H), 4.08-3.98 (m, 1H), 3.94 (s, 2H), 3.87-3.77 (m, 1H), 3.77-3.58 (m, 13H), 3.59-3.49 (m, 1H), 3.48-3.39 (m, 1H), 2.76 (d, J=37.3 Hz, 2H), 1.73-1.65 (m, 1H), 1.36 (dd, J=20.9, 12.3 Hz, 3H), 1.29-1.20 (m, 1H), 1.21-1.11 (m, 1H); HRMS (ESI-TOF): m/z calcd for $C_{38}H_{49}NO_{22}S_3Na$ [M+2H+Na]$^-$ 990.1806. obsd 990.2563. To a solution of this intermediate (78.2 mg, 0.079 mmol) in anhydrous pyridine (15 mL) and $Et_3N$ (3 mL) at rt was added $SO_3.pyr$ (375 mg, 2.37 mmol). The reaction mixture was stirred for 24 h and then quenched with $Et_3N$ (5 mL) and MeOH (10 mL). After concentration in vacuo, the residue was purified by Sephadex® LH-20 (MeOH) to obtain 28 (45.5 mg) in 54% yield over two steps as a white solid. $^1$H NMR (500 MHz; $CD_3OD$): δ 7.58-7.51 (m, 2H), 7.41-7.20 (m, 8H), 6.10 (ddd, J=26.5, 5.8, 3.0 Hz, 2H), 4.97 (d, J=12.4 Hz, 1H), 4.72 (d, J=12.4 Hz, 1H), 4.66 (d, J=6.3 Hz, 1H), 4.49 (d, J=12.3 Hz, 2H), 4.43 (d, J=10.8 Hz, 1H), 4.33-4.18 (m, 4H), 4.18-4.09 (m, 2H), 4.03 (ddd, J=9.9, 5.8, 3.8 Hz, 3H), 3.90-3.61 (m, 7H), 3.57 (td, J=9.9, 6.4 Hz, 1H), 3.52-3.39 (m, 1H), 3.37 (s, 1H), 2.77 (d, J=20.4 Hz, 2H), 1.72 (dt, J=13.6, 6.8 Hz, 1H), 1.39-1.29 (m, 3H), 1.25 (d, J=7.1 Hz, 1H), 1.19-1.14 (m, 1H); $^{13}$C NMR (126 MHz; $(CD_3)_2SO$): δ 172.59, 138.60, 138.46, 136.53, 136.35, 128.33, 128.01, 127.82, 127.65, 127.32, 126.96, 101.02, 76.54, 74.88, 73.70, 71.30, 70.88, 70.36, 70.05, 69.81, 69.63, 69.50, 68.97, 67.32, 64.83, 55.73, 55.31, 44.67, 43.20, 41.00, 38.46, 31.28, 29.26, 22.09, 21.01, 18.65, 13.96; HRMS (ESI-TOF): m/z calcd for $C_{38}H_{46}NO_{25}S_4Na$ [M+Na]$^-$ 1067.1134. obsd 1067.7520.

Polymerization Procedure

In a typical polymerization experiment, a small vial was charged with monomer 28 (22.0 mg, 0.021 mmol) and a small stir bar under the flow of argon. To this was added dry, degassed MeOH (150 µL) and dry, degassed $(CH_2Cl)_2$ (750 µL). The ratio of MeOH:$(CH_2Cl)_2$ varied from 1:4 to 1:2.5 depending on the target polymer length. A ratio of 1:4 MeOH:$(CH_2Cl)_2$ was used to synthesize polymers 35-4, 35-6, and 35-8, a ratio of 1:3 MeOH:$(CH_2Cl)_2$ was used for polymers 35-10 and 35-15, and a ratio of 1:2.5 MeOH:$(CH_2Cl)_2$ was used for the synthesis of polymers 35-30 and 35-45. Increased amounts of MeOH were required to accommodate the insolubility of the longer polymer chains. The monomer solution was heated to 55° C., stirred for 10 min, and $[(H_2IMes)(py)_2(Cl)_2Ru=CHPh]$ (34, 0.013 M stock solution in $(CH_2Cl)_2$) was quickly added via syringe. The solution was stirred at 55° C. for 2 h until it became cloudy and TLC of the reaction mixture indicated complete consumption of the monomer. The polymerization reaction was quenched by the addition of ethyl vinyl ether (300 µL). The solvent was removed in vacuo to obtain a solid precipitate, which was dissolved in a minimal amount of 10:1 $CH_2Cl_2$:MeOH and slowly added to 25 mL of hexanes in a 50 mL beaker. To collect the precipitant, this solution was centrifuged, and the hexanes layer was decanted to obtain polymer 35 as a white solid. $^1H$ NMR of the crude product showed disappearance of the norbornene olefinic protons at ~6 ppm, indicating completion of the polymerization reaction. The resulting pellet was then dried and purified using a Sephadex G-50 column eluted with $H_2O$.

The series of purified polymer 35 was characterized by $^1H$ NMR spectroscopy and gel permeation chromatography (GPC)/size exclusion chromatography-multi-angle light scattering (SEC-MALS). For GPC experiments, the polymers were dissolved in a solution of 0.2 M LiBr in DMF and analyzed on two I-series Mixed Bed Low Molecular Weight ViscoGel columns (Viscotek), connected in series with a DAWN EOS MALS detector and an Optilab DSP differential refractometer (both from Wyatt Technology). $^1H$ NMR (400 MHz; $D_2O$): δ 7.39-7.11 (m, 10H), 4.94-4.87 (m, 1H), 4.81-4.68 (m, 1H), 4.69-4.60 (m, 1H), 4.61-4.53 (m, 1H), 4.53-4.44 (m, 2H), 4.38 (bs, 3H), 4.28 (bs, 2H), 4.23-4.09 (m, 3H), 4.10-4.00 (m, 1H), 4.00-3.74 (m, 4H), 3.73-3.37 (m, 6H), 4.23-4.09 (m, 2H), 2.22-1.99 (m, 2H), 1.99-1.70 (m, 3H), 1.69-1.37 (m, 3H).

Polymer Hydrogenolysis:

Polymer 35 (21 mg) and 20% $Pd(OH)_2/C$ (126 mg, 6× by weight) were dissolved in a 1:3 mixture of phosphate buffer (80 mM, pH=7.2) and MeOH (2 mL). The reaction vessel was equipped with a $H_2$ balloon and stirred at rt for 2 days. The reaction mixture was filtered through a Millipore nylon membrane (pore size 0.45 µM, filter diameter 47 mm, Product #HNWP04700), and the membrane filter was washed with warm water (37° C.). The filtrate was lyophilized, dissolved in $H_2O$ (500 µL), and purified through a Sephadex G-50 column eluted with $H_2O$. The resulting lyophilized product was then desalted using a Sephadex G-25 column in $H_2O$. Product fractions were lyophilized to obtain the target polymer 26. $^1H$ NMR (500 MHz; $D_2O$): δ 5.16 (bs, 1H), 4.85-4.73 (m, 1H), 4.63-4.52 (m, 1H), 4.40-4.32 (m, 1H), 4.31-4.20 (m, 3H), 4.05 (bs, 1H), 4.03-3.92 (bs, 3H), 3.82-3.53 (m, 16H), 3.51-3.44 (m, 1H), 3.37-3.22 (bs, 2H), 1.89-1.70 (m, 2H), 1.68-1.55 (bs, 1H), 1.51-1.08 (m, 8H).

Properties of synthesized polymers are listed in Table 4:

TABLE 4

Heparin Glycopolymer Properties

| Entry | Polymer | Mol % 34 | MeOH:$(CH_2Cl)_2$ | n (DP) | $M_n$ (g/mol) | PDI |
|---|---|---|---|---|---|---|
| 1 | 35-4 | 30 | 1:4 | 4 | 4,373 | 2.03 |
| 2 | 35-6 | 17 | 1:4 | 6 | 6,167 | 1.25 |
| 3 | 35-10 | 10.7 | 1:3 | 10 | 11,207 | 1.29 |
| 4 | 35-15 | 6.5 | 1:3 | 15 | 15,452 | 1.32 |
| 5 | 35-30 | 5.2 | 1:2.5 | 30 | 32,721 | 1.41 |
| 6 | 35-45 | 2.0 | 1:2.5 | 45 | 42,970 | 1.25 |
| 7 | 27-35 | 4.0 | 1:10 | 155 | 164,345 | 1.62 | wherein DP, number average molecular weight (Mn), and polydispersity index (PDI) were determined by SEC-MALS in 0.2 M LiBr in DMF or 100 mM $NaNO_3$, 200 ppm $NaN_3$ in $H_2O$.

Example 9: Chromogenic Assays for the Measurement of Anti-FXa and Anti-FIIa Activity All reagents were prepared according to the manufacturer's instructions and incubated at 37° C. for 15 min. Varying concentrations of heparin, low molecular weight heparin, Arixtra® or glycopolymers (0.0005-500 µg/mL; 40 µL) and ATIII (0.04 IU; 40 µL) were added to a microcentrifuge tube, mixed, and incubated at 37° C. for 2 min. To this, FXa (0.32 µg; 40 µL) was added and was incubated at 37° C. for exactly 2 min (stage 1), then FXa chromogenic substrate (48 µmol; 40 µL) was added. Exactly 2 min later (stage 2), the reaction was stopped by introducing citric acid (240 µL; 20 g/L solution). Absorbance at 405 nm was measured on a Uvikon XL spectrophotometer. The sample blank was obtained by mixing the reagents in reverse order from that of the test, i.e. citric acid, FXa substrate, FXa, ATIII, and heparinized sample. The sample blank value was deducted from the absorbance measured for the corresponding assay.

All reagents were prepared according to the manufacturer's instructions and incubated at 37° C. for 15 min. Varying concentrations of heparin, low molecular weight heparin, or glycopolymers (0.0005-500 µg/mL; 40 µL) and ATIII (0.01 IU; 40 µL) were added to a microcentrifuge tube, mixed, and incubated at 37° C. for 2 min. To this, FIIa (1.2 nkat; 40 µL) was added and was incubated at 37° C. for exactly 2 min (stage 1), then FIIa chromogenic substrate (0.05 mmol; 40 µL) was added. Exactly 2 min later (stage 2), the reaction was stopped by introducing citric acid (240 µL; 20 g/L). Absorbance at 405 nm was measured. The sample blank was obtained by mixing the reagents in reverse order from that of the test, i.e. citric acid, FXa substrate, FXa, ATIII, and heparinized sample. The sample blank value was deducted from the absorbance measured for the corresponding assay.

The anticoagulant activities of the glycopolymers, heparin, LMW heparin (LMWH) and Arixtra were assessed and compared by the above-mentioned assays, with the results shown in FIGS. 12A and 12B and Table 5.

TABLE 5

Biological Activity of Heparan Sulfate (HS) Glycopolymers

|  | Anti-FXa IC50 (nM) | Anti-FIIa IC50 (nM) | APTT (s) | PT (s) |
|---|---|---|---|---|
| 26-4 | >2000 | >2000 | 32.5 ± 0.3 | 13.2 ± 0.1 |
| 26-6 | >2000 | >2000 | 32.2 ± 0.2 | 13.2 ± 0.3 |
| 26-10 | >2000 | >2000 | 59.6 ± 0.3 | 15.8 ± 0.4 |
| 26-15 | 1470 ± 578 | >2000 | 82.9 ± 0.6 | 23.4 ± 1.9 |

TABLE 5-continued

Biological Activity of Heparan Sulfate (HS) Glycopolymers

|  | Anti-FXa IC50 (nM) | Anti-FIIa IC50 (nM) | APTT (s) | PT (s) |
|---|---|---|---|---|
| 26-30 | 684 ± 60 | 577 ± 31 | 100.8 ± 0.6 | 50.8 ± 6.3 |
| 26-45 | 5.76 ± 0.04 | 0.114 ± 10$^{-4}$ | 119.4 ± 0.5 | 52.2 ± 7.8 |
| 27-35 | >2000 | >2000 | 46.1 ± 0.4 | 12.7 ± 0.1 |
| None | >2000 | >2000 | 31.2 ± 0.3 | 13.3 ± 0.1 |
| Heparin | 16.5 ± 1.2 | 11.0 ± 0.1 | >180 | 84.2 ± 17.8 |
| LMWH | 526 ± 71 | >2000 | 117 ± 3 | 14.8 ± 0.2 |
| Arixtra | 11.0 ± 0.1 | >2000 | 78.3 ± 0.4 | 15.1 ± 0.3 |

LMWH, and Arixtra attenuated FXa activity in the presence of ATIII, with half maximal inhibitory concentrations (IC50) of 16.5±1.2, 526±71, and 11.0±0.1 nM, respectively (Table 5). Glycopolymer 26-45 showed greater anti-FXa activity compared to the clinical anticoagulants, exhibiting an IC50 value of 5.76±0.04 nM (FIG. 13A, Table 5). The precise contribution from the glucosaminyl 3-O-sulfate modification on unit H was also assessed by comparing the activity of the glycopolymers to that of 3-O-desulfated glycopolymer 27-35. This single alteration in sulfation pattern reduced the anti-FXa activity, reaffirming the importance of 3-O-sulfation and the specificity of the polymer interaction with ATIII (FIG. 13A, Table 5).

Also, as shown in FIGS. 12A and 12B, FIG. 13B and Table 5, heparin displayed strong anti-FIIa activity (IC50=11.0±0.1 nM), whereas LMWH and Arixtra had no appreciable activity. While the glycopolymer 26-45 was found to be 100-fold more potent than heparin at inhibiting FIIa (IC50=114±1 pM).

Example 10: Chromogenic Assays for the Measurement of Platelet Factor 4 (PF4) Neutralization All reagents were prepared according to the manufacturer's instructions and incubated at 37° C. for 15 min. Varying concentrations of heparin, low molecular weight heparin, or glycopolymers (0.0005-500 µg/mL; 40 µL) and ATIII (0.01 IU; 40 µL) were added to a microcentrifuge tube, mixed, and incubated at 37° C. for 2 min. To this, FIIa (1.2 nkat; 40 µL) was added and was incubated at 37° C. for exactly 2 min (stage 1) in the presence or absence of PF4 (20 µg mL-1). FIIa chromogenic substrate (0.05 mmol; 40 µL) was then added and incubated for exactly 2 min (stage 2). The reaction was stopped by introducing citric acid (240 µL), and absorbance at 405 nm was measured. The sample blank was obtained by mixing the reagents in reverse order from that of the test, i.e. citric acid, FXa substrate, FXa, ATIII, and heparinized sample. The sample blank value was deducted from the absorbance measured for the corresponding assay.

To assess potential interaction with PF4, the ability of PF4 to neutralize the anti-FIIa activity of glycopolymers 26-45 and 26-30 was evaluated. PF4 was added to the glycopolymers or heparin (0.5-500 µg/mL) in the presence of ATIII and excess FIIa, and FIIa activity was measured using the same chromogenic assay. Both heparin (FIG. 14; A) and glycopolymer 26-45 (FIG. 14; C) interacted strongly with PF4, the anti-FIIa activity of glycopolymer 1-30 was partially neutralized by PF4 (FIG. 14B), indicating PF4 reactivity associated with HIT can be minimized by modulating the polymer length.

Example 11: Activated Partial Thromboplastin Time and Prothrombin Time Analysis

Plasma/anticoagulant samples were prepared by mixing 300 µL of the heparin standard or glycopolymer (150 µg/mL) in 0.9% saline and 2.7 mL of citrated human plasma. The tube was inverted 3 times to mix the sample thoroughly. Samples were analyzed by the UCLA Clinical & Translational Research Laboratory using a Sysmex® CA-1500 Coagulation Analyzer (Siemens AG, Erlangen, Germany). Clotting time in the absence of an anticoagulant was determined using 0.9% saline solution water (300 µL). Each clotting assay was performed in triplicate.

Samples were prepared by mixing 300 µL of the heparin standard or glycopolymer (150 µg/mL) in 0.9% saline with 2.7 mL citrated human plasma. The tube was inverted 3 times to mix the sample thoroughly. Samples were analyzed by the UCLA Clinical & Translational Research Laboratory using a Sysmex® CA-1500 Coagulation Analyzer (Siemens AG, Erlangen, Germany). Clotting time in the absence of an anticoagulant was determined using 0.9% saline solution water (300 µL). Each clotting assay was performed in triplicate.

The activated partial thromboplastin time (APTT) and prothrombin time (PT) of each compound were measured to determine whether the intrinsic and/or extrinsic pathways of the blood coagulation cascade, respectively, were inhibited. As shown in Table 5, heparin increased both the APTT and PT for clotting compared to the saline control, whereas LMWH and Arixtra at the same concentration increased only the APTT. Notably, the APTT of the glycopolymers could be controlled by varying the polymer length, with a minimum of 10 disaccharide epitopes (26-10) required to prolong the APTT. A slight increase to 15 units (26-15) endowed the polymer with APTT properties similar to Arixtra, whereas the PT was not appreciably altered in either case. Glycopolymers 26-30 and 26-45 modulated both the APTT and PT, in agreement with their ability to inhibit FXa and FIIa in vitro. While the APTTs of 26-30 and 26-45 were comparable to those of LMWH and Arixtra, their PTs more closely resembled that of heparin.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A glycopolymer comprising a plurality of repeating units, wherein each of said repeating units comprises a saccharide moiety (SA), a linking group (L) and a polymer backbone moiety (PB), wherein said repeating units are optionally connected by one or more carbon-carbon double bonds, wherein said glycopolymer is of the formula:

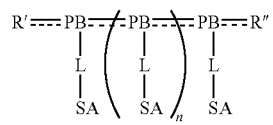

or a pharmaceutically acceptable salt thereof,
wherein:
R' and R" are each independently selected from the group consisting of unsubstituted or substituted alkyl, unsubstituted or substituted heteroalkyl, unsubstituted or substituted aryl, unsubstituted or substituted heteroaryl, unsubstituted or substituted cycloalkyl, and unsubstituted or substituted heterocycloalkyl;

each of the repeating units is of the formula:

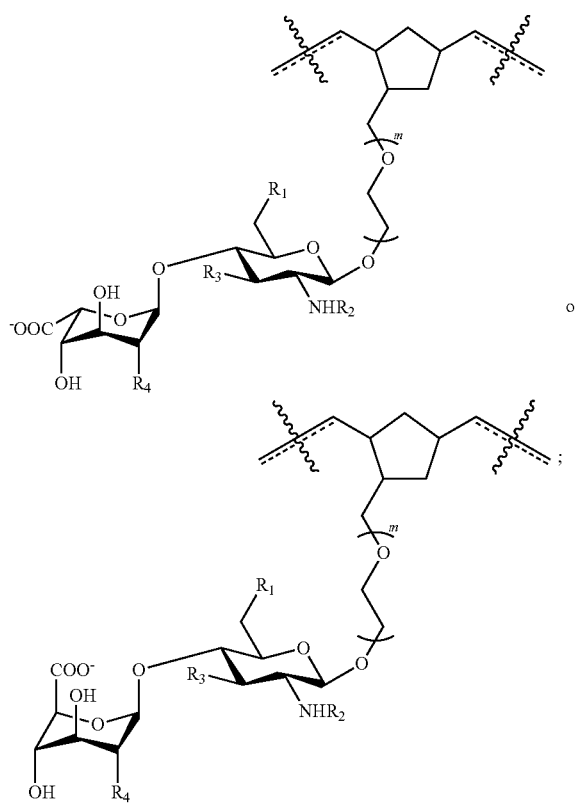

$R_1$ and $R_4$ are sulfate, and $R_2$ is sulfite;

m is 2; and n is an integer between 30 and 45.

2. The glycopolymer of claim 1, wherein R' is unsubstituted or substituted cycloalkyl.

3. The glycopolymer of claim 1, wherein R" is unsubstituted or substituted alkyl.

4. The glycopolymer of claim 3, wherein the polydispersity index of said glycopolymer is less than about 1.5.

5. The glycopolymer of claim 3, wherein the polydispersity index of said glycopolymer is less than about 4.

6. The glycopolymer of claim 5, wherein R' is unsubstituted cycloalkyl.

7. The glycopolymer of claim 6, wherein R" is unsubstituted alkyl.

8. The glycopolymer of claim 1, wherein n is 30 or 45.

9. A composition comprising a substantially homogeneous population of a glycopolymer of claim 1.

10. A pharmaceutical composition comprising a glycopolymer of claim 1, and a pharmaceutically acceptable carrier.

11. A pharmaceutical composition comprising a glycopolymer of claim 1, and a second pharmaceutical agent.

12. A kit comprising a glycopolymer of claim 1.

13. A substrate, immobilized thereon a glycopolymer of claim 1.

14. The substrate of claim 13, wherein said substrate comprises a solid support.

15. The substrate of claim 13, wherein said substrate is an array.

* * * * *

UNITED STATES PATENT AND TRADEMARK OFFICE
CERTIFICATE OF CORRECTION

| | | |
|---|---|---|
| PATENT NO. | : 9,770,461 B2 | Page 1 of 1 |
| APPLICATION NO. | : 14/450196 | |
| DATED | : September 26, 2017 | |
| INVENTOR(S) | : Young In Oh et al. | |

It is certified that error appears in the above-identified patent and that said Letters Patent is hereby corrected as shown below:

In the Specification

Column 1, delete Lines 13-15 and replace with the following:
-- This invention was made with government support under Grant No. GM093627 awarded by the National Institutes of Health. The government has certain rights in the invention. --

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*